(12) United States Patent
Gruber et al.

(10) Patent No.: US 8,709,981 B2
(45) Date of Patent: Apr. 29, 2014

(54) ISOLATED AUSTRALIAN CORAL REEF FLUORESCENT PROTEINS AND CELL-BASED KINASE OR PHOSPHATASE PLATFORMS FOR CANCER DRUG DEVELOPMENT

(76) Inventors: David Gruber, Fair Lawn, NJ (US); Hung-Teh Kao, Providence, RI (US); Vincent Pieribone, New Haven, CT (US)

( * ) Notice: Subject to any disclaimer, the term of this patent is extended or adjusted under 35 U.S.C. 154(b) by 5 days.

(21) Appl. No.: 13/496,574

(22) PCT Filed: Sep. 16, 2010

(86) PCT No.: PCT/US2010/049181
§ 371 (c)(1),
(2), (4) Date: Jun. 4, 2012

(87) PCT Pub. No.: WO2011/035067
PCT Pub. Date: Mar. 24, 2011

(65) Prior Publication Data
US 2012/0252698 A1    Oct. 4, 2012

Related U.S. Application Data

(60) Provisional application No. 61/243,024, filed on Sep. 16, 2009, provisional application No. 61/350,630, filed on Jun. 2, 2010.

(51) Int. Cl.
*C40B 40/10* (2006.01)

(52) U.S. Cl.
USPC .............................................. 506/18

(58) Field of Classification Search
None
See application file for complete search history.

(56) References Cited

U.S. PATENT DOCUMENTS

2007/0122851 A1*    5/2007    Matz et al. ................ 435/7.1

* cited by examiner

*Primary Examiner* — Tracy Vivlemore
*Assistant Examiner* — Karen S Weiler
(74) *Attorney, Agent, or Firm* — Scully, Scott, Murphy & Presser, P.C.

(57) ABSTRACT

The present invention concerns novel isolated fluorescent proteins, variants thereof, and polynucleotides encoding the same. Methods for making and using the polypeptides and polynucleotides are also provided. For example, methods to detect protein-protein interactions, to develop novel fluorescent reagents, to monitor cellular events, as well as cell-based methods for screening for kinase or phosphatase inhibitors, are set forth. Kits to carry out the methods of the invention are also taught.

9 Claims, 19 Drawing Sheets

Red fluorescent protein amino acid sequence

```
              *          *          *          *          *   * * *** 
  1   mrssknvike fmrfkvrmeg tvnghefeie gegegrpyeg [hn]t[v][k]lkvtk ggplpfawdi
              *
 61   lspqfQYGsk vyvkhpadip dykklsfpeg fkwervmnfe dggvvtvtqd sslqdgcfiy
                                    *                  * * ****
121   kvkfigvnfp sdgpvmqkkt mgweasterl yprdgvlkge ihkalklkdg ghylvefksi
                                                      *
181   ymakkpvqlp gyyyvdskld itshnedyti veqyertegr hhlfl
```

*Asterisks are highly variable amino acids
[Boxed] residues are both homologous Perlecan-binding residues in Nidogens
and highly variable residues in fluorescent proteins
CAPITAL sequence (QYG) are the chromophore forming residues.

FIG. 9
A
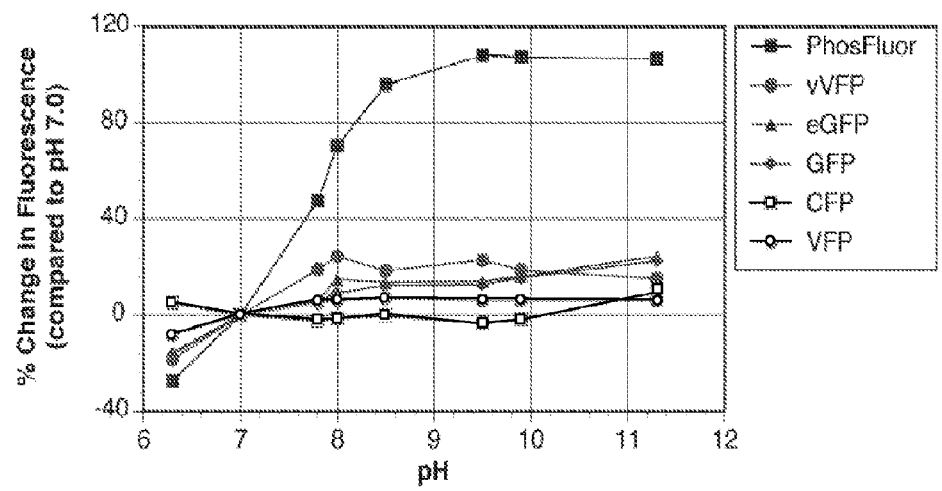
B
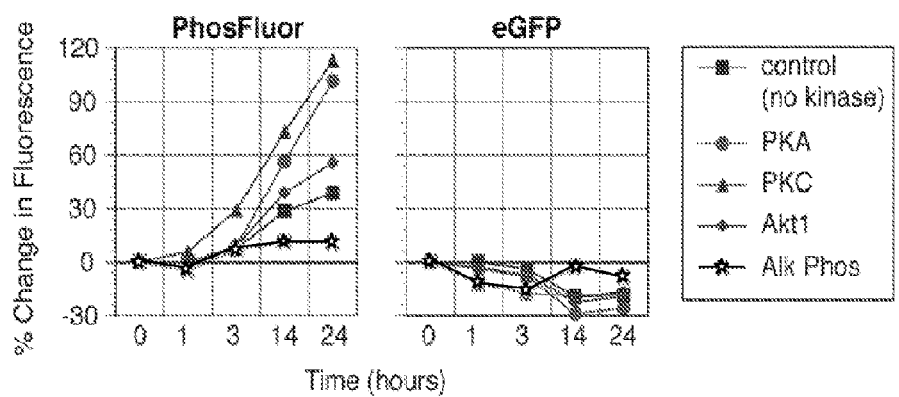

SEQUENCE LISTING

<160> NUMBER OF SEQ ID NOS: 71

<210> SEQ ID NO 1
<211> LENGTH: 24
<212> TYPE: DNA
<213> ORGANISM: Artificial Sequence
<220> FEATURE:
<223> OTHER INFORMATION: Descrpition of Artifical Sequence: Synthetic Primer

<400> SEQUENCE: 1
araaggcgca ccwctsccwt tygc    24

```
<210> SEQ ID NO 2
<211> LENGTH: 29
<212> TYPE: DNA
<213> ORGANISM: Artificial Sequence
<220> FEATURE:
<223> OTHER INFORMATION: Descrpition of Artifical Sequence: Synthetic
      Primer

<400> SEQUENCE: 2
agccyctgcc tttygcgttt gacatattg                                     29

<210> SEQ ID NO 3
<211> LENGTH: 29
<212> TYPE: DNA
<213> ORGANISM: Artificial Sequence
<220> FEATURE:
<223> OTHER INFORMATION: Descrpition of Artifical Sequence: Synthetic
      Primer

<400> SEQUENCE: 3
agccyctgcc tttygcgttt gacatattg                                     29

<210> SEQ ID NO 4
<211> LENGTH: 21
<212> TYPE: DNA
<213> ORGANISM: Artificial Sequence
<220> FEATURE:
<223> OTHER INFORMATION: Descrpition of Artifical Sequence: Synthetic
      Primer

<400> SEQUENCE: 4
cccctkccat tctcctttga c                                             21

<210> SEQ ID NO 5
<211> LENGTH: 33
<212> TYPE: DNA
<213> ORGANISM: Artificial Sequence
<220> FEATURE:
<223> OTHER INFORMATION: Descrpition of Artifical Sequence: Synthetic
      Primer

<400> SEQUENCE: 5
gaaggcgsdc ctctgccbtt ctcttwtgat atc                                33

<210> SEQ ID NO 6
<211> LENGTH: 32
<212> TYPE: DNA
<213> ORGANISM: Artificial Sequence
<220> FEATURE:
<223> OTHER INFORMATION: Descrpition of Artifical Sequence: Synthetic
      Primer

<400> SEQUENCE: 6
gtcttcttyt gcatmacwgg wccatyrgca gg                                 32

<210> SEQ ID NO 7
<211> LENGTH: 27
<212> TYPE: DNA
<213> ORGANISM: Artificial Sequence
<220> FEATURE:
<223> OTHER INFORMATION: Descrpition of Artifical Sequence: Synthetic
      Primer

<400> SEQUENCE: 7
agcgatcttc ttctgcatra ctggwcc                                       27

<210> SEQ ID NO 8
```

-continued

```
<211> LENGTH: 32
<212> TYPE: DNA
<213> ORGANISM: Artificial Sequence
<220> FEATURE:
<223> OTHER INFORMATION: Descrpition of Artifical Sequence: Synthetic
      Primer

<400> SEQUENCE: 8
atcttcttct gcatractgg wccattggsr gg                                     32

<210> SEQ ID NO 9
<211> LENGTH: 31
<212> TYPE: DNA
<213> ORGANISM: Artificial Sequence
<220> FEATURE:
<223> OTHER INFORMATION: Descrpition of Artifical Sequence: Synthetic
      Primer

<400> SEQUENCE: 9 gtcttttgc atcacrggtc cgtyrsyrgg g                                       31

<210> SEQ ID NO 10
<211> LENGTH: 230
<212> TYPE: PRT
<213> ORGANISM: Scleractinia sp

<400> SEQUENCE: 10

Met Ser Ala His Ile Lys Pro Asn Met Lys Ile Lys Leu Arg Met Glu
1               5                   10                  15

Gly Asp Val Asn Gly His Pro Phe Val Ile Thr Gly Glu Gly Ser Gly
            20                  25                  30

Lys Pro Tyr Glu Gly Thr His Ala Ile Asp Leu Lys Val Lys Glu Gly
        35                  40                  45

Gly Pro Leu Pro Phe Ala Tyr Asp Ile Leu Thr Ala Ala Phe Gln Tyr
    50                  55                  60

Gly Asn Arg Ala Phe Thr Lys Tyr Pro Ala Asp Ile Pro Asp Tyr Phe
65                  70                  75                  80

Lys Gln Ser Phe Pro Asp Gly Tyr Cys Trp Glu Arg Ser Met Val Phe
                85                  90                  95

Glu Asp Gln Gly Ile Cys Val Val Lys Ser Val Ile Ser Leu Asp Lys
            100                 105                 110

Lys Glu Pro Asp Cys Phe Asn Tyr Asp Ile Arg Phe Tyr Gly Val Asn
        115                 120                 125

Phe Pro Ala Thr Gly Pro Val Met Lys Lys Thr Val Lys Trp Glu
    130                 135                 140

Pro Ser Thr Gln Thr Met Tyr Glu Arg Asp Gly Val Leu Val Gly Asp
145                 150                 155                 160

Val Asn Met Ala Leu Leu Leu Glu Gly Gly Gly His His Arg Cys Asp
                165                 170                 175

Phe Lys Ser Thr Tyr Arg Ala Lys Gly Val Val Leu Asn Met Pro Gly
            180                 185                 190

Asn His Tyr Val Asp His Arg Ile Glu Ile Ile His Asp Lys Gly
        195                 200                 205

Tyr Asn Ser Val Thr Val His Glu Ser Ala Glu Ala Arg His Cys Ser
    210                 215                 220

Leu Pro Ser Lys Ala Lys
225                 230

<210> SEQ ID NO 11
<211> LENGTH: 792
```

-continued

```
<212> TYPE: DNA
<213> ORGANISM: Scleractinia sp

<400> SEQUENCE: 11
cagatcgaac aaaactagca ctgtaagatc gattatctta ttttacgaat accgtcatga     60
gtgcgcatat aaaaccaaac atgaagatca agctgcgtat ggagggcgat gtaaacgggc    120
acccgttcgt gattacagga gaaggaagcg gcaagcctta cgaaggaaca cacgctatag    180
accttaaagt caaagaaggt ggacctctcc cattcgctta cgatatcttg acagcagctt    240
tccagtacgg caacagggca ttcaccaaat atccagcaga catcccagac tatttcaagc    300
agtcttttcc tgatgggtat tgctgggaac ggagcatggt tttcgaggac cagggcattt    360
gcgtggtcaa aagcgtaata tcgttagaca aaaaggaacc tgactgtttc aactacgaca    420
ttcgatttta tggtgtaaac tttcctgcca ctggtccagt tatgaagaag aagacggtga    480
aatgggagcc atccactcag actatgtatg aacgtgatgg agtgctagtg ggtgatgtta    540
acatggctct gttgcttgaa ggaggcggtc atcaccgatg cgacttcaaa gtacttaca     600 gagcaaaggg agttgttctg aacatgccag ggaatcacta cgtggatcat cgtattgaga    660
taatacacca tgacaaaggt tataacagcg tgacggttca tgagtctgcc gaagctcgcc    720
attgttcgct gccgagcaag gccaagtaaa ggcttagcat gaaacccagt agacaacaag    780
gagcaaaaaa at                                                        792

<210> SEQ ID NO 12
<211> LENGTH: 225
<212> TYPE: PRT
<213> ORGANISM: Scleractinia sp
<220> FEATURE:
<221> NAME/KEY: UNSURE
<222> LOCATION: (76)..(76)
<223> OTHER INFORMATION: Xaa is any amino acid
<220> FEATURE:
<221> NAME/KEY: UNSURE
<222> LOCATION: (103)..(103)
<223> OTHER INFORMATION: Xaa is any amino acid
<220> FEATURE:
<221> NAME/KEY: UNSURE
<222> LOCATION: (133)..(133)
<223> OTHER INFORMATION: Xaa is any amino acid
<220> FEATURE:
<221> NAME/KEY: UNSURE
<222> LOCATION: (136)..(136)
<223> OTHER INFORMATION: Xaa is any amino acid

<400> SEQUENCE: 12

Met Asn Val Ile Lys Thr Asp Met Lys Met Lys Leu Arg Met Val Gly
1               5                   10                  15

Ala Val Asn Gly His Lys Phe Glu Ile Ala Gly Glu Gly Lys Gly Lys
                20                  25                  30

Pro Phe Glu Gly Lys Gln Thr Met Asn Leu Glu Val Leu Val Gly Gly
            35                  40                  45

Pro Leu Pro Phe Ala Phe Asp Ile Leu Thr Thr Val Phe Asp Tyr Gly
        50                  55                  60

Asn Arg Val Phe Val Lys Tyr Pro Lys Asp Ile Xaa Asx Tyr Phe Lys
65                  70                  75                  80

Gln Ser Phe Pro Glu Gly Phe Ser Trp Glu Arg Ser Met Ala Tyr Glu
                85                  90                  95

Asp Gly Gly Ile Cys Ile Xaa Thr Asn Asx Ile Thr Leu Met Lys Gly
            100                 105                 110

Asp Cys Phe Leu Tyr Glu Ile Arg Phe Asp Gly Val Asn Phe Pro Ala
        115                 120                 125
```

Asn Ser Pro Val Xaa Gln Lys Xaa Thr Val Lys Trp Glu Pro Ser Thr
            130                 135                 140

Glu Lys Leu Tyr Val Arg Asp Gly Val Leu Lys Gly Asp Val Asn Met
145                 150                 155                 160

Ala Leu Leu Leu Glu Glu Gly Gly His Tyr Arg Cys Asp Phe Lys Thr
                165                 170                 175

Thr Tyr Lys Ser Lys Lys Val Val Gln Leu Pro Asp Tyr His Phe Val
            180                 185                 190

Asp His Arg Ile Glu Ile Glu Ser His Asp Lys Asp Tyr Asn Lys Val
            195                 200                 205

Lys Leu Cys Glu His Ala Glu Ala His Ser Gly Leu Pro Arg Gln Ala
    210                 215                 220

Lys
225

<210> SEQ ID NO 13
<211> LENGTH: 980
<212> TYPE: DNA
<213> ORGANISM: Scleractinia sp

<400> SEQUENCE: 13
atcgagaaca actagaactg tataaggcac atatcctact tacgtccatc atcatgaatg      60
tgattaagac agacatgaag atgaagttgc gaatggtagg cgctgtaaac gggcacaagt     120
tcgaaatcgc aggagaaggg aaaggcaagc cttttgaggg aaaacagact atgaacctgg     180
aagtcctagt cggcggacct ctgcctttcg ctttcgatat cttgacaaca gtattcgatt     240
acggcaacag ggtgtttgtc aaatacccaa aagatatmsc mractatttc aagcagtcst     300
ttcccgaggg cttttcmtgg gagcgaagca tggcttatga agacgggggg atttgcatcs     360
ccacaaacra cataacattg atgaaaggcg actgttttct ttatgaaatt cgatttgatg     420
gagtgaactt tcctgccaat agcccagttw tgcagaagar gaccgtgaaa tgggagccat     480
ccactgagaa attgtacgtg cgtgatggag tgctgaaggg tgatgttaac atggctctgt     540
tgcttgaaga aggtggccat taccgatgtg acttcaaaac tacttataaa tctaagaagg     600
ttgtccagtt gccagactat cactttgtgg atcaccgaat tgagatagaa agccatgaca     660
aagattacaa caaggttaag ctgtgtgagc atgccgaagc tcattctggg ctgccaaggc     720
aggccaagta aaggctaaac gaccaaccaa gacgagaaca agcagaaaaa agcatttttt     780
agcgtgaaag tgtttaatcg gaattagtat ttgataccct caattcatgg acttcttttg     840
ggttttctag gcactagctt taaagttaaa tttagttaac ttccatttat gtgggatttc     900
ggcagagacc cacttgtagt caaatgtaag taagaagaca gtagtaagaa taaacttgtt     960
gtcgaatacc aaaaaaaaaa                                                 980

<210> SEQ ID NO 14
<211> LENGTH: 225
<212> TYPE: PRT
<213> ORGANISM: Scleractinia sp

<400> SEQUENCE: 14

Met Ser Val Ile Lys Gln Glu Met Lys Ile Lys Leu Arg Met Glu Gly
1               5                   10                  15

Thr Val Asn Gly His Ser Phe Val Ile Glu Gly Glu Gly Lys Gly Lys
            20                  25                  30

Pro Tyr Glu Gly Thr Gln Thr Ile Asn Leu Thr Val Lys Glu Gly Ala
        35                  40                  45

Pro Leu Pro Phe Ala Tyr Asp Ile Leu Thr Ser Gly Phe Gln Tyr Gly
        50                  55                  60

Asn Arg Ala Phe Thr Lys Tyr Pro Ser Asp Ile Pro Asp Tyr Phe Lys
 65                  70                  75                  80

Gln Thr Phe Pro Glu Gly Tyr Ser Trp Glu Arg Ser Met Thr Tyr Glu
                 85                  90                  95

Asp Gln Gly Ile Cys Thr Ile Thr Ser Asp Ile Arg Met Glu Asp Asp
            100                 105                 110

Cys Phe Met Tyr Glu Ile Arg Phe Lys Gly Glu Asn Phe Ser Pro Asn
        115                 120                 125

Gly Pro Val Met Gln Lys Lys Thr Leu Lys Trp Glu Pro Ser Thr Glu
130                 135                 140

Lys Met Tyr Val Arg Asp Gly Val Leu Lys Gly Asp Val Asn Met Ala
145                 150                 155                 160

Leu Leu Leu Asp Gly Gly Gly His Tyr Arg Cys Asp Phe Arg Ser Thr
                165                 170                 175

Tyr Lys Ala Lys Lys Val Val Asn Leu Pro Asp Tyr His Phe Val Asp
            180                 185                 190

His Arg Ile Glu Ile Leu Ser His Asp Lys Asp Tyr Ser Lys Val Lys
        195                 200                 205

Leu Tyr Glu Asn Ala Val Ala Arg Tyr Ser Met Leu Pro Ser Gln Ala
210                 215                 220

Lys
225

<210> SEQ ID NO 15
<211> LENGTH: 797
<212> TYPE: DNA
<213> ORGANISM: Scleractinia sp

<400> SEQUENCE: 15
agagcagatc gagaaaaata agagctgtaa ggttgacatc ctactttacg tctaccatca      60
tgagtgtgat taaacaagag atgaagatta agctgcgcat ggaaggcacc gtaaacgggc     120
acagcttcgt gattgaagga gaaggaaaag gcaaaccttta cgaaggaaca cagactataa    180
accttacagt caaagaaggc gcacctctgc ctttcgctta cgatatcttg acgtcaggat     240
tccagtacgg caacagggca ttcaccaaat acccatcaga tatcccgac tatttcaagc      300 agacttttcc tgagggatat tcctgggaaa gaagcatgac ttatgaagac agggcatttt    360
gtaccataac aagcgatata agaatggaag acgactgttt catgtatgaa attcgcttta    420
aaggggagaa cttttccccc aatggtccag ttatgcagaa gaagacgctg aaatgggagc    480
catccactga agatgtgtac gtgcgtgatg gggtgctgaa gggtgatgtt aacatggccc    540
ttttgcttga tggaggtggt cattaccgat gtgacttcag aagtacttac aaggcgaaga    600
aggttgtcaa cttgccagac tatcactttg tggaccaccg cattgagatt ttgagccacg    660
acaaagatta cagtaaagtt aagctgtacg agaacgccgt tgctcgctat tctatgctgc    720
cgagtcaggc caagtaaagg cttcacgaaa acccgagacg acaacaaaga gcgaaaattg    780
tttgtcatcg actggag                                                   797

<210> SEQ ID NO 16
<211> LENGTH: 156
<212> TYPE: PRT
<213> ORGANISM: Lobophyllia hemprichii

<400> SEQUENCE: 16

```
Ala Leu Gly Ile Cys Leu Ala Thr Asn Asp Ile Thr Leu Lys Gly Asp
1               5                   10                  15

Cys Lys Leu Arg Met Val Gly Ala Val Asn Gly His Lys Phe Glu Ile
            20                  25                  30

Ala Gly Glu Gly Lys Gly Lys Pro Phe Glu Gly Lys Gln Thr Met Asp
        35                  40                  45

Leu Lys Val Leu Val Gly Gly Pro Leu Pro Phe Ala Tyr Asp Ile Leu
    50                  55                  60

Thr Thr Val Phe Asp Tyr Gly Asn Arg Val Phe Val Lys Tyr Pro Asx
65                  70                  75                  80

Asx Ile Glu Gly His Phe Lys Gln Ser Phe Pro Glu Gly Phe Ser Trp
                85                  90                  95

Gln Arg Ser Met Ala Tyr Glu Asp Gly Gly Ile Cys Leu Ala Thr Asn
                100                 105                 110

Asp Ile Thr Leu Lys Gly Asp Cys Phe Leu Tyr Glu Ile Arg Phe Asp
            115                 120                 125

Gly Val Asn Phe Pro Ala Asn Ser Pro Val Met Gln Lys Lys Thr Val
        130                 135                 140

Lys Trp Glu Pro Ser Thr Glu Lys Leu Tyr Val Arg
145                 150                 155
```

<210> SEQ ID NO 17
<211> LENGTH: 469
<212> TYPE: DNA
<213> ORGANISM: Lobophyllia hemprichii

<400> SEQUENCE: 17

```
gcccttggca tttgcctcgc cacaaacgac ataacattga aaggcgactg taagctgcga    60
atggtgggcg ctgtaaacgg cacaagttc gaaatcgcag agaagggaa aggcaagcct   120
tttgagggaa aacagactat ggacctgaaa gtcctagtcg gcggtcctct gcctttcgct   180
tacgatatct tgacaacagt attcgattac ggcaacaggg tattcgtcaa ataccccarat   240
ratatagaag gcacttcaa gcagtcattt cccgagggat tttcatggca gcgaagcatg   300
gcttatgaag acggggcat tgcctcgcc acaaacgaca taacattgaa aggcgactgt   360
tttctttatg aaattcgatt tgatggagtg aactttcctg ccaatagccc ggttatgcag   420
aagaagaccg tgaaatggga gccatccact gagaaactgt atgtgcgtg               469
```

<210> SEQ ID NO 18
<211> LENGTH: 146
<212> TYPE: PRT
<213> ORGANISM: Lobophyllia hemprichii

<400> SEQUENCE: 18

```
Pro Leu Ala Phe Lys Ala Thr Val Lys Met Lys Leu Arg Met Val Gly
1               5                   10                  15

Ala Val Asn Gly His Lys Phe Glu Ile Ala Gly Glu Gly Lys Gly Lys
            20                  25                  30

Pro Phe Glu Gly Lys Gln Thr Met Asn Leu Glu Val Leu Val Gly Gly
        35                  40                  45

Pro Leu Pro Phe Ala Phe Asp Ile Leu Thr Thr Val Phe Asp Tyr Gly
    50                  55                  60

Asn Arg Val Phe Val Lys Tyr Pro Asn Asp Ile Ala Asp Tyr Phe Lys
65                  70                  75                  80

Gln Ser Phe Pro Glu Gly Phe Ser Trp Glu Arg Ser Met Ala Tyr Glu
                85                  90                  95
```

```
Asp Gly Gly Ile Cys Ile Ala Thr Asn Asp Ile Thr Leu Lys Gly Asp
            100                 105                 110
Cys Phe Leu Tyr Glu Ile Arg Phe Asp Gly Val Asn Phe Pro Ala Asn
        115                 120                 125
Ser Pro Val Met Gln Lys Arg Thr Val Lys Trp Glu Pro Ser Thr Glu
    130                 135                 140
Lys Leu
145

<210> SEQ ID NO 19
<211> LENGTH: 466
<212> TYPE: DNA
<213> ORGANISM: Scleractinia sp

<400> SEQUENCE: 19
gcccttggca tttgcatcgc cacaaacgac ataacattga aaggcgactg tgaagatgaa    60
gttgcgaatg gtaggcgctg taaacgggca caagttcgaa atcgcaggag aagggaaagg   120
caagcctttt gagggaaaac agactatgaa cctggaagtc ctagtcggcg gacctctgcc   180
tttcgctttc gatatcttga caacagtatt cgattacggc aacagggtgt ttgtcaaata   240
cccaaacgat atagcagact atttcaagca gtcgtttccc gaaggctttt catgggagcg   300
aagcatggct tatgaagacg ggggcatttg catcgccaca aacgacataa cattgaaagg   360
cgactgtttt ctttatgaaa ttcgatttga tggagtgaac tttcctgcca atagcccagt   420
tatgcagaag aggaccgtga aatgggagcc atccactgag aaattg                  466

<210> SEQ ID NO 20
<211> LENGTH: 137
<212> TYPE: PRT
<213> ORGANISM: Lobophyllia hemprichii

<400> SEQUENCE: 20

Met Asn Val Ile Lys Thr Asp Met Lys Met Lys Leu Arg Met Val Gly
1               5                   10                  15
Ala Val Asn Gly His Lys Phe Glu Ile Ala Gly Glu Gly Lys Gly Lys
            20                  25                  30
Pro Phe Glu Gly Lys Gln Thr Met Asn Leu Glu Val Leu Val Gly Gly
        35                  40                  45
Pro Leu Pro Phe Ala Phe Asp Ile Leu Thr Thr Val Phe Asp Tyr Gly
    50                  55                  60
Asn Arg Val Phe Val Lys Tyr Pro Arg Asp Ile Ala Asp Tyr Phe Lys
65                  70                  75                  80
Gln Ser Phe Pro Glu Gly Phe Ser Trp Glu Arg Ser Met Ala Tyr Glu
                85                  90                  95
Asp Gly Gly Ile Cys Leu Ala Thr Asn Asp Ile Thr Leu Lys Gly Asp
            100                 105                 110
Cys Phe Leu Tyr Glu Ile Arg Phe Asp Gly Val Asn Phe Pro Ala Asn
        115                 120                 125
Ser Pro Val Leu Gln Lys Lys Thr Val
    130                 135

<210> SEQ ID NO 21
<211> LENGTH: 497
<212> TYPE: DNA
<213> ORGANISM: Scleractinia sp
<220> FEATURE:
<221> NAME/KEY: misc_feature
<222> LOCATION: (14)..(14)
```

-continued

<223> OTHER INFORMATION: n is a, c, g, or t

<400> SEQUENCE: 21

```
caaatcacca gggntgattt ggaagagagg agatcgagaa caactagaac tgtataaggc      60
acatatccta cttacgtcca tcatcatgaa tgtgattaag acagacatga agatgaagtt     120
gcgaatggta ggcgctgtaa acgggcacaa gttcgaaatc gcaggagaag gaaaggcaa     180
gccttttgag ggaaaacaga ctatgaacct ggaagtccta gtcggcggac ctctgccttt     240
cgctttcgat atcttgacaa cagtattyga ttacggcaac agggtgtttg tcaaataccc     300
aagagatata gcagactatt tcaagcagtc gtttcccgag ggcttttcat gggagcgaag     360
catggcttat gaagacgggg gcatttgcct cgccacaaac gacataacat tgaaaggcga     420
ctgttttctt tatgaaattc gatttgatgg agtgaacttt cctgccaata gcccagtttt     480
gcagaagaag accgtga                                                    497
```

<210> SEQ ID NO 22
<211> LENGTH: 225
<212> TYPE: PRT
<213> ORGANISM: Scleractinia sp
<220> FEATURE:
<221> NAME/KEY: UNSURE
<222> LOCATION: (15)..(15)
<223> OTHER INFORMATION: Xaa is any amino acid
<220> FEATURE:
<221> NAME/KEY: UNSURE
<222> LOCATION: (43)..(43)
<223> OTHER INFORMATION: Xaa is any amino acid
<220> FEATURE:
<221> NAME/KEY: UNSURE
<222> LOCATION: (45)..(45)
<223> OTHER INFORMATION: Xaa is any amino acid

<400> SEQUENCE: 22

Met Asn Val Ile Lys Thr Asp Met Lys Met Lys Leu Arg Met Xaa Gly
1               5                   10                  15

Ala Val Asn Gly His Lys Phe Val Ile Ala Gly Glu Gly Arg Gly Gln
            20                  25                  30

Pro Phe Glu Gly Lys Gln Thr Met Asp Leu Xaa Val Xaa Glu Gly Gly
        35                  40                  45

Pro Leu Pro Phe Ala Phe Asp Ile Leu Thr Thr Val Phe Asp Tyr Gly
    50                  55                  60

Asn Arg Val Phe Val Lys Tyr Pro Arg Asp Ile Ala Asp Tyr Phe Lys
65                  70                  75                  80

Gln Ser Phe Pro Glu Gly Phe Ser Trp Glu Arg Ser Met Ala Tyr Glu
                85                  90                  95

Asp Gly Gly Ile Cys Ile Ala Thr Asn Asn Ile Thr Leu Met Lys Gly
            100                 105                 110

Asp Cys Phe Leu Tyr Glu Ile Arg Phe Asp Gly Val Asn Phe Pro Ala
        115                 120                 125

Asn Ser Pro Val Met Gln Lys Arg Thr Val Lys Trp Glu Pro Ser Thr
    130                 135                 140

Glu Lys Leu Tyr Val Arg Asp Gly Val Leu Lys Gly Asp Val Asn Met
145                 150                 155                 160

Ala Leu Leu Leu Glu Glu Gly Gly His Tyr Arg Cys Asp Phe Lys Thr
                165                 170                 175

Thr Tyr Lys Ser Lys Lys Val Val Gln Leu Pro Asp Tyr His Phe Val
            180                 185                 190

Asp His Arg Ile Glu Ile Glu Ser His Asp Lys Asp Tyr Asn Lys Val
        195                 200                 205

Lys Leu Cys Glu His Ala Glu Ala His Ser Gly Leu Pro Arg Gln Ala
    210                 215                 220

Lys
225

<210> SEQ ID NO 23
<211> LENGTH: 798
<212> TYPE: DNA
<213> ORGANISM: Scleractinia sp

<400> SEQUENCE: 23
caaatcacca gggtgatttg aagagagga gatcgagaac aactagaact gtataaggca    60
catatcctac ttacgtccat catcatgaat gtgattaaga cagacatgaa ratgaagytg   120
cgwatggwag gcgctgtaaa cgggcacaag tttgtgattg caggggaagg aagaggccag   180
cctttcgagg gaaaacagac tatggaccctt rcagtcmaag aaggcggacc tctgcctttc   240
gctttcgata tcttgacaac agtatttgac tacggcaaca gggtgtttgt caaatacccca   300 agagatatag cagactattt caagcagtcg tttcccgagg gcttttcatg ggagcgaagc   360
atggcttatg aagacggggg satttgcatc gccacaaaca acataacatt gatgaaaggc   420
gactgttttc tttatgaaat tcgatttgat ggagtgaact ttcctgccaa tagcccagtt   480
atgcagaaga ggaccgtgaa atgggagcca tccactgaga aattgtacgt gcgtgatgga   540
gtgctgaagg gtgagttaac atggctctgt tgcttgaaga aggtggccat taccgatgtg   600
acttcaaaac tacttataaa tctaagaagg ttgtccagtt gccagactat cactttgtgg   660
atcaccgaat tgagatagaa agccatgaca aagattacaa caaggttaag ctgtgtgagc   720
atgccgaagc tcattctggg ctgccaaggc aggccaagta aaggctaaac gaccaaccaa   780
gacgagaaca agcgaaaa                                                 798

<210> SEQ ID NO 24
<211> LENGTH: 138
<212> TYPE: PRT
<213> ORGANISM: Lobophyllia hemprichii

<400> SEQUENCE: 24

Met Asn Val Ile Lys Thr Asp Met Lys Met Lys Leu Arg Met Val Gly
1               5                   10                  15

Ala Val Asn Gly His Lys Phe Glu Ile Ala Gly Glu Gly Lys Gly Lys
            20                  25                  30

Pro Phe Glu Gly Lys Gln Thr Met Asn Leu Glu Val Leu Val Gly Gly
        35                  40                  45

Pro Leu Pro Phe Ala Phe Asp Ile Leu Thr Thr Val Phe Asp Tyr Gly
    50                  55                  60

Asn Arg Val Phe Val Lys Tyr Pro Arg Asp Ile Ala Asp Tyr Phe Lys
65                  70                  75                  80

Gln Ser Phe Pro Glu Gly Phe Ser Trp Glu Arg Ser Met Ala Tyr Glu
                85                  90                  95

Asp Gly Gly Ile Cys Leu Ala Thr Asn Asn Ile Thr Leu Met Lys Gly
            100                 105                 110

Asp Cys Phe Leu Tyr Glu Ile Arg Phe Asp Gly Val Asn Phe Pro Ala
        115                 120                 125

Asn Ser Pro Val Leu Gln Lys Lys Thr Val
    130                 135

<210> SEQ ID NO 25

```
<211> LENGTH: 500
<212> TYPE: DNA
<213> ORGANISM: Lobophyllia hemprichii
<220> FEATURE:
<221> NAME/KEY: misc_feature
<222> LOCATION: (14)..(14)
<223> OTHER INFORMATION: n is a, c, g, or t

<400> SEQUENCE: 25
caaatcacca gggntgattt ggaagagagg agatcgagaa caactagaac tgtataaggc      60
acatatccta cttacgtcca tcatcatgaa tgtgattaag acagacatga agatgaagtt     120
gcgaatggta ggcgctgtaa acgggcacaa gttcgaaatc gcaggagaag ggaaaggcaa     180
gccttttgag ggaaaacaga ctatgaacct ggaagtccta gtcggcggac ctctgccttt     240
cgctttcgat atcttgacaa cagtattyga ttacggcaac agggtgtttg tcaaataccc     300
aagagatata gcagactatt tcaagcagtc gtttcccgag ggcttttcat gggagcgaag     360
catggcttat gaagacgggg gcatttgcct cgccacaaac aacataacat tgatgaaagg     420
cgactgtttt ctttatgaaa ttcgatttga tggagtgaac tttcctgcca atagcccagt     480
tttgcagaag aagaccgtga                                                 500

<210> SEQ ID NO 26
<211> LENGTH: 172
<212> TYPE: PRT
<213> ORGANISM: goniastrea australensis
<220> FEATURE:
<221> NAME/KEY: UNSURE
<222> LOCATION: (111)..(113)
<223> OTHER INFORMATION: Xaa is any amino acid
<220> FEATURE:
<221> NAME/KEY: UNSURE
<222> LOCATION: (136)..(136)
<223> OTHER INFORMATION: Xaa is any amino acid

<400> SEQUENCE: 26
```

Gly Thr Arg Leu Lys Tyr Leu Trp Phe Ala Asn Val Lys Asp Ser Met
1               5                  10                  15

Gly Lys Gln Thr Met Asp Leu Thr Val Ile Glu Gly Ala Pro Leu Pro
            20                  25                  30

Phe Ala Phe Asp Ile Leu Thr Thr Val Phe Glu Tyr Gly Asn Arg Val
        35                  40                  45

Phe Ala Lys Tyr Pro Lys Glu Ile Pro Asp Tyr Phe Lys Gln Ser Phe
    50                  55                  60

Pro Glu Gly Tyr Ser Trp Gln Arg Ser Met Thr Tyr Glu Asp Gly Gly
65                  70                  75                  80

Val Cys Gln Ala Ser Asn Asp Ile Lys Ile Lys Glu Asp Asp Ser
                85                  90                  95

Cys Phe Val Tyr Glu Ile Arg Phe Asp Gly Val Asn Phe Pro Xaa Xaa
            100                 105                 110

Xaa Pro Val Met Gln Lys Lys Thr Val Lys Trp Glu Pro Ser Thr Glu
        115                 120                 125

Lys Met Tyr Val Arg Asp Gly Xaa Leu Lys Gly Asp Val Asn Met Ala
    130                 135                 140

Leu Leu Leu Gln Gly Gly Gly His Tyr Arg Cys Asp Phe Lys Thr Thr
145                 150                 155                 160

Tyr Lys Ala Lys Lys Ala Val Gln Leu Pro Arg Ala
                165                 170

```
<210> SEQ ID NO 27
<211> LENGTH: 518
```

-continued

```
<212> TYPE: DNA
<213> ORGANISM: goniastrea australensis

<400> SEQUENCE: 27
cggcacgagg ctcaagtatc tgtggtttgc gaatgtaaaa gatagcatgg gaaagcagac      60
tatggacctg acagtcatag aaggcgcacc tcttcctttc gctttcgata tcttgacaac     120
agtattcgag tacggcaatc gagtattcgc caaatacccm aaagaaatac cagactattt     180
caagcagtcg tttcctgagg ggtattcctg caacgaagc atgacttatg aagacggtgg     240
cgtttgccaa gcctcaaatg acataaaaat taaagaagat gacgacagct gttttgtcta     300
tgaaattcga tttgatggtg tgaactttcc ykccrrtrgt ccagttatgc agaagaagac     360
cgtcaaatgg gagccatcca ctgagaaaat gtatgtgcgt gatggaryrc tgaagggtga     420
tgtwaacatg gcyctgttgc ttcaaggagg tggccattac cgatgcgact caaaactac     480 ttacaaagct aagaaggctg tccaattgcc tcgtgccg                             518
```

```
<210> SEQ ID NO 28
<211> LENGTH: 236
<212> TYPE: PRT
<213> ORGANISM: Scleractinia sp

<400> SEQUENCE: 28

Met Ser Ala Ile Lys Pro Asp Met Lys Ile Lys Leu His Met Lys Gly
1               5                   10                  15

Ala Val Asn Gly His Ile Phe Glu Ile Asp Gly Glu Gly Asn Gly Lys
            20                  25                  30

Pro Phe Glu Gly Lys Gln Thr Ile Glu Leu Lys Val Val Asp Gly Gly
        35                  40                  45

Pro Leu Pro Phe Ala Phe Asp Ile Leu Thr Thr Val Phe Glu Tyr Gly
    50                  55                  60

Asn Arg Val Phe Ala Lys Tyr Pro Pro Glu Ile Val Asp Tyr Phe Lys
65                  70                  75                  80

Gln Ser Phe Pro Glu Gly Tyr Ser Trp Glu Arg Ser Met Met Tyr Glu
                85                  90                  95

Asp Gly Gly Ile Cys Ile Ala Thr Asn Asn Ile Thr Leu Leu Lys Asp
            100                 105                 110

Ala His Gly Val Asp Tyr Phe Tyr Asn Ile Arg Phe Asp Gly Val
        115                 120                 125

Asn Phe Pro Thr Asn Gly Pro Val Met Gln Lys Lys Thr Val Lys Trp
    130                 135                 140

Glu Pro Ser Thr Glu Lys Met Tyr Val Arg Asp Gly Val Leu Lys Gly
145                 150                 155                 160

Asp Val Asn Met Ala Leu Leu Ile Glu Gly Gly His Asn Arg Cys
                165                 170                 175

Asp Phe Lys Thr Thr Tyr Lys Ala Arg Lys Ala Val Pro Leu Pro Asn
            180                 185                 190

Tyr His Phe Val Asp His Arg Ile Glu Ile Val Ser His Asp Arg Asp
        195                 200                 205

Tyr Asn His Val Lys Leu Cys Glu His Ala Glu Ala His Ser Gly Leu
    210                 215                 220

Pro Ser Ser Arg Lys Ala Arg Gln Ile Ser Thr Glu
225                 230                 235
```

```
<210> SEQ ID NO 29
<211> LENGTH: 814
<212> TYPE: DNA
```

<213> ORGANISM: Scleractinia sp

<400> SEQUENCE: 29

```
gcagaacgtg aagcacaagt gttgtataag gcggatatct acctttacgt ctaccatcat    60
gagtgcgatt aaaccagata tgaagatcaa gcttcatatg aagggcgctg taaacgggca   120
cattttcgag attgatggag aaggaaacgg gaagcctttt gagggaaaac agaccatcga   180
gctgaaagtc gtagacggcg gacctctgcc gtttgctttc gatatcttga caacggtatt   240
cgaatatggc aacagggtat tcgccaaata tccacctgag atagtagact atttcaagca   300
gtcatttcct gaagggtatt cctgggaacg aagcatgatg tacgaagatg gaggcatttg   360
catcgccaca aacaacataa cactgctgaa agacgcccac ggcgttgact atttctacta   420
taacattcga tttgatggtg tgaactttcc caccaatggt ccagttatgc agaaaaagac   480
cgtgaaatgg gagccatcca ctgagaaaat gtatgtgcgc gatggagtgc taaagggtga   540
tgttaacatg gctttgttga ttgaaggagg tggtcataac cgatgtgact caaaactac   600
ttataaagct aggaaggctg tcccgttgcc aaactatcac tttgtggacc accgcataga   660
gattgtcagc cacgcagag attacaatca cgttaagctg tgtgagcatg ccgaagctca   720
ttccgggcta ccgagctcga gaaaggcgcg ccaaatttca acagaaagaa ttcggcacga   780
ggggtattcg ccaaatatcc acctgagata gtag                               814
```

<210> SEQ ID NO 30
<211> LENGTH: 234
<212> TYPE: PRT
<213> ORGANISM: Scleractinia sp

<400> SEQUENCE: 30

```
Glu Ser Tyr Phe Ser Pro Glu Glu Ser Val Ile Ser Ser Val Met Asn
1               5                   10                  15

Ile Lys Leu Arg Met Glu Gly Glu Val Asn Gly His Lys Phe Thr Val
            20                  25                  30

Glu Gly Glu Gly Ser Gly Lys Pro Tyr Glu Gly Thr Gln Thr Ile Asp
        35                  40                  45

Leu Glu Val Thr Glu Gly Gly Pro Leu Pro Phe Ala Phe Asp Ile Leu
    50                  55                  60

Thr Thr Ala Phe Gln Tyr Gly Asn Arg Ala Phe Thr Lys Tyr Pro Ala
65                  70                  75                  80

Asp Ile Pro Asp Tyr Phe Lys Glu Ser Phe Pro Glu Gly His Ser Trp
                85                  90                  95

Val Arg Thr Met Val Phe Asp Asp Gly Gly Val Cys Asp Val Thr Asn
            100                 105                 110

Asp Ile Arg Met Tyr Gly Asn Val Phe Glu Tyr Glu Ile Thr Phe His
        115                 120                 125

Cys Asn Asn Phe Glu Leu Ser Gly Pro Ile Met Gln Lys Glu Thr Leu
    130                 135                 140

Lys Trp Glu Pro Ser Cys Glu Gly Met Tyr Ala Gly Lys Asn Gly Val
145                 150                 155                 160

Leu Leu Gly Asp Glu Phe Arg His Leu Leu Leu Val Gly Gly Gly His
                165                 170                 175

Phe Arg Cys Asp Cys Ser Pro Tyr Ser Ala Lys Lys Arg Val Glu
            180                 185                 190

Met Pro Lys Tyr His Phe Ile Asp His Arg Ile Glu Ile Val Ser His
        195                 200                 205

Asp Lys Asp Tyr Gln Lys Val Lys Val Tyr Glu Ile Ala Glu Ala Lys
```

```
                210                 215                 220
Tyr Ser Pro Leu Pro Glu Ser Lys Ala Lys
225                 230
```

<210> SEQ ID NO 31
<211> LENGTH: 849
<212> TYPE: DNA
<213> ORGANISM: Scleractinia sp

<400> SEQUENCE: 31

```
attttgcaga agtcttacat cgtccaagtc ccaaatggcg tccttttcg tcgttatatc      60
cgtcttgcta tgttgtgctt ccggtaaccc tgttcatagt aactacgagc gaacagagga    120
gtcctatttt tcacctgaag agagtgttat tagctcagtc atgaacatca agctgcgtat    180
ggaaggcgaa gtaaacgggc acaagttcac cgttgaagga gaaggatcag ggaagcctta    240
cgaaggaacg cagactatag accttgaagt cacagaaggc gggcctctcc cttttgcttt    300
cgacatcttg acaacagcat tccagtacgg caacagggcg ttcaccaaat cccagcaga    360
cataccggac tatttcaagg agtccttcc tgagggtcat tcctgggtgc gaaccatggt     420
tttcgatgac ggaggggttt gcgacgtgac aaacgacata agaatgtatg gtaacgtttt    480
tgaatatgag atcacatttc attgcaacaa ctttgaactc agtggtccaa ttatgcagaa    540
agagacattg aaatgggaac catcctgtga gggaatgtat gctggtaaaa acggagtttt    600
actaggagat gagttcaggc atctgttgct tgtaggaggc ggccattttc gatgtgattg    660
cagcccttct tacagtgcca agaagagggt cgagatgccc aaataccact tcattgacca    720
ccgcattgaa attgtaagcc atgacaaaga ttaccaaaag gttaaggtgt atgagattgc    780
tgaagctaaa tactctccac tgccggagag taaggccaag tgaaggcttc agcgaaaagc    840
taagacgac                                                             849
```

<210> SEQ ID NO 32
<211> LENGTH: 224
<212> TYPE: PRT
<213> ORGANISM: Scleractinia sp
<220> FEATURE:
<221> NAME/KEY: UNSURE
<222> LOCATION: (73)..(73)
<223> OTHER INFORMATION: Xaa is any amino acid
<220> FEATURE:
<221> NAME/KEY: UNSURE
<222> LOCATION: (76)..(77)
<223> OTHER INFORMATION: Xaa is any amino acid
<220> FEATURE:
<221> NAME/KEY: UNSURE
<222> LOCATION: (127)..(127)
<223> OTHER INFORMATION: Xaa is any amino acid
<220> FEATURE:
<221> NAME/KEY: UNSURE
<222> LOCATION: (129)..(129)
<223> OTHER INFORMATION: Xaa is any amino acid
<220> FEATURE:
<221> NAME/KEY: UNSURE
<222> LOCATION: (146)..(146)
<223> OTHER INFORMATION: Xaa is any amino acid

<400> SEQUENCE: 32

```
Met Ser Val Ile Lys Ala Asp Met Lys Met Lys Leu Arg Met Val Gly
1               5                   10                  15

Ala Val Asn Gly His Lys Phe Glu Ile Ala Gly Glu Gly Lys Gly Lys
                20                  25                  30

Pro Phe Glu Gly Lys Gln Thr Met Asp Leu Lys Val Leu Val Gly Gly
            35                  40                  45
```

```
Pro Leu Pro Phe Ala Tyr Asp Ile Leu Thr Thr Val Phe Asp Tyr Gly
    50                  55                  60

Asn Arg Val Phe Val Lys Tyr Pro Xaa Asp Ile Xaa Xaa Tyr Phe Lys
 65                  70                  75                  80

Gln Ser Phe Pro Glu Gly Phe Ser Trp Gln Arg Ser Met Ala Tyr Glu
                 85                  90                  95

Asp Gly Gly Ile Cys Leu Ala Thr Asn Asp Ile Thr Leu Asn Gly Asp
            100                 105                 110

Cys Phe Leu Tyr Glu Ile Arg Phe Asp Gly Val Asn Phe Pro Xaa Asn
        115                 120                 125

Xaa Pro Val Met Gln Lys Lys Thr Val Lys Trp Glu Pro Ser Thr Glu
    130                 135                 140

Lys Xaa Tyr Val Arg Asp Gly Val Leu Lys Gly Asp Val Asn Met Ala
145                 150                 155                 160

Leu Leu Leu Glu Gly Gly Gly His Tyr Arg Cys Asp Phe Lys Thr Thr
                165                 170                 175

Tyr Ile Ser Lys Lys Val Val Gln Leu Pro Asp Tyr His Phe Val Asp
            180                 185                 190

His Arg Ile Glu Ile Glu Ser His Asp Lys Asp Tyr Asn Asn Val Lys
        195                 200                 205

Leu Tyr Glu His Ala Glu Ala His Ser Gly Leu Pro Arg Gln Ala Lys
    210                 215                 220

<210> SEQ ID NO 33
<211> LENGTH: 857
<212> TYPE: DNA
<213> ORGANISM: Scleractinia sp

<400> SEQUENCE: 33
ccggcttata actggctcaa gtgcattttg ggcgagacat tcagttttaa agcagcatcg      60
tccccgctga agtcccattc accctggtga tttggtagag agcagatcaa caccatcaag     120
agctgtataa ggcagatatc ttactttcgt ccaccatcat gagtgtgatt aaagcagaca     180
tgaagatgaa gctgcgaatg gtgggcgctg taaacgggca agttcgaa atcgcaggag       240 aagggaaagg caagcctttt gagggaaaac agactatgga cctgaaagtc ctagtcggcg     300
gacctctgcc tttcgcttac gacatcttga acagtatt cgattacggc aacagggtat      360
tcgtcaaata cccaaakgat atagmagrct acttcaagca gtcatttccy gagggatttt     420
catggcagcg aagcatggct tatgaagacg gaggcatttg cctcgccaca acgacataa     480 cattaaatgg cgactgtttt ctttatgaaa ttcgatttga tggagtgaac tttccyrcca     540
atrgyccagt tatgcagaar aagaccgtga atgggagcc atccactgag aaawtgtatg     600
tgcgygatgg agtgctgaag ggggatgtta acatggctct gttgcttgaa ggaggtggtc     660
attaccgatg tgacttcaaa actacttata tatctaagaa ggttgtccaa ttgcctgact     720
atcacttcgt ggatcaccga attgagatag aaagccatga caaagattac aacaacgtca     780
agctgtatga gcatgccgaa gctcattctg ggctgccaag gcaggccaag taaaggctca     840
aaaaaaaagc caagacg                                                   857

<210> SEQ ID NO 34
<211> LENGTH: 147
<212> TYPE: PRT
<213> ORGANISM: Scleractinia sp

<400> SEQUENCE: 34

Met Ser Val Ile Lys Pro Asp Met Lys Met Lys Leu Arg Met Glu Gly
```

```
              1               5              10              15
Ala Val Asn Gly His Lys Phe Val Ile Ala Gly Glu Gly Arg Gly Gln
                 20                  25                  30

Pro Phe Glu Gly Lys Gln Thr Met Asp Leu Thr Val Lys Glu Gly Gly
             35                  40                  45

Pro Leu Pro Phe Ala Phe Asp Ile Leu Thr Thr Val Phe Asp Tyr Gly
 50                  55                  60

Asn Arg Val Phe Val Lys Tyr Pro Arg Asp Ile Ala Asp Tyr Phe Lys
 65                  70                  75                  80

Gln Ser Phe Pro Glu Gly Phe Ser Trp Glu Arg Ser Met Ala Tyr Glu
                 85                  90                  95

Asp Gly Gly Ile Cys Ile Ala Thr Asn Asn Ile Thr Leu Met Lys Gly
            100                 105                 110

Asp Cys Phe Leu Tyr Glu Ile Arg Phe Asp Gly Val Asn Phe Pro Ala
        115                 120                 125

Asn Ser Pro Val Met Gln Lys Arg Thr Val Lys Trp Glu Pro Ser Thr
    130                 135                 140

Glu Lys Leu
145

<210> SEQ ID NO 35
<211> LENGTH: 490
<212> TYPE: DNA
<213> ORGANISM: Scleractinia sp

<400> SEQUENCE: 35
tggacttaag taagatatct gccttacaca gctcttgttg ttctcgatca tgagtgtgat       60
taaaccagac atgaaaatga agctgcgtat ggaaggcgct gtaaacgggc acaagtttgt      120
gattgcaggg gaaggaagag gccagccttt cgagggaaaa cagactatgg accttacagt      180
caaagaaggc ggacctctgc ctttcgcttt cgatatcttg acaacagtat ttgactacgg      240
caacagggtg tttgtcaaat acccaagaga tatagcagac tatttcaagc agtcgtttcc      300
cgagggcttt tcatgggagc gaagcatggc ttatgaagac ggggggattt gcatcgccac      360
aaacaacata acattgatga aaggcgactg ttttctttat gaaattcgat ttgatggagt      420
gaactttccc gccaatagcc cagttatgca gaagaggacc gtgaaatggg agccatccac      480
tgagaaattg                                                             490

<210> SEQ ID NO 36
<211> LENGTH: 146
<212> TYPE: PRT
<213> ORGANISM: Scleractinia sp

<400> SEQUENCE: 36

Met Ser Val Ile Lys Pro Asp Met Lys Met Lys Leu Arg Met Glu Gly
 1               5                  10                  15

Ala Val Asn Gly His Lys Phe Val Ile Ala Gly Glu Gly Arg Gly Gln
                 20                  25                  30

Pro Phe Glu Gly Lys Gln Thr Met Asn Leu Glu Val Leu Val Gly Gly
             35                  40                  45

Pro Leu Pro Phe Ala Phe Asp Ile Leu Thr Thr Val Phe Asp Tyr Gly
 50                  55                  60

Asn Arg Val Phe Val Lys Tyr Pro Asn Asp Ile Ala Asp Tyr Phe Lys
 65                  70                  75                  80

Gln Ser Phe Pro Glu Gly Phe Ser Trp Glu Arg Ser Met Ala Tyr Glu
                 85                  90                  95
```

Asp Gly Gly Ile Cys Leu Ala Thr Asn Asp Ile Thr Leu Asn Gly Asp
                100                 105                 110

Cys Phe Leu Tyr Glu Ile Arg Phe Asp Gly Val Asn Phe Pro Ala Asn
            115                 120                 125

Ser Pro Val Met Gln Lys Arg Thr Val Lys Trp Glu Pro Ser Thr Glu
    130                 135                 140

Lys Leu
145

<210> SEQ ID NO 37
<211> LENGTH: 487
<212> TYPE: DNA
<213> ORGANISM: Scleractinia sp

<400> SEQUENCE: 37
tggacttaag taagatatct gccttacaca gctcttgttg ttctcgatca tgagtgtgat     60
taaaccagac atgaaaatga agctgcgtat ggaaggcgct gtaaacgggc acaagtttgt    120
gattgcaggg gaaggaagag gccagccttt cgagggaaaa cagactatga acctggaagt    180
cctagtcggc ggacctctgc cttcgctttt cgatatcttg acaacagtat tcgattacgg    240
caacagggtg tttgtcaaat acccaaacga tatagcagac tatttcaagc agtcgtttcc    300
cgagggcttt tcatgggagc gaagcatggc ttatgaagac ggaggcattt gcctcgccac    360
aaacgacata acattaaatg gcgactgttt tctttatgaa attcgatttg atggagtgaa    420
ctttcctgcc aatagcccag ttatgcagaa gaggaccgtg aaatgggagc catccactga    480
gaaattg                                                             487

<210> SEQ ID NO 38
<211> LENGTH: 175
<212> TYPE: PRT
<213> ORGANISM: Scleractinia sp
<220> FEATURE:
<221> NAME/KEY: UNSURE
<222> LOCATION: (114)..(114)
<223> OTHER INFORMATION: Xaa is any amino acid
<220> FEATURE:
<221> NAME/KEY: UNSURE
<222> LOCATION: (116)..(116)
<223> OTHER INFORMATION: Xaa is any amino acid
<220> FEATURE:
<221> NAME/KEY: UNSURE
<222> LOCATION: (128)..(128)
<223> OTHER INFORMATION: Xaa is any amino acid
<220> FEATURE:
<221> NAME/KEY: UNSURE
<222> LOCATION: (135)..(135)
<223> OTHER INFORMATION: Xaa is any amino acid

<400> SEQUENCE: 38

Ala Ile Lys Pro Asp Met Lys Ile Lys Leu Cys Met Glu Gly Ala Val
1               5                   10                  15

Asn Gly His Pro Phe Met Ile Glu Gly Glu Gly Lys Gly Lys Pro Phe
                20                  25                  30

Asp Gly Lys Gln Asn Met Glu Leu Lys Val Lys Glu Gly Gly Pro Leu
            35                  40                  45

Pro Phe Ala Tyr Asp Ile Leu Thr Thr Val Phe Asn Tyr Gly Asn Arg
    50                  55                  60

Val Phe Ala Lys Tyr Pro Arg Asp Ile Ala Asp Tyr Phe Lys Gln Ser
65                  70                  75                  80

Phe Pro Glu Gly Phe Ser Trp Glu Arg Ser Met Ala Tyr Glu Asp Gly
                85                  90                  95

```
Gly Ile Cys Ile Ala Thr Asn Asn Ile Thr Leu Met Lys Gly Asp Cys
            100                 105                 110

Phe Xaa Tyr Xaa Ile Arg Phe Asp Gly Val Asn Phe Pro Ala Asn Xaa
        115                 120                 125

Pro Val Met Gln Lys Lys Xaa Val Lys Trp Glu Pro Ser Thr Glu Lys
    130                 135                 140

Leu Tyr Val Arg Asp Gly Val Leu Lys Gly Asp Ile Asn Met Ala Leu
145                 150                 155                 160

Leu Leu Glu Gly Gly Gly His Tyr Arg Cys Asp Phe Lys Thr Thr
                165                 170                 175
```

<210> SEQ ID NO 39
<211> LENGTH: 525
<212> TYPE: DNA
<213> ORGANISM: Scleractinia sp
<220> FEATURE:
<221> NAME/KEY: misc_feature
<222> LOCATION: (463)..(463)
<223> OTHER INFORMATION: n is a, c, g, or t

<400> SEQUENCE: 39

```
tgcgattaag ccagacatga agatcaagct ttgtatggag ggcgctgtaa acgggcaccc    60
gttcatgatt gaaggagaag gaaaaggcaa gcctttcgac ggaaaacaga atatggaact   120
caaagtcaaa gaaggcggac tctgcccttt cgcttacgat atcttgacca cagtattcaa   180
ttacggcaac agggtattcg ccaaataccc aagagatata gcagactatt tcaagcagtc   240
atttcctgag gggttttctt gggaacgaag catggcttat gaagacgggg gcatttgcat   300
cgccacaaac aacataacat tgatgaaagg cgactgtttt stytataraaa ttcgmtttga   360
tggwgtsaac tttcctgcca atrgtccagt yatgcagaag aagaycgtga aatgggagcc   420
atccactgaa aaattgtatg tgcgtgacgg agtgctgaag ggngatatta acatggctct   480
gttgcttgaa ggaggtggcc attaccgatg tgacttcaaa actac            525
```

<210> SEQ ID NO 40
<211> LENGTH: 182
<212> TYPE: PRT
<213> ORGANISM: Scleractinia sp

<400> SEQUENCE: 40

```
Met Asn Ile Lys Leu Arg Met Glu Gly Glu Val Asn Gly His Lys Phe
1               5                   10                  15

Thr Val Glu Gly Glu Gly Ser Gly Lys Pro Tyr Glu Gly Thr Gln Thr
            20                  25                  30

Ile Asp Leu Glu Val Thr Glu Gly Gly Pro Leu Pro Phe Ala Phe Asp
        35                  40                  45

Ile Leu Thr Thr Ala Phe Gln Tyr Gly Asn Arg Ala Phe Thr Lys Tyr
    50                  55                  60

Pro Ala Asp Ile Pro Asp Tyr Phe Lys Glu Ser Phe Pro Glu Gly His
65                  70                  75                  80

Ser Trp Val Arg Thr Met Val Phe Asp Asp Gly Gly Val Cys Asp Val
                85                  90                  95

Thr Asn Asp Ile Arg Met Tyr Gly Asn Val Phe Glu Tyr Glu Thr Thr
            100                 105                 110

Phe His Cys Asn Asn Phe Asp Pro Ser Gly Pro Val Met Gln Lys Glu
        115                 120                 125

Thr Leu Lys Trp Glu Pro Ser Cys Glu Gly Met Tyr Ala Gly Lys Asn
    130                 135                 140
```

Gly Val Leu Leu Gly Asp Glu Phe Arg His Leu Leu Val Gly Gly
145                 150                 155                 160

Gly His Phe Arg Cys Asp Phe Arg Ser Thr Tyr Ser Ala Arg Lys Arg
                165                 170                 175

Val Glu Met Pro Glu Tyr
            180

<210> SEQ ID NO 41
<211> LENGTH: 594
<212> TYPE: DNA
<213> ORGANISM: Scleractinia sp

<400> SEQUENCE: 41
tttctgttgc ctaataacac tctcttcagg tgaaaaatag gacagtcatg aacatcaagc    60
tgcgtatgga aggcgaggta aacggacaca agttcaccgt tgaaggagaa ggatcaggga   120
agccttacga aggaacgcag accatagacc ttgaagtcac agaaggcggg ccgctccctt   180
ttgctttcga catcttgaca acagcwttcc agtacggcaa cagggcgttc accaaatacc   240
cagcagacat acctgactat ttcaaggagt cgtttcctga gggtcattcc tgggtgcgaa   300
ccatggtttt cgatgacgga ggggtttgcg acgtgacaaa cgacataaga atgtatggta   360 acgttttga atatgagacc acatttcatt gcaacaactt tgaccccagt ggtccagtta    420
tgcagaaaga gacgttgaaa tgggaaccat cctgtgaggg aatgtatgct ggtaaaaacg   480
gagttttact aggagatgag ttcaggcatc tgttgcttgt aggaggcggt cattttcgat   540
gtgatttcag aagtacttac agtgccagga gagggtcga gatgcccgaa tacc          594

<210> SEQ ID NO 42
<211> LENGTH: 226
<212> TYPE: PRT
<213> ORGANISM: Lobophyllia hemprichii

<400> SEQUENCE: 42

Met Ser Val Ile Lys Pro Asp Met Lys Ile Lys Leu Arg Met Glu Gly
1               5                   10                  15

Thr Val Asn Gly His Ser Phe Val Ile Asp Gly Asp Gly Lys Gly Lys
                20                  25                  30

Pro Phe Glu Gly Lys Gln Ser Met Ser Leu Glu Val Lys Glu Gly Gly
            35                  40                  45

Pro Leu Pro Phe Ser Tyr Asp Ile Leu Thr Thr Ala Phe Asn Tyr Gly
        50                  55                  60

Asn Arg Val Phe Ala Glu Tyr Pro Asp His Ile Gln Asp Tyr Phe Lys
65                  70                  75                  80

Gln Ser Phe Pro Lys Gly Tyr Ser Trp Glu Arg Ser Leu Thr Phe Glu
                85                  90                  95

Asp Gly Gly Ile Cys Ile Ala Arg Asn Asp Ile Thr Leu Glu Gly Asp
            100                 105                 110

Thr Phe Tyr Asn Lys Val Arg Phe Tyr Gly Val Asn Phe Pro Pro Asn
        115                 120                 125

Gly Pro Val Met Gln Lys Lys Thr Leu Lys Trp Glu Pro Ser Thr Glu
    130                 135                 140

Lys Met Tyr Val Arg Asp Gly Val Leu Thr Gly Asp Ile Thr Met Ala
145                 150                 155                 160

Leu Leu Leu Ile Gly Asp Val His Tyr Arg Cys Asp Phe Arg Thr Thr
                165                 170                 175

Tyr Lys Ala Arg Glu Lys Gly Val Lys Leu Pro Gly Tyr His Phe Val

```
                        180                 185                 190
Lys His Arg Ile Glu Ile Ser Ser His Asp Lys Asp Tyr Asn Lys Val
        195                 200                 205
Lys Leu Cys Glu His Ala Val Ala His Ser Gly Leu Pro Asn Asn Ala
    210                 215                 220
Arg Met
225

<210> SEQ ID NO 43
<211> LENGTH: 1191
<212> TYPE: DNA
<213> ORGANISM: Scleractinia sp

<400> SEQUENCE: 43
gaggcctcgt gccgatcgag agcaacaaaa gctgtttaag gtagacttct ttggtgcgtt      60
ttccatcatg agtgtgatta agccagacat gaagatcaag ctgcgtatgg aaggcactgt     120
aaacggccac agctttgtga ttgacggaga tggtaaaggg aagccttttg agggaaaaca     180
gagcatgagc cttgaagtaa agaaggcgg acctctgccc ttctcctacg atatcctgac      240
aacagcattc aattacggca acagggtgtt cgccgaatat ccagaccaca tacaagacta     300
tttcaagcag tcgtttccaa aggggtattc gtgggaacga agtttgactt cgaagacgg      360 gggcatttgc attgccagaa atgacattac actggaaggc gacactttct ataataaagt     420
tcgcttttat ggtgtaaatt tccccccccaa tggtccagtt atgcagaaga gacgctgaa     480 atgggagcca tccactgaga aaatgtatgt gcgtgatgga gtgttgacgg gtgatattac     540
catggctctg ttgcttatag agatgtccca ttaccgatgt gacttcagaa ctacttacaa     600
agctagggag aagggcgtca agttgccagg ctaccacttc gtgaaacacc gcattgagat     660
ttcaagccat gacaaagatt acaacaaggt taagctgtgt gagcatgccg ttgctcattc     720
tggattgccg aacaatgcca gaatgtaaaa aaaaaaacaa caacaacaaa gagaaaaaat     780
gtagcttttg gtttgttttt tttgtttgtt tgtttgtttg cttttttgccg tctcagaagg     840 ctttcaattg gaataagcat ttcatgctat cgatgcaaga atttatttcg gggttattta     900
gagacttgct ccagagtaaa gtatttggag gtaaatagtt tccactttt tggcttgact      960 gcatcacaag ataaacatt ttaatctcag ttttggataa cataaaagct ttaagggtaa     1020
tgtaatcgtg ttgtcgaggc taggttttgt gggccattct catcatagac tactagctag    1080
tggaaattta ttggttcaag gatttgtccg acatttgttg gacgccatct gtagagttga    1140
tttgtgtgaa taaatagttt ccacgttta attgattacc aaaaaaaaa a               1191

<210> SEQ ID NO 44
<211> LENGTH: 221
<212> TYPE: PRT
<213> ORGANISM: Scleractinia sp
<220> FEATURE:
<221> NAME/KEY: UNSURE
<222> LOCATION: (41)..(41)
<223> OTHER INFORMATION: Xaa is any amino acid
<220> FEATURE:
<221> NAME/KEY: UNSURE
<222> LOCATION: (53)..(53)
<223> OTHER INFORMATION: Xaa is any amino acid
<220> FEATURE:
<221> NAME/KEY: UNSURE
<222> LOCATION: (206)..(206)
<223> OTHER INFORMATION: Xaa is any amino acid

<400> SEQUENCE: 44

Met Ser Val Ile Ala Lys Gln Met Thr Tyr Lys Val Tyr Met Ser Gly
```

```
              1               5              10              15
Thr Val Asn Gly His Tyr Phe Glu Val Glu Gly Asp Gly Lys Gly Lys
                 20                  25                  30

Pro Tyr Glu Gly Glu Gln Thr Val Xaa Leu Thr Val Thr Lys Gly Gly
                 35                  40                  45

Pro Leu Pro Phe Xaa Trp Asp Ile Leu Ser Pro Gln Thr Gln Tyr Gly
 50                  55                  60

Ser Ile Pro Phe Thr Lys Tyr Pro Glu Asp Ile Pro Asp Tyr Val Lys
 65                  70                  75                  80

Gln Ser Phe Pro Glu Gly Tyr Thr Trp Glu Arg Ile Met Asn Phe Glu
                 85                  90                  95

Asp Gly Ala Val Cys Thr Val Ser Asn Asp Ser Ile Gln Gly Asn
                100                 105                 110

Cys Phe Ile Tyr Asn Val Lys Ile Ser Gly Leu Asn Phe Pro Pro Asn
                115                 120                 125

Gly Pro Val Met Gln Lys Lys Thr Gln Gly Trp Glu Pro Asn Thr Glu
130                 135                 140

Arg Leu Phe Ala Arg Asp Gly Met Leu Ile Gly Asn Asn Phe Met Ala
145                 150                 155                 160

Leu Lys Leu Glu Gly Gly His Tyr Leu Cys Glu Phe Lys Ser Thr
                165                 170                 175

Tyr Lys Ala Lys Lys Pro Val Arg Met Pro Gly Tyr His Tyr Val Asp
                180                 185                 190

Arg Lys Leu Asp Val Thr Ser His Asx Lys Asp Tyr Thr Xaa Val Glu
                195                 200                 205

Gln Cys Glu Ile Ser Ile Ala Arg His Ser Leu Leu Gly
    210                 215                 220

<210> SEQ ID NO 45
<211> LENGTH: 883
<212> TYPE: DNA
<213> ORGANISM: Scleractinia sp

<400> SEQUENCE: 45
cacagaagga gctactgtag ttaagaagcg tttgmaaatc gttgatctgc gctacttagt    60
ctcaatatga gtgtgatcgc taaacaaatg acctacaagg tttatatgtc aggcacggtc   120
aatggacact actttgaggt cgaaggcgat ggaaaaggaa agccttacga rggggagcag   180
acggtaargc tcactgtcac caagggtgga cctctgccat ttkcttggga yattttatca   240
ccacagactc agtacggaag cataccattc accaagtacc ctgaagacat ccctgattat   300
gtaaagcagt cattccctga gggatataca tgggagagga tcatgaactt tgaagatggt   360
gcagtgtgta ctgtcagcaa tgattccagc atccaaggca actgtttcat ctacaatgtc   420
aaaatctctg gtttgaactt tcctcccaat ggacctgtta tgcagaagaa gacacagggc   480 tgggaacccca acactgagcg tctctttgca cgagatggaa tgctgatagg aaacaacttt   540
atggctctga agttggaagg aggtggtcac tatttgtgtg aattcaaatc tacttacaag   600
gcaaagaagc ctgtgaggat gccagggtat cactatgttg accgcaaact ggatgtaacc   660
agtcacraca aggattacac atatgttgag cagtgtgaaa tatccattgc acgccactct   720
ttgctcggtt gacyaccttt cggagttcaa cagaaatacg cagtggctta aaaaaaaaa   780 cgtagattty gattttagct yagagaagta aaacgaaga agtgtaaaca accttcagtg   840
attaaacttt tgaaaacaaa aaaaaaaaaa aaaaaaaaa aaa                       883
```

```
<210> SEQ ID NO 46
<211> LENGTH: 6
<212> TYPE: PRT
<213> ORGANISM: Artificial Sequence
<220> FEATURE:
<223> OTHER INFORMATION: Description of Artificial Sequence: synthetic
      consensus sequence
<220> FEATURE:
<221> NAME/KEY: MOD_RES
<222> LOCATION: (2)..(2)
<223> OTHER INFORMATION: Xaa is any amino acid
<220> FEATURE:
<221> NAME/KEY: MOD_RES
<222> LOCATION: (4)..(6)
<223> OTHER INFORMATION: Xaa is any amino acid

<400> SEQUENCE: 46

Arg Xaa Arg Xaa Xaa Xaa
1               5

<210> SEQ ID NO 47
<211> LENGTH: 5
<212> TYPE: PRT
<213> ORGANISM: Artificial Sequence
<220> FEATURE:
<223> OTHER INFORMATION: Description of Artificial Sequence: synthetic
      consensus sequence
<220> FEATURE:
<221> NAME/KEY: MOD_RES
<222> LOCATION: (3)..(3)
<223> OTHER INFORMATION: Xaa is any amino acid
<220> FEATURE:
<221> NAME/KEY: MOD_RES
<222> LOCATION: (4)..(4)
<223> OTHER INFORMATION: Xaa is Ser or Thr
<220> FEATURE:
<221> NAME/KEY: MOD_RES
<222> LOCATION: (5)..(5)
<223> OTHER INFORMATION: Xaa is any hydrophobic amino acid

<400> SEQUENCE: 47

Arg Arg Xaa Xaa Xaa
1               5

<210> SEQ ID NO 48
<211> LENGTH: 7
<212> TYPE: PRT
<213> ORGANISM: Artificial Sequence
<220> FEATURE:
<223> OTHER INFORMATION: Description of Artificial Sequence: synthetic
      consensus sequence
<220> FEATURE:
<221> NAME/KEY: MOD_RES
<222> LOCATION: (5)..(5)
<223> OTHER INFORMATION: Xaa is Glu or Gly
<220> FEATURE:
<221> NAME/KEY: MOD_RES
<222> LOCATION: (6)..(6)
<223> OTHER INFORMATION: Xaa is any amino acid

<400> SEQUENCE: 48

Glu Glu Ile Tyr Xaa Xaa Phe
1               5

<210> SEQ ID NO 49
<211> LENGTH: 232
<212> TYPE: PRT
<213> ORGANISM: Acropora sp

<400> SEQUENCE: 49

Met Val Ser Tyr Ser Lys Gln Gly Ile Ala Gln Glu Met Arg Thr Lys
1               5                   10                  15
```

```
Tyr Arg Met Glu Gly Ser Val Asn Gly His Glu Phe Thr Ile Glu Gly
             20                  25                  30

Val Gly Thr Gly Asn Pro Tyr Glu Gly Lys Gln Met Ser Glu Leu Val
         35                  40                  45

Ile Ile Lys Ser Lys Gly Lys Pro Leu Pro Phe Ser Phe Asp Ile Leu
 50                  55                  60

Ser Thr Ala Phe Gln Tyr Gly Asn Arg Cys Phe Thr Lys Tyr Pro Ala
 65                  70                  75                  80

Asp Met Pro Asp Tyr Phe Lys Gln Ala Phe Pro Asp Gly Met Ser Tyr
                 85                  90                  95

Glu Arg Ser Phe Leu Phe Glu Asp Gly Gly Val Ala Thr Ala Ser Trp
            100                 105                 110

Ser Ile Arg Leu Glu Gly Asn Cys Phe Ile His Asn Ser Ile Tyr His
        115                 120                 125

Gly Val Asn Phe Pro Ala Asp Gly Pro Val Met Lys Lys Gln Thr Ile
130                 135                 140

Gly Trp Asp Lys Ser Phe Glu Lys Met Ser Val Ala Lys Glu Val Leu
145                 150                 155                 160

Arg Gly Asp Val Thr Gln Phe Leu Leu Leu Glu Gly Gly Tyr Gln
                165                 170                 175

Arg Cys Arg Phe His Ser Thr Tyr Lys Thr Glu Lys Pro Val Ala Met
                180                 185                 190

Pro Pro Ser His Val Val Glu His Gln Ile Val Arg Thr Asp Leu Gly
            195                 200                 205

Gln Thr Ala Lys Gly Phe Lys Val Lys Leu Glu Glu His Ala Glu Ala
        210                 215                 220

His Val Asn Pro Leu Lys Val Lys
225                 230

<210> SEQ ID NO 50
<211> LENGTH: 238
<212> TYPE: PRT
<213> ORGANISM: Aequorea victoria

<400> SEQUENCE: 50

Met Ser Lys Gly Glu Glu Leu Phe Thr Gly Val Val Pro Ile Leu Val
 1               5                  10                  15

Glu Leu Asp Gly Asp Val Asn Gly His Lys Phe Ser Val Ser Gly Glu
             20                  25                  30

Gly Glu Gly Asp Ala Thr Tyr Gly Lys Leu Thr Leu Lys Phe Ile Cys
         35                  40                  45

Thr Thr Gly Lys Leu Pro Val Pro Trp Pro Thr Leu Val Thr Thr Phe
 50                  55                  60

Ser Tyr Gly Val Gln Cys Phe Ser Arg Tyr Pro Asp His Met Lys Gln
 65                  70                  75                  80

His Asp Phe Phe Lys Ser Ala Met Pro Glu Gly Tyr Val Gln Glu Arg
                 85                  90                  95

Thr Ile Phe Phe Lys Asp Asp Gly Asn Tyr Lys Thr Arg Ala Glu Val
            100                 105                 110

Lys Phe Glu Gly Asp Thr Leu Val Asn Arg Ile Glu Leu Lys Gly Ile
        115                 120                 125

Asp Phe Lys Glu Asp Gly Asn Ile Leu Gly His Lys Leu Glu Tyr Asn
130                 135                 140

Tyr Asn Ser His Asn Val Tyr Ile Met Ala Asp Lys Gln Lys Asn Gly
145                 150                 155                 160
```

```
Ile Lys Val Asn Phe Lys Ile Arg His Asn Ile Glu Asp Gly Ser Val
                165                 170                 175

Gln Leu Ala Asp His Tyr Gln Gln Asn Thr Pro Ile Gly Asp Gly Pro
            180                 185                 190

Val Leu Leu Pro Asp Asn His Tyr Leu Ser Thr Gln Ser Ala Leu Ser
        195                 200                 205

Lys Asp Pro Asn Glu Lys Arg Asp His Met Val Leu Leu Glu Phe Val
    210                 215                 220

Thr Ala Ala Gly Ile Thr His Gly Met Asp Glu Leu Tyr Lys
225                 230                 235

<210> SEQ ID NO 51
<211> LENGTH: 228
<212> TYPE: PRT
<213> ORGANISM: Anemonia sulcata

<400> SEQUENCE: 51

Met Tyr Pro Ser Ile Lys Glu Thr Met Arg Val Gln Leu Ser Met Glu
1               5                   10                  15

Gly Ser Val Asn Tyr His Ala Phe Lys Cys Thr Gly Lys Gly Glu Gly
            20                  25                  30

Lys Pro Tyr Glu Gly Thr Gln Ser Leu Asn Ile Thr Ile Thr Glu Gly
        35                  40                  45

Gly Pro Leu Pro Phe Ala Phe Asp Ile Leu Ser His Ala Phe Gln Tyr
    50                  55                  60

Gly Ile Lys Val Phe Ala Lys Tyr Pro Lys Glu Ile Pro Asp Phe Phe
65                  70                  75                  80

Lys Gln Ser Leu Pro Gly Gly Phe Ser Trp Glu Arg Val Ser Thr Tyr
                85                  90                  95

Glu Asp Gly Gly Val Leu Ser Ala Thr Gln Glu Thr Ser Leu Gln Gly
            100                 105                 110

Asp Cys Ile Ile Cys Lys Val Lys Val Leu Gly Thr Asn Phe Pro Ala
        115                 120                 125

Asn Gly Pro Val Met Gln Lys Lys Thr Cys Gly Trp Glu Pro Ser Thr
    130                 135                 140

Glu Thr Val Ile Pro Arg Asp Gly Gly Leu Leu Leu Arg Asp Thr Pro
145                 150                 155                 160

Ala Leu Met Leu Ala Asp Gly Gly His Leu Ser Cys Phe Met Glu Thr
                165                 170                 175

Thr Tyr Lys Ser Lys Lys Glu Val Lys Leu Pro Glu Leu His Phe His
            180                 185                 190

His Leu Arg Met Glu Lys Leu Asn Ile Ser Asp Asp Trp Lys Thr Val
        195                 200                 205

Glu Gln His Glu Ser Val Val Ala Ser Tyr Ser Gln Val Pro Ser Lys
    210                 215                 220

Leu Gly His Asn
225

<210> SEQ ID NO 52
<211> LENGTH: 232
<212> TYPE: PRT
<213> ORGANISM: Artificial Sequence
<220> FEATURE:
<223> OTHER INFORMATION: Description of Artificial Sequence: amino acid
      sequence is identical to that accorded Genbank No. AAR85350, but
      omitting residues 8 to 37, inclusive

<400> SEQUENCE: 52
```

```
Met Asn Val Met Arg Tyr Asn Met Thr Glu Thr Phe Gln Lys Lys Leu
1               5                   10                  15

Pro Tyr Lys Leu Glu Leu Asp Gly Asp Val Asp Gly Gln Thr Phe Lys
            20                  25                  30

Val Ile Gly Glu Gly Val Gly Asp Ala Thr Thr Gly Val Ile Glu Gly
        35                  40                  45

Lys Tyr Val Cys Thr Glu Gly Glu Val Pro Ile Ser Trp Val Ser Leu
50                  55                  60

Ile Thr Ser Leu Ser Tyr Gly Ala Lys Cys Phe Val Arg Tyr Pro Asn
65                  70                  75                  80

Glu Ile Asn Asp Phe Phe Lys Ser Thr Phe Pro Ser Gly Tyr His Gln
                85                  90                  95

Glu Arg Lys Ile Thr Tyr Glu Asn Asp Gly Val Leu Glu Thr Ala Ala
            100                 105                 110

Lys Ile Thr Met Glu Ser Gly Ala Ile Val Asn Arg Ile Asn Val Lys
        115                 120                 125

Gly Thr Gly Phe Asp Lys Asp Gly His Val Cys Gln Lys Asn Leu Glu
    130                 135                 140

Ser Ser Pro Pro Ser Thr Thr Tyr Val Val Pro Glu Gly Glu Gly Ile
145                 150                 155                 160

Arg Ile Ile Tyr Arg Asn Ile Tyr Pro Thr Lys Asp Gly His Tyr Val
                165                 170                 175

Val Ala Asp Thr Gln Gln Val Asn Arg Pro Ile Arg Ala Gln Gly Thr
            180                 185                 190

Ser Ala Ile Pro Thr Tyr His His Ile Lys Ser Lys Val Asp Leu Ser
        195                 200                 205

Thr Asp Pro Glu Glu Asn Lys Asp His Ile Ile Lys Glu Thr Asn
210                 215                 220

Cys Ala Phe Asp Ala Asp Phe Ser
225                 230

<210> SEQ ID NO 53
<211> LENGTH: 223
<212> TYPE: PRT
<213> ORGANISM: Astrangia lajollaensis

<400> SEQUENCE: 53

Met Ser Leu Ser Lys Gln Val Ile Gly Lys Glu Met Asn Met Thr Tyr
1               5                   10                  15

Leu Met Asp Gly Ser Val Asn Gly His Asn Phe Thr Val Glu Gly Glu
            20                  25                  30

Gly Asp Gly Lys Pro Tyr Glu Gly His Gln Cys Leu Lys Leu Arg Ile
        35                  40                  45

Thr Lys Gly Glu Pro Leu Pro Phe Ala Phe Asp Ile Leu Thr Ala Ala
50                  55                  60

Phe Cys Tyr Gly Asn Arg Cys Phe Val Asn Tyr Pro Ala Glu Ile Ala
65                  70                  75                  80

Asp Tyr Phe Lys Gln Ala Phe Pro Glu Gly Leu Thr Trp Glu Arg Ser
                85                  90                  95

Met Thr Phe Glu Asp Gly Gly Phe Ala Ala Val Ser Ala Asp Ile Ser
            100                 105                 110

Leu Asn Gly Asn Cys Phe Val His Gln Ser Lys Phe Val Gly Val Asn
        115                 120                 125

Phe Pro Ala Asp Gly Pro Val Met Gln Lys Lys Thr Val Gly Trp Glu
    130                 135                 140
```

```
Pro Ser Thr Glu Lys Met Ile Val Arg Asp Gly Ile Leu Glu Gly Asp
145                 150                 155                 160

Val Thr Met Tyr Leu Lys Leu Glu Gly Gly Asn Tyr Arg Cys Glu
                165                 170                 175

Tyr Arg Thr Ile Tyr Lys Ala Lys Asp Val Lys Met Pro Lys Ser
            180                 185                 190

His Phe Val Glu His Thr Leu Val Arg Asn Asn Ile Lys Lys Asp Ala
        195                 200                 205

Lys Gly Asn Thr Ile Glu Leu Ile Glu Asp Ala Ser Ala Arg Tyr
210                 215                 220

<210> SEQ ID NO 54
<211> LENGTH: 218
<212> TYPE: PRT
<213> ORGANISM: Branchiostoma floridae

<400> SEQUENCE: 54

Met Ser Leu Pro Thr Thr His Asp Leu His Ile Phe Gly Ser Val Asn
1               5                   10                  15

Gly Ala Glu Phe Asp Leu Val Gly Gly Gly Lys Gly Asn Pro Asn Asp
                20                  25                  30

Gly Thr Leu Glu Thr Ser Val Lys Ser Thr Arg Gly Ala Leu Pro Cys
            35                  40                  45

Ser Pro Leu Leu Ile Gly Pro Asn Leu Gly Tyr Gly Phe Tyr Gln Tyr
50                  55                  60

Leu Pro Phe Pro Gly Gly Ala Ser Pro Phe Gln Thr Ala Ile Thr Asp
65                  70                  75                  80

Gly Gly Tyr Gln Val His Arg Val Phe Lys Phe Glu Asp Gly Gly Val
                85                  90                  95

Leu Ser Cys Asn Phe Arg Tyr Thr Tyr Glu Gly Gly Lys Ile Lys Gly
            100                 105                 110

Glu Phe Gln Leu Ile Gly Ser Gly Phe Pro Ala Gly Gly Pro Val Met
        115                 120                 125

Ser Gly Gly Leu Thr Thr Leu Asp Arg Ser Val Ala Lys Leu Gln Cys
130                 135                 140

Ser Asp Asp Cys Thr Ile Thr Gly Thr Asn Asn Trp Ser Phe Cys Thr
145                 150                 155                 160

Thr Asp Gly Lys Arg His Gln Ala Asp Val Gln Thr Asn Tyr Thr Phe
                165                 170                 175

Ala Lys Pro Leu Pro Ala Gly Leu Lys Glu Lys Met Pro Ile Phe Leu
            180                 185                 190

Gly His Gln Ile Glu Val Lys Ala Ser Lys Thr Glu Ile Thr Leu Ser
        195                 200                 205

Glu Lys Val Lys Ala Phe Ile Asp Thr Val
210                 215

<210> SEQ ID NO 55
<211> LENGTH: 222
<212> TYPE: PRT
<213> ORGANISM: Cerianthus sp

<400> SEQUENCE: 55

Met Asn Leu Ser Lys Asn Val Ser Val Ser Val Tyr Met Lys Gly Asn
1               5                   10                  15

Val Asn Asn His Glu Phe Glu Tyr Asp Gly Glu Gly Gly Gly Asp Pro
                20                  25                  30

Tyr Thr Gly Lys Tyr Ser Met Lys Met Thr Leu Arg Gly Gln Asn Cys
```

```
            35                  40                  45
Leu Pro Phe Ser Tyr Asp Ile Ile Thr Thr Ala Phe Gln Tyr Gly Phe
 50                  55                  60

Arg Val Phe Thr Lys Tyr Pro Glu Gly Ile Val Asp Tyr Phe Lys Asp
 65                  70                  75                  80

Ser Leu Pro Asp Ala Phe Gln Trp Asn Arg Arg Ile Val Phe Glu Asp
                     85                  90                  95

Gly Val Leu Asn Met Ser Ser Asp Ile Thr Tyr Lys Asp Asn Val
                100                 105                 110

Leu His Gly Asp Val Trp Ala Val Gly Val Asn Phe Pro Asn Gly
                115                 120                 125

Pro Val Met Lys Asn Glu Ile Val Met Glu Glu Pro Thr Glu Thr
130                 135                 140

Phe Thr Pro Lys Asn Gly Val Leu Val Gly Phe Cys Pro Lys Ala Tyr
145                 150                 155                 160

Leu Leu Lys Asp Gly Ser Tyr Tyr Gly Asn Met Thr Thr Phe Tyr
                165                 170                 175

Arg Ser Lys Lys Ser Gly Gln Ala Pro Pro Gly Tyr His Phe Val Lys
                180                 185                 190

His Arg Leu Val Lys Thr Asn Val Gly His Gly Phe Lys Thr Val Glu
                195                 200                 205

Gln Thr Glu Tyr Ala Thr Ala His Val Ser Asp Leu Pro Lys
210                 215                 220

<210> SEQ ID NO 56
<211> LENGTH: 221
<212> TYPE: PRT
<213> ORGANISM: Corynactis californica

<400> SEQUENCE: 56

Met Ser Leu Ser Lys Gln Val Val Lys Glu Asp Met Lys Met Thr Tyr
  1               5                  10                  15

His Met Asp Gly Cys Val Asn Gly His Tyr Phe Thr Ile Glu Gly Glu
                 20                  25                  30

Gly Thr Gly Lys Pro Phe Lys Gly Gln Lys Thr Leu Lys Leu Arg Val
             35                  40                  45

Thr Glu Gly Gly Pro Leu Pro Phe Ala Phe Asp Ile Leu Ser Ala Thr
 50                  55                  60

Phe Thr Tyr Gly Asn Arg Cys Phe Cys Asp Tyr Pro Glu Asp Met Pro
 65                  70                  75                  80

Asp Tyr Phe Lys Gln Ser Leu Pro Glu Gly Tyr Ser Trp Glu Arg Thr
                 85                  90                  95

Met Met Tyr Glu Asp Gly Ala Cys Gly Thr Ala Ser Ala His Ile Ser
                100                 105                 110

Leu Asp Lys Asn Gly Phe Val His Asn Ser Thr Phe His Gly Val Asn
                115                 120                 125

Phe Pro Ala Asn Gly Pro Val Met Lys Lys Lys Gly Val Asn Trp Glu
130                 135                 140

Pro Ser Ser Glu Lys Ile Thr Ala Cys Asp Gly Ile Leu Lys Gly Asp
145                 150                 155                 160

Val Thr Met Phe Leu Val Leu Glu Gly Gly His Arg Leu Lys Cys Leu
                165                 170                 175

Phe Gln Thr Thr Tyr Lys Ala Asp Lys Val Val Lys Met Pro Pro Asn
                180                 185                 190

His Ile Ile Glu His Arg Leu Val Arg Ser Glu Asp Gly Asp Ala Val
```

Gln Ile Gln Glu His Ala Val Ala Lys Tyr Phe Thr Val
        210             215                 220

<210> SEQ ID NO 57
<211> LENGTH: 227
<212> TYPE: PRT
<213> ORGANISM: Favia favus

<400> SEQUENCE: 57

Met Ser Val Ile Thr Ser Glu Met Lys Ile Glu Leu Arg Met Glu Gly
1               5                   10                  15

Ala Val Asn Gly His Lys Phe Val Ile Thr Gly Lys Gly Ser Gly Gln
            20                  25                  30

Pro Phe Glu Gly Ile Gln Asn Val Asp Leu Thr Val Ile Glu Gly Gly
        35                  40                  45

Pro Leu Pro Phe Ala Phe Asp Ile Leu Thr Thr Ala Phe His Tyr Gly
    50                  55                  60

Asn Arg Val Phe Val Glu Tyr Pro Glu Glu Ile Val Asp Tyr Phe Lys
65                  70                  75                  80

Gln Ser Phe Pro Glu Gly Tyr Ser Trp Glu Arg Ser Met Ser Tyr Glu
                85                  90                  95

Asp Gly Gly Ile Cys Leu Ala Thr Asn Asn Ile Thr Met Lys Lys Asp
            100                 105                 110

Gly Ser Asn Cys Phe Val Asn Glu Ile Arg Phe Asp Gly Val Asn Phe
        115                 120                 125

Pro Ala Asn Gly Pro Val Met Gln Arg Lys Thr Val Lys Trp Glu Pro
    130                 135                 140

Ser Thr Glu Lys Met Tyr Val Arg Asp Gly Val Leu Lys Gly Asp Val
145                 150                 155                 160

Asn Met Ala Leu Leu Leu Gln Gly Gly Gly His Tyr Arg Cys Asp Phe
                165                 170                 175

Arg Thr Thr Tyr Lys Ala Lys Lys Val Val Gln Leu Pro Asp Tyr His
            180                 185                 190

Phe Val Asp His Gln Met Glu Ile Thr Ser His Asp Lys Asp Tyr Asn
        195                 200                 205

Lys Val Lys Leu Tyr Glu His Ala Lys Ala His Ser Gly Leu Pro Arg
    210                 215                 220

Leu Ala Lys
225

<210> SEQ ID NO 58
<211> LENGTH: 217
<212> TYPE: PRT
<213> ORGANISM: Fungia concinna

<400> SEQUENCE: 58

Met Ser Val Ile Lys Pro Glu Met Lys Met Lys Tyr Phe Met Asp Gly
1               5                   10                  15

Ser Val Asn Gly His Glu Phe Thr Val Glu Gly Glu Gly Thr Gly Lys
            20                  25                  30

Pro Tyr Glu Gly His Gln Glu Met Thr Leu Arg Val Thr Met Ala Lys
        35                  40                  45

Gly Gly Pro Met Pro Phe Ser Phe Asp Leu Val Ser His Thr Phe Cys
    50                  55                  60

Tyr Gly His Arg Pro Phe Thr Lys Tyr Pro Glu Glu Ile Pro Asp Tyr
65                  70                  75                  80

```
Phe Lys Gln Ala Phe Pro Glu Gly Leu Ser Trp Glu Arg Ser Leu Gln
                85                  90                  95

Phe Glu Asp Gly Gly Phe Ala Ala Val Ser Ala His Ile Ser Leu Arg
            100                 105                 110

Gly Asn Cys Phe Glu His Lys Ser Lys Phe Val Gly Val Asn Phe Pro
            115                 120                 125

Ala Asp Gly Pro Val Met Gln Asn Gln Ser Ser Asp Trp Glu Pro Ser
130                 135                 140

Thr Glu Lys Ile Thr Thr Cys Asp Gly Val Leu Lys Gly Asp Val Thr
145                 150                 155                 160

Met Phe Leu Lys Leu Ala Gly Gly Asn His Lys Cys Gln Phe Lys
                165                 170                 175

Thr Thr Tyr Lys Ala Ala Lys Lys Ile Leu Lys Met Pro Gln Ser His
            180                 185                 190

Phe Ile Gly His Arg Leu Val Arg Lys Thr Glu Gly Asn Ile Thr Glu
            195                 200                 205

Leu Val Glu Asp Ala Val Ala His Cys
210                 215
```

<210> SEQ ID NO 59
<211> LENGTH: 225
<212> TYPE: PRT
<213> ORGANISM: Galaxea fascicularis

<400> SEQUENCE: 59

```
Met Ser Val Ile Lys Pro Glu Met Lys Ile Lys Leu Cys Met Arg Gly
1               5                   10                  15

Thr Val Asn Gly His Asn Phe Val Ile Glu Gly Glu Gly Lys Gly Asn
            20                  25                  30

Pro Tyr Glu Gly Thr Gln Ile Leu Asp Leu Asn Val Thr Glu Gly Ala
            35                  40                  45

Pro Leu Pro Phe Ala Tyr Asp Ile Leu Thr Thr Val Phe Gln Tyr Gly
50                  55                  60

Asn Arg Ala Phe Thr Lys Tyr Pro Ala Asp Ile Gln Asp Tyr Phe Lys
65                  70                  75                  80

Gln Thr Phe Pro Glu Gly Tyr His Trp Glu Arg Ser Met Thr Tyr Glu
                85                  90                  95

Asp Gln Gly Ile Cys Thr Ala Thr Ser Asn Ile Ser Met Arg Gly Asp
            100                 105                 110

Cys Phe Phe Tyr Asp Ile Arg Phe Asp Gly Val Asn Phe Pro Pro Asn
            115                 120                 125

Gly Pro Val Met Gln Lys Lys Thr Leu Lys Trp Glu Pro Ser Thr Glu
130                 135                 140

Lys Met Tyr Val Arg Asp Gly Val Leu Lys Gly Asp Val Asn Met Ala
145                 150                 155                 160

Leu Leu Leu Glu Gly Gly Gly His Tyr Arg Cys Asp Phe Lys Thr Thr
                165                 170                 175

Tyr Lys Ala Lys Lys Asp Val Arg Leu Pro Asp Tyr His Phe Val Asp
            180                 185                 190

His Arg Ile Glu Ile Leu Lys His Asp Lys Asp Tyr Asn Lys Val Lys
            195                 200                 205

Leu Tyr Glu Asn Ala Val Ala Arg Tyr Ser Met Leu Pro Ser Gln Ala
210                 215                 220

Lys
225
```

<210> SEQ ID NO 60
<211> LENGTH: 221
<212> TYPE: PRT
<213> ORGANISM: Goniopora tenuidens

<400> SEQUENCE: 60

Met Ser Val Ile Ala Lys Gln Met Thr Tyr Lys Val Tyr Met Ser Gly
1               5                   10                  15

Thr Val Asn Gly His Tyr Phe Glu Val Gln Gly Asp Gly Lys Gly Lys
            20                  25                  30

Pro Tyr Glu Gly Glu Gln Thr Val Lys Leu Thr Val Thr Lys Gly Gly
        35                  40                  45

Pro Leu Pro Phe Ala Trp Asp Ile Leu Ser Pro Gln Ser Gln Tyr Gly
    50                  55                  60

Ser Ile Pro Phe Thr Lys Tyr Pro Glu Asp Ile Pro Asp Tyr Val Lys
65                  70                  75                  80

Gln Ser Phe Pro Glu Gly Tyr Thr Trp Glu Arg Ile Met Asn Phe Glu
                85                  90                  95

Asp Gly Ala Val Cys Thr Val Ser Asn Asp Ser Ser Ile Gln Gly Asn
            100                 105                 110

Cys Phe Ile Tyr Asn Val Lys Phe Ser Gly Leu Asn Phe Pro Pro Asn
        115                 120                 125

Gly Pro Val Met Gln Lys Lys Thr Gln Gly Trp Glu Pro Asn Thr Glu
    130                 135                 140

Arg Leu Phe Ala Arg Asp Gly Met Leu Ile Gly Asn Asn Phe Met Ala
145                 150                 155                 160

Leu Lys Leu Glu Gly Gly Gly His Tyr Leu Cys Glu Phe Lys Ser Thr
                165                 170                 175

Tyr Lys Ala Lys Lys Pro Val Lys Met Pro Gly Tyr His Tyr Val Asp
            180                 185                 190

Arg Lys Leu Asp Val Thr Asn His Asn Ile Asp Tyr Thr Ser Val Glu
        195                 200                 205

Gln Cys Glu Ile Ser Ile Ala Arg Lys Pro Val Val Ala
    210                 215                 220

<210> SEQ ID NO 61
<211> LENGTH: 227
<212> TYPE: PRT
<213> ORGANISM: Heteractis crispa

<400> SEQUENCE: 61

Met Ala Gly Leu Leu Lys Glu Ser Met Arg Ile Lys Met Tyr Met Glu
1               5                   10                  15

Gly Thr Val Asn Gly His Tyr Phe Lys Cys Glu Gly Glu Gly Asp Gly
            20                  25                  30

Asn Pro Phe Thr Gly Thr Gln Ser Met Arg Ile His Val Thr Glu Gly
        35                  40                  45

Ala Pro Leu Pro Phe Ala Phe Asp Ile Leu Ala Pro Cys Cys Glu Tyr
    50                  55                  60

Gly Ser Arg Thr Phe Val His His Thr Ala Glu Ile Pro Asp Phe Phe
65                  70                  75                  80

Lys Gln Ser Phe Pro Glu Gly Phe Thr Trp Glu Arg Thr Thr Thr Tyr
                85                  90                  95

Glu Asp Gly Gly Ile Leu Thr Ala His Gln Asp Thr Ser Leu Glu Gly
            100                 105                 110

```
Asn Cys Leu Ile Tyr Lys Val Lys Val Leu Gly Thr Asn Phe Pro Ala
            115                 120                 125
Asp Gly Pro Val Met Lys Asn Lys Ser Gly Gly Trp Glu Pro Cys Thr
    130                 135                 140
Glu Val Val Tyr Pro Glu Asn Gly Val Leu Cys Gly Arg Asn Val Met
145                 150                 155                 160
Ala Leu Lys Val Gly Asp Arg Arg Leu Ile Cys His Leu Tyr Thr Ser
                165                 170                 175
Tyr Arg Ser Lys Lys Ala Val Arg Ala Leu Thr Met Pro Gly Phe His
                180                 185                 190
Phe Thr Asp Ile Arg Leu Gln Met Pro Arg Lys Lys Asp Glu Tyr
            195                 200                 205
Phe Glu Leu Tyr Glu Ala Ser Val Ala Arg Tyr Ser Asp Leu Pro Glu
210                 215                 220
Lys Ala Asn
225

<210> SEQ ID NO 62
<211> LENGTH: 222
<212> TYPE: PRT
<213> ORGANISM: Labidocera aestiva

<400> SEQUENCE: 62

Met Pro Val Met Lys Ile Glu Cys Arg Ile Ser Gly Thr Met Asn Gly
1               5                   10                  15
Glu Glu Phe Glu Leu Val Gly Ala Gly Asp Gly Asn Thr Asp Glu Gly
                20                  25                  30
Arg Met Thr Asn Lys Met Lys Ser Thr Lys Gly Pro Leu Ser Phe Ser
            35                  40                  45
Pro Tyr Leu Leu Ser His Ile Met Gly Tyr Gly Phe Tyr His Tyr Ala
        50                  55                  60
Thr Phe Pro Ala Gly Tyr Glu Asn Val Tyr Leu His Ala Ala Lys Asn
65                  70                  75                  80
Gly Gly Tyr Thr Asn Thr Arg Thr Glu Arg Tyr Glu Asp Gly Gly Ile
                85                  90                  95
Ile Ser Val Asn Phe Thr Tyr Arg Tyr Glu Gly Asn Lys Val Ile Gly
                100                 105                 110
Asp Phe Lys Val Val Gly Ser Gly Phe Pro Ala Asn Ser Val Ile Phe
            115                 120                 125
Thr Asp Lys Ile Ile Lys Ser Asn Pro Thr Cys Glu His Ile Tyr Pro
    130                 135                 140
Lys Gly Asp Asn Ile Leu Val Asn Ala Tyr Thr Arg Thr Trp Met Leu
145                 150                 155                 160
Arg Asp Gly Gly Tyr Tyr Ser Ala Gln Val Asn Asn His Leu His Phe
                165                 170                 175
Lys Thr Ala Met His Pro Thr Met Leu Gln Asn Gly Ser Met Phe
                180                 185                 190
Thr Tyr Arg Lys Val Glu Glu Leu His Ser Gln Ser Asp Val Gly Ile
            195                 200                 205
Val Glu Tyr Gln His Val Phe Lys Thr Pro Thr Ala Phe Ala
210                 215                 220

<210> SEQ ID NO 63
<211> LENGTH: 226
<212> TYPE: PRT
<213> ORGANISM: Lobophyllia hemprichii
```

<400> SEQUENCE: 63

```
Met Ser Ala Ile Lys Pro Asp Met Lys Ile Asn Leu Arg Met Glu Gly
1               5                   10                  15

Asn Val Asn Gly His His Phe Val Ile Asp Gly Asp Gly Thr Gly Lys
            20                  25                  30

Pro Phe Glu Gly Lys Gln Ser Met Asp Leu Glu Val Lys Glu Gly Gly
        35                  40                  45

Pro Leu Pro Phe Ala Phe Asp Ile Leu Thr Thr Ala Phe His Tyr Gly
    50                  55                  60

Asn Arg Val Phe Ala Glu Tyr Pro Asp His Ile Gln Asp Tyr Phe Lys
65                  70                  75                  80

Gln Ser Phe Pro Lys Gly Tyr Ser Trp Glu Arg Ser Leu Thr Phe Glu
                85                  90                  95

Asp Gly Gly Ile Cys Ile Ala Arg Asn Asp Ile Thr Met Glu Gly Asp
            100                 105                 110

Thr Phe Tyr Asn Lys Val Arg Phe His Gly Val Asn Phe Pro Ala Asn
        115                 120                 125

Gly Pro Val Met Gln Lys Lys Thr Leu Lys Trp Glu Pro Ser Thr Glu
    130                 135                 140

Lys Met Tyr Val Arg Asp Gly Val Leu Thr Gly Asp Ile Thr Met Ala
145                 150                 155                 160

Leu Leu Leu Glu Gly Asn Ala His Tyr Arg Cys Asp Phe Arg Thr Thr
                165                 170                 175

Tyr Lys Ala Lys Glu Lys Gly Val Lys Leu Pro Gly Tyr His Phe Val
            180                 185                 190

Asp His Cys Ile Glu Ile Leu Ser His Asp Lys Asp Tyr Asn Lys Val
        195                 200                 205

Lys Leu Tyr Glu His Ala Val Ala His Ser Gly Leu Pro Asp Asn Ala
    210                 215                 220

Arg Arg
225
```

<210> SEQ ID NO 64
<211> LENGTH: 214
<212> TYPE: PRT
<213> ORGANISM: Meandrina meandrites

<400> SEQUENCE: 64

```
Met Ala Val Pro Thr Gln Val Lys Met Lys Tyr Ser Met Asp Gly Asn
1               5                   10                  15

Phe Asn Gly Gln Ser Phe Thr Val Val Gly Glu Gly Thr Gly Asn Pro
            20                  25                  30

Tyr Glu Gly His Gln Ser Leu Lys Leu Thr Val Lys Gly Glu Pro Leu
        35                  40                  45

Pro Phe Ala Phe Asp Ile Leu Ser Ala Thr Phe Thr Tyr Gly Asn Arg
    50                  55                  60

Val Phe Thr Lys Tyr Pro Glu Gly Lys Thr Asp Tyr Phe Lys Glu Ala
65                  70                  75                  80

Phe Pro Gly Gly Leu Thr Trp Glu Arg Thr Met Thr Phe Glu Asp Gly
                85                  90                  95

Gly Ile Cys Thr Val Ala Ala Glu Ile Ser Leu Thr Gly Ser Val Phe
            100                 105                 110

Glu His Lys Ser Lys Phe Val Gly Val Asn Phe Pro Ala Asn Gly Pro
        115                 120                 125

Val Ile Gln Lys Lys Thr Leu Gly Trp Glu Thr Ser Thr Glu Lys Met
```

```
                130                 135                 140
Ala Ala Asn Asp Gly Ser Val Gln Gly Tyr Asp Thr Met Phe Leu Lys
145                 150                 155                 160

Leu Glu Gly Gly Gly Arg His Lys Cys Tyr Phe Val Thr Asn His Lys
                165                 170                 175

Ala Lys Arg Ala Val Lys Val Pro Asp Asn His Phe Val Trp His Arg
                180                 185                 190

Leu Val Arg Asn Gly Asp Gly Asn Thr Val Glu Leu Glu Glu Thr Ala
                195                 200                 205

Glu Ala Arg Tyr Asp Ser
            210

<210> SEQ ID NO 65
<211> LENGTH: 225
<212> TYPE: PRT
<213> ORGANISM: Montastraea cavernosa

<400> SEQUENCE: 65

Met Ser Val Ile Lys Pro Ile Met Glu Ile Lys Leu Arg Met Gln Gly
1               5                   10                  15

Val Val Asn Gly His Lys Phe Val Ile Lys Gly Glu Gly Glu Gly Lys
                20                  25                  30

Pro Phe Glu Gly Thr Gln Thr Ile Asn Leu Thr Val Lys Glu Gly Ala
            35                  40                  45

Pro Leu Pro Phe Ala Tyr Asp Ile Leu Thr Ser Ala Phe Gln Tyr Gly
        50                  55                  60

Asn Arg Val Phe Thr Lys Tyr Pro Asp Asp Ile Pro Asp Tyr Phe Lys
65                  70                  75                  80

Gln Thr Phe Pro Glu Gly Tyr Ser Trp Glu Arg Ile Met Ala Tyr Glu
                85                  90                  95

Asp Gln Ser Ile Cys Thr Ala Thr Ser Asp Ile Lys Met Glu Gly Asp
            100                 105                 110

Cys Phe Ile Tyr Glu Ile Gln Phe His Gly Val Asn Phe Pro Pro Asn
        115                 120                 125

Gly Pro Val Met Gln Lys Lys Thr Leu Lys Trp Glu Pro Ser Thr Glu
130                 135                 140

Lys Met Tyr Val Arg Asp Gly Val Leu Lys Gly Asp Val Asn Met Ala
145                 150                 155                 160

Leu Leu Leu Glu Gly Gly Gly His Tyr Arg Cys Asp Phe Arg Ser Thr
                165                 170                 175

Tyr Lys Ala Lys Lys Arg Val Gln Leu Pro Asp Tyr His Phe Val Asp
                180                 185                 190

His Arg Ile Glu Ile Leu Ser His Asp Asn Asp Tyr Asn Thr Val Lys
            195                 200                 205

Leu Ser Glu Asp Ala Glu Ala Arg Tyr Ser Met Leu Pro Ser Gln Ala
        210                 215                 220

Lys
225

<210> SEQ ID NO 66
<211> LENGTH: 234
<212> TYPE: PRT
<213> ORGANISM: Phialidium sp

<400> SEQUENCE: 66

Met Ser Ser Gly Ala Leu Leu Phe His Gly Lys Ile Pro Tyr Val Val
1               5                   10                  15
```

Glu Met Glu Gly Asn Val Asp Gly His Thr Phe Ser Ile Arg Gly Lys
            20                  25                  30

Gly Tyr Gly Asp Ala Ser Val Gly Lys Val Asp Ala Gln Phe Ile Cys
        35                  40                  45

Thr Thr Gly Asp Val Pro Val Pro Trp Ser Thr Leu Val Thr Thr Leu
    50                  55                  60

Thr Tyr Gly Ala Gln Cys Phe Ala Lys Tyr Gly Pro Glu Leu Lys Asp
65                  70                  75                  80

Phe Tyr Lys Ser Cys Met Pro Glu Gly Tyr Val Gln Glu Arg Thr Ile
                85                  90                  95

Thr Phe Glu Gly Asp Gly Val Phe Lys Thr Arg Ala Glu Val Thr Phe
                100                 105                 110

Glu Asn Gly Ser Val Tyr Asn Arg Val Lys Leu Asn Gly Gln Gly Phe
            115                 120                 125

Lys Lys Asp Gly His Val Leu Gly Lys Asn Leu Glu Phe Asn Phe Thr
130                 135                 140

Pro His Cys Leu Tyr Ile Trp Gly Asp Gln Ala Asn His Gly Leu Lys
145                 150                 155                 160

Ser Ala Phe Lys Ile Met His Glu Ile Thr Gly Ser Lys Glu Asp Phe
                165                 170                 175

Ile Val Ala Asp His Thr Gln Met Asn Thr Pro Ile Gly Gly Gly Pro
            180                 185                 190

Val His Val Pro Glu Tyr His His Ile Thr Tyr His Val Thr Leu Ser
        195                 200                 205

Lys Asp Val Thr Asp His Arg Asp Asn Met Ser Leu Val Glu Thr Val
210                 215                 220

Arg Ala Val Asp Cys Arg Lys Thr Tyr Leu
225                 230

<210> SEQ ID NO 67
<211> LENGTH: 222
<212> TYPE: PRT
<213> ORGANISM: Pocillopora damicornis

<400> SEQUENCE: 67

Met Ser Leu Ser Lys Gln Val Ile Leu Lys Asp Met Asn Leu Lys Phe
1               5                   10                  15

Glu Met Lys Gly Ser Val Asn Gly His Tyr Phe Glu Ile Glu Gly Glu
            20                  25                  30

Gly Arg Gly Lys Pro Tyr Glu Gly Val Gln Lys Ser Thr Phe Trp Val
        35                  40                  45

Thr Lys Gly Gly Pro Leu Pro Phe Ser Phe Asp Ile Leu Ser Ser Ala
    50                  55                  60

Phe Lys Tyr Gly Asn Arg Cys Phe Thr Lys Tyr Pro Ala Asp Met Pro
65                  70                  75                  80

Asp Tyr Phe Lys Glu Ala Phe Pro Ala Gly Met Ser Phe Glu Arg Thr
                85                  90                  95

Phe Thr Phe Glu Asp Gly Gly Val Ala Thr Ala Ser Gly His Ile Cys
                100                 105                 110

Leu Glu Gly Asn Trp Phe Lys His Thr Ser Met Phe His Gly Val Asn
            115                 120                 125

Phe Pro Ala Asn Gly Pro Ile Met Gln Lys Arg Thr Ile Gly Trp Asp
130                 135                 140

Pro Ser Phe Glu Lys Met Thr Val Ser Asn Asn Ile Leu Arg Gly Asp
145                 150                 155                 160

```
Val Thr Met Phe Leu Gln Leu Lys Gly Gly Tyr His Ser Cys Gln
                165                 170                 175

Phe His Thr Ser Tyr Lys Thr Lys Glu Pro Val Thr Leu Pro Gln Asn
            180                 185                 190

His Val Val Glu His Arg Ile Thr Arg Thr Asp Ile Glu Asp Lys Lys
            195                 200                 205

Val Leu Leu Glu Glu Thr Ala Val Ala His Val Asn Pro Leu
    210                 215                 220

<210> SEQ ID NO 68
<211> LENGTH: 222
<212> TYPE: PRT
<213> ORGANISM: Pontellina plumata

<400> SEQUENCE: 68

Met Pro Ala Met Lys Ile Glu Cys Arg Ile Ser Gly Thr Leu Asn Gly
1               5                   10                  15

Val Val Phe Glu Leu Val Gly Gly Glu Gly Ile Pro Glu Gln Gly
            20                  25                  30

Arg Met Thr Asn Lys Met Lys Ser Thr Lys Gly Ala Leu Thr Phe Ser
        35                  40                  45

Pro Tyr Leu Leu Ser His Val Met Gly Tyr Gly Phe Tyr His Phe Gly
    50                  55                  60

Thr Tyr Pro Ser Gly Tyr Glu Asn Pro Phe Leu His Ala Ala Asn Asn
65                  70                  75                  80

Gly Gly Tyr Thr Asn Thr Arg Ile Glu Lys Tyr Glu Asp Gly Gly Val
                85                  90                  95

Leu His Val Ser Phe Ser Tyr Arg Tyr Glu Ala Gly Arg Val Ile Gly
            100                 105                 110

Asp Phe Lys Val Val Gly Thr Gly Phe Pro Glu Asp Ser Val Ile Phe
        115                 120                 125

Thr Asp Lys Ile Ile Arg Ser Asn Ala Thr Val Glu His Leu His Pro
    130                 135                 140

Met Gly Asp Asn Val Leu Val Gly Ser Phe Ala Arg Thr Phe Ser Leu
145                 150                 155                 160

Arg Asp Gly Gly Tyr Tyr Ser Phe Val Val Asp Ser His Met His Phe
                165                 170                 175

Lys Ser Ala Ile His Pro Ser Ile Leu Gln Asn Gly Gly Ser Met Phe
            180                 185                 190

Ala Phe Arg Arg Val Glu Glu Leu His Ser Asn Thr Glu Leu Gly Ile
        195                 200                 205

Val Glu Tyr Gln His Ala Phe Lys Thr Pro Thr Ala Phe Ala
    210                 215                 220

<210> SEQ ID NO 69
<211> LENGTH: 231
<212> TYPE: PRT
<213> ORGANISM: Ricordea florida

<400> SEQUENCE: 69

Met Ser Ala Leu Lys Glu Glu Met Lys Ile Lys Leu Lys Met Val Gly
1               5                   10                  15

Val Val Asn Gly Gln Ser Phe Gln Ile Asp Gly Glu Gly Lys Gly Lys
            20                  25                  30

Pro Tyr Glu Gly Ser Gln Lys Leu Thr Leu Glu Val Val Glu Gly Gly
        35                  40                  45
```

```
Pro Leu Leu Phe Ser Tyr Asp Ile Leu Thr Thr Ile Phe Gln Tyr Gly
     50                  55                  60

Asn Arg Ala Phe Val Asn Tyr Pro Lys Asp Ile Pro Asp Ile Phe Lys
 65                  70                  75                  80

Gln Thr Cys Ser Gly Pro Asp Gly Gly Phe Ser Trp Gln Arg Thr Met
                 85                  90                  95

Thr Tyr Glu Asp Gly Gly Val Cys Thr Ala Ser Asn His Ile Ser Val
            100                 105                 110

Asp Gly Asp Thr Phe Tyr Tyr Val Ile Arg Phe Asn Gly Glu Asn Phe
        115                 120                 125

Pro Pro Asn Gly Pro Val Met Gln Lys Arg Thr Val Lys Trp Glu Pro
    130                 135                 140

Ser Thr Glu Ile Met Phe Glu Arg Asp Gly Leu Leu Arg Gly Asp Ile
145                 150                 155                 160

Ala Met Ser Leu Leu Lys Gly Gly Gly His Tyr Arg Cys Asp Phe
                165                 170                 175

Lys Thr Ile Tyr Thr Pro Lys Arg Lys Val Asn Met Pro Gly Tyr His
                180                 185                 190

Phe Val Asp His Cys Ile Glu Ile Gln Lys His Asp Lys Asp Tyr Asn
                195                 200                 205

Met Ala Val Leu Ser Glu Asp Ala Val Ala His Asn Ser Pro Leu Glu
    210                 215                 220

Lys Lys Ser Gln Ala Lys Ala
225                 230

<210> SEQ ID NO 70
<211> LENGTH: 225
<212> TYPE: PRT
<213> ORGANISM: Trachyphyllia geoffroyi

<400> SEQUENCE: 70

Met Ser Leu Ile Lys Pro Glu Met Lys Ile Lys Leu Leu Met Glu Gly
 1                5                  10                  15

Asn Val Asn Gly His Gln Phe Val Ile Glu Gly Asp Gly Lys Gly His
             20                  25                  30

Pro Phe Glu Gly Lys Gln Ser Met Asp Leu Val Val Lys Glu Gly Ala
         35                  40                  45

Pro Leu Pro Phe Ala Tyr Asp Ile Leu Thr Thr Ala Phe His Tyr Gly
     50                  55                  60

Asn Arg Val Phe Ala Lys Tyr Pro Asp His Ile Pro Asp Tyr Phe Lys
 65                  70                  75                  80

Gln Ser Phe Pro Lys Gly Phe Ser Trp Glu Arg Ser Leu Met Phe Glu
                 85                  90                  95

Asp Gly Gly Val Cys Ile Ala Thr Asn Asp Ile Thr Leu Lys Gly Asp
            100                 105                 110

Thr Phe Phe Asn Lys Val Arg Phe Asp Gly Val Asn Phe Pro Pro Asn
        115                 120                 125

Gly Pro Val Met Gln Lys Lys Thr Leu Lys Trp Glu Ala Ser Thr Glu
    130                 135                 140

Lys Met Tyr Leu Arg Asp Gly Val Leu Thr Gly Asp Ile Thr Met Ala
145                 150                 155                 160

Leu Leu Leu Lys Gly Asp Val His Tyr Arg Cys Asp Phe Arg Thr Thr
                165                 170                 175

Tyr Lys Ser Arg Gln Glu Gly Val Lys Leu Pro Gly Tyr His Phe Val
                180                 185                 190
```

-continued

```
Asp His Cys Ile Ser Ile Leu Arg His Asp Lys Asp Tyr Asn Glu Val
        195                 200                 205

Lys Leu Tyr Glu His Ala Val Ala His Ser Gly Leu Pro Asp Asn Val
        210                 215                 220

Lys
225

<210> SEQ ID NO 71
<211> LENGTH: 225
<212> TYPE: PRT
<213> ORGANISM: Artificial Sequence
<220> FEATURE:
<223> OTHER INFORMATION: Description of Artifical Sequence: amino acid
      sequence is identical to residues 1 to 225 of amino acid sequence
      accorded Genbank No. ABC68474

<400> SEQUENCE: 71

Met Arg Ser Ser Lys Asn Val Ile Lys Glu Phe Met Arg Phe Lys Val
1               5                   10                  15

Arg Met Glu Gly Thr Val Asn Gly His Glu Phe Glu Ile Glu Gly Glu
                20                  25                  30

Gly Glu Gly Arg Pro Tyr Glu Gly His Asn Thr Val Lys Leu Lys Val
            35                  40                  45

Thr Lys Gly Gly Pro Leu Pro Phe Ala Trp Asp Ile Leu Ser Pro Gln
    50                  55                  60

Phe Gln Tyr Gly Ser Lys Val Tyr Val Lys His Pro Ala Asp Ile Pro
65                  70                  75                  80

Asp Tyr Lys Lys Leu Ser Phe Pro Glu Gly Phe Lys Trp Glu Arg Val
                85                  90                  95

Met Asn Phe Glu Asp Gly Gly Val Val Thr Val Thr Gln Asp Pro Ser
                100                 105                 110

Leu Gln Asp Gly Cys Phe Ile Tyr Lys Val Lys Phe Ile Gly Val Asn
            115                 120                 125

Phe Pro Ser Asp Gly Pro Val Met Gln Lys Lys Thr Met Gly Trp Glu
    130                 135                 140

Ala Ser Thr Glu Arg Leu Tyr Pro Arg Asp Gly Val Leu Lys Gly Glu
145                 150                 155                 160

Ile His Lys Ala Leu Lys Leu Lys Asp Gly Gly His Tyr Leu Val Glu
                165                 170                 175

Phe Lys Thr Ile Tyr Met Ala Lys Lys Pro Val Gln Leu Pro Gly Tyr
                180                 185                 190

Tyr Tyr Val Asp Ser Lys Leu Asp Ile Thr Ser His Asn Lys Asp Tyr
            195                 200                 205

Thr Ile Val Glu Gln Tyr Glu Arg Thr Glu Gly Arg His His Leu Phe
    210                 215                 220

Leu
225
```

ISOLATED AUSTRALIAN CORAL REEF FLUORESCENT PROTEINS AND CELL-BASED KINASE OR PHOSPHATASE PLATFORMS FOR CANCER DRUG DEVELOPMENT

CROSS-REFERENCE TO RELATED APPLICATIONS

This application claims the benefit of priority of i) U.S. Provisional Application No. 61/243,024, filed on Sep. 16, 2009; and ii) U.S. Provisional Application No. 61/350,630, filed on Jun. 2, 2010, the entire content of each of which is incorporated herein by reference.

SEQUENCE LISTING

The instant application contains a Sequence Listing which has been submitted in ASCII format via EFS-Web and is hereby incorporated by reference in its entirety. Said ASCII copy, created on Sep. 18, 2010, is named 26228PCT.txt and is 100,737 bytes in size.

FIELD OF THE DISCLOSURE

Generally disclosed are isolated fluorescent proteins from organisms of the order Scleractinia, and variants of such proteins. Further disclosed are methods of using and making the disclosed proteins and variants thereof, as well as kits for performing the methods. Additionally disclosed are cell-based assays for detecting kinase and phosphatase activities and for identifying kinase and phosphatase modulators by utilizing a fluorescent protein disclosed herein.

BACKGROUND OF THE DISCLOSURE

Fluorescent proteins are proteins that absorb electromagnetic radiation of a particular wavelength and emit electromagnetic radiation of a different longer wavelength. The marine organisms that express fluorescent proteins are predominantly within the phylum *Cnidaria*, and are estimated to have evolved over 700 million years ago, before organisms of the phylum *Cnidaria* and the *bilateria* separated (Shagin et al. (2004), *Mol. Biol. Evol.* 21, pp. 841-850). Fluorescent proteins exhibit a wide diversity of excitation/emission spectra that extend from cyan to far red, but are generally grouped according to four basic colors: three fluorescent colors (cyan, green, and red) and a non-fluorescent color (purple-blue) (Kelmanson and Matz (2003), *Mol. Biol. Evol.* 20, pp. 1125-1133). Single organisms have been shown to express multiple fluorescent protein genes, to emit a variety of fluorescent colors (Kelmanson and Matz (2003), *Mol. Biol. Evol.* 20, pp. 1125-1133; Kao et al. (2007), *Mar. Biotechnol.* (NY) 9, pp. 733-746), and to express fluorescent proteins in distinct anatomical patterns (Gruber et al. (2008), *Biol. Bull.* 215, pp. 143-154).

The identification and isolation of fluorescent proteins in various organisms, including marine organisms, has provided a valuable tool to molecular biology. The green fluorescent protein (GFP) of the jellyfish *Aequorea Victoria* (*A. victoria*), for example, has become a commonly used reporter molecule for examining various cellular processes, including the regulation of gene expression, the localization and interactions of cellular proteins, the pH of intracellular compartments, and the activities of enzymes (see, e.g., U.S. Pat. Nos. 5,491,084, 5,777,079, and 7,329,735).

The usefulness of *A. victoria* GFP has led to the identification of numerous other fluorescent proteins, such as fluorescent proteins with emission wavelengths or brightness different from that of GFP. In addition, spectral variants of *A. victoria* GFP have been disclosed that are excited or emit at wavelengths, for different periods of time, and under different conditions in comparison to the respective properties of native GFP.

Although a number of fluorescent proteins have been disclosed, there still exists a need for fluorescent proteins that exhibit unique biochemical properties. For example, a fluorescent protein that fluoresces with a greater intensity than those previously disclosed would be beneficial, inter alia, in the fields of molecular biology, biochemistry, and drug discovery. Additionally, fluorescent proteins that can detect the interaction of specific molecules and that can track the intra- and intercellular movements of specific molecules would be beneficial, inter alia, in the fields of molecular biology, biochemistry, and drug discovery.

A hallmark of cancer is the imbalance between protein kinase and phosphatase activity. In many cases, overactive protein kinases drive the uncontrolled proliferation of tumors. Akt1 kinase is a well studied kinase that promotes angiogenesis and the development of new blood vessels that feed the uncontrolled growth of solid tumors. Akt1 kinase has several established inhibitors that have shown great potential in retarding the growth of tumors.

Over the past decade, several inhibitors have been identified that target specific protein kinases, and these inhibitors have been developed into highly effective anti-cancer agents. One such example is imatinib mesylate (Gleevec®), a tyrosine kinase inhibitor marketed by Novartis that successfully treats chronic myeloid leukemia and generates over $3.7 billion/year in revenue. There has been great difficulty in finding selective kinase inhibitors, and presently fewer than 15 have been approved by the FDA.

SUMMARY OF THE DISCLOSURE

Disclosed herein are fluorescent proteins isolated from organisms of the order Scleractina, and variants of such proteins.

In one embodiment, an isolated fluorescent polypeptide is provided, which comprises an amino acid sequence selected from the group consisting of SEQ ID NOs: 10, 12, 14, 16, 18, 20, 22, 24, 26, 28, 30, 32, 34, 36, 38, 40, 42, and 44.

In another embodiment, an isolated fluorescent polypeptide variant is provided, wherein the fluorescent polypeptide variant comprises an amino acid sequence having at least 80% sequence identity to an amino acid sequence selected from the group consisting of SEQ ID NOs: 10, 12, 14, 16, 18, 20, 22, 24, 26, 28, 30, 32, 34, 36, 38, 40, 42, and 44.

In yet another embodiment, an isolated nucleic acid encoding for a fluorescent protein is provided. The nucleic acid comprises a nucleotide sequence selected from the group consisting of SEQ ID NOs: 11, 13, 15, 17, 19, 21, 23, 25, 27, 29, 31, 33, 35, 37, 39, 41, 43, and 45. In a further embodiment, the nucleic acid comprises a codon-usage variant of a nucleotide sequence selected from the group consisting of SEQ ID NOs: 11, 13, 15, 17, 19, 21, 23, 25, 27, 29, 31, 33, 35, 37, 39, 41, 43, and 45. In this embodiment, the variant nucleotide sequence of the nucleic acid differs from the nucleotide sequence of the reference nucleic acid, but each nucleotide sequence nevertheless encodes a polypeptide comprising the same amino acid sequence.

In still another embodiment, an isolated nucleic acid encoding for a fluorescent protein is provided, wherein the nucleic acid comprises a nucleotide sequence having at least 80% sequence identity to a nucleotide sequence selected from the group consisting of SEQ ID NOs: 11, 13, 15, 17, 19, 21, 23, 25, 27, 29, 31, 33, 35, 37, 39, 41, 43, and 45. In a further embodiment, the nucleic acid comprises a codon-usage variant of a nucleotide sequence having at least 80% sequence identity to a nucleotide sequence selected from the group consisting of SEQ ID NOs: 11, 13, 15, 17, 19, 21, 23, 25, 27, 29, 31, 33, 35, 37, 39, 41, 43, and 45. In this embodiment, the variant nucleotide sequence of the nucleic acid differs from the nucleotide sequence of the reference nucleic acid, but each nucleotide sequence nevertheless encodes a polypeptide comprising the same amino acid sequence.

In another embodiment, the present invention provides fusion proteins comprising a protein of interest operatively joined to at least one fluorescent protein of the invention, or variant thereof (e.g., a protein comprising the amino acid sequence of any of SEQ ID NOs: 10, 12, 14, 16, 18, 20, 22, 24, 26, 28, 30, 32, 34, 36, 38, 40, 42 and 44, or a sequence that has at least 80% sequence identity to any of these sequences). In some embodiments, the fusion protein contains an epitope tag, such as a polyhistine tag.

In still another embodiment, nucleic acid molecules encoding a fusion protein are provided. In some such embodiments, a nucleotide sequence encoding a protein of interest is operatively linked to a nucleotide sequence selected from the group consisting of SEQ ID NOs: 11, 13, 15, 17, 19, 21, 23, 25, 27, 29, 31, 33, 35, 37, 39, 41, 43, and 45. In other such embodiments, a nucleotide sequence encoding a protein of interest is operatively linked to a nucleotide sequence having at least 80% sequence identity to a nucleotide sequence selected from the group consisting of SEQ ID NOs: 11, 13, 15, 17, 19, 21, 23, 25, 27, 29, 31, 33, 35, 37, 39, 41, 43, and 45. In still other such embodiments, a nucleotide sequence encoding a protein of interest is operatively linked to a codon-usage variant of a nucleotide sequence having at least 80% sequence identity to a nucleotide sequence selected from the group consisting of SEQ ID NOs: 11, 13, 15, 17, 19, 21, 23, 25, 27, 29, 31, 33, 35, 37, 39, 41, 43, and 45. In these still other such embodiments, the variant nucleotide sequence of the nucleic acid differs from the nucleotide sequence of the reference nucleic acid, but each of the variant nucleotide sequence and the nucleotide sequence of the reference nucleic acid nevertheless encode a polypeptide comprising the same amino acid sequence.

In one embodiment, the present invention provides vectors that encode the fluorescent protein variants disclosed herein, as well as host cells containing such vectors. The invention also provides expression vectors suitable for the expression of the disclosed fluorescent polypeptides, fluorescent polypeptide variants, or fusion proteins, as well as host cells containing such expression vectors.

As further disclosed herein, the fluorescent protein variants of the invention can be used in various applications.

In one embodiment, the invention provides a method for detecting transcriptional activity, where the method utilizes a host cell comprising a vector encoding a fluorescent protein comprising the amino acid sequence of any of SEQ ID NOs: 10, 12, 14, 16, 18, 20, 22, 24, 26, 28, 30, 32, 34, 36, 38, 40, 42 and 44, operably linked to at least one expression control sequence, and a means to detecting fluorescence. In this method, assaying the fluorescence of the fluorescent protein produced by the host cell is indicative of transcriptional activity.

In one embodiment, the present invention is directed to a kit for the detection of protein-protein interactions. The kit comprises an isolated fluorescent polypeptide comprising an amino acid sequence selected from the group consisting of SEQ ID NOs: 10, 12, 14, 16, 18, 20, 22, 24, 26, 28, 30, 32, 34, 36, 38, 40, 42 and 44, or a variant thereof.

In other embodiments, the invention also provides a polypeptide probe suitable for use in fluorescence resonance energy transfer (FRET), comprising at least one fluorescent protein variant of the invention.

In a further embodiment, the present invention is directed to a novel FRET pair. The novel FRET pair comprises an isolated fluorescent polypeptide which comprises an amino acid sequence selected from the group consisting of SEQ ID NOs: 10, 12, 14, 16, 18, 20, 22, 24, 26, 28, 30, 32, 34, 36, 38, 40, 42 and 44. In still another embodiment, the FRET pair comprises a polypeptide having an amino acid sequence with at least 80% sequence identity to any of SEQ ID NOs: 10, 12, 14, 16, 18, 20, 22, 24, 26, 28, 30, 32, 34, 36, 38, 40, 42 or 44.

In another embodiment, the present invention provides fluorescent proteins having an increased intensity of emission with respect to fluorescent proteins known in the art.

In still another embodiment, the invention provides a method for the analysis of in vivo localization or trafficking of a polypeptide of interest, where the method uses a fluorescent fusion protein of the invention in a host cell or tissue, and where the fusion protein can be visualized in the host cell or tissue.

In one embodiment, the invention concerns a method for the analysis of in vivo localization or trafficking of a polypeptide of interest, comprising the steps of: (a) providing a polynucleotide encoding a fusion protein, comprising at least one fluorescent protein encoded by the polynucleotides discussed above, operatively joined to at least one other polypeptide of interest and a host cell or tissue, and (b) visualizing said fusion protein that is expressed in said host cell or tissue.

Also disclosed are methods for detecting protein kinase or phosphatase activity. In one embodiment, the disclosed fluorescent polypeptides and variants thereof are used to detect protein kinase or phosphatase activity, wherein the fluorescence emission of the disclosed fluorescent polypeptides and variants thereof is indicative of the activity of a protein kinase or phosphatase.

Further disclosed are cell-based methods for screening for kinase or phosphatase modulators by utilizing a fluorescent protein disclosed herein.

In one embodiment, the cell-based method of the invention utilizes the fluorescent protein, PhosFluor, which comprises the amino acid sequence as set forth in SEQ ID NO: 10, or a variant or derivative thereof. Such fluorescent protein has been identified as capable of optically detecting protein phosphorylation in living cells in real time.

In a specific embodiment, the cell-based assay is designed to screen for protein kinase and phosphatase inhibitors, including, for example, inhibitors of the Akt1 kinase.

BRIEF DESCRIPTION OF THE DRAWINGS

Figure 1A:
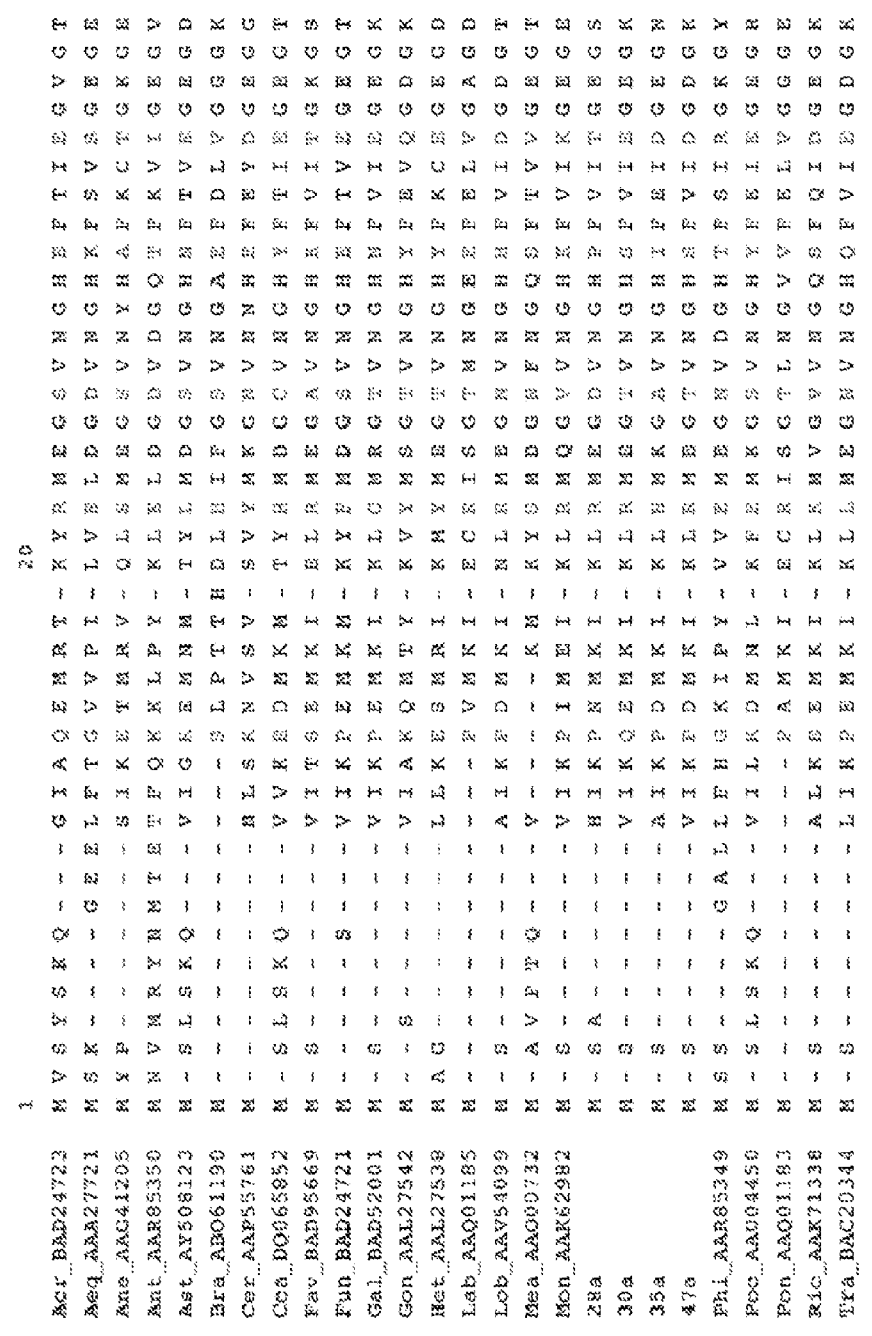
Figure 1B:
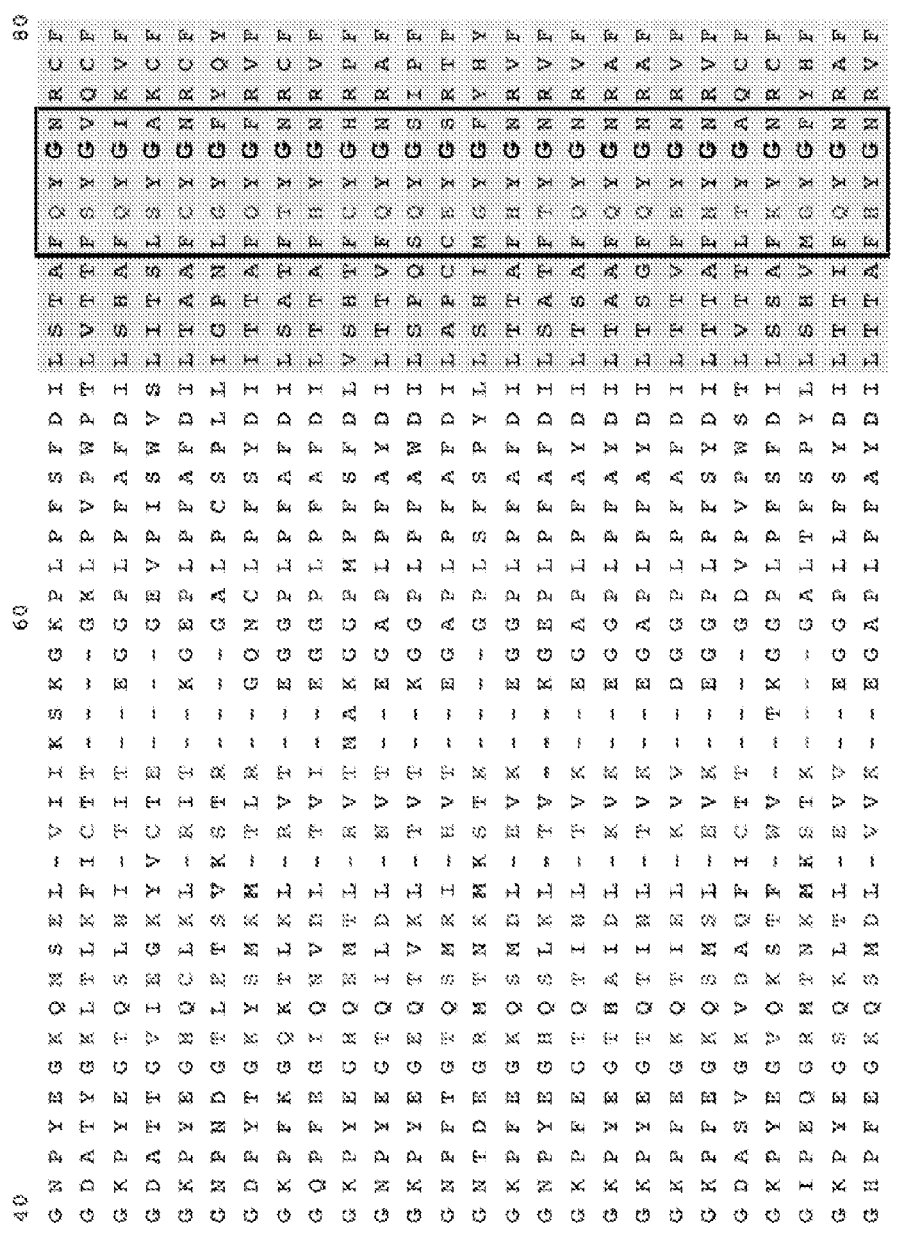
Figure 1C:
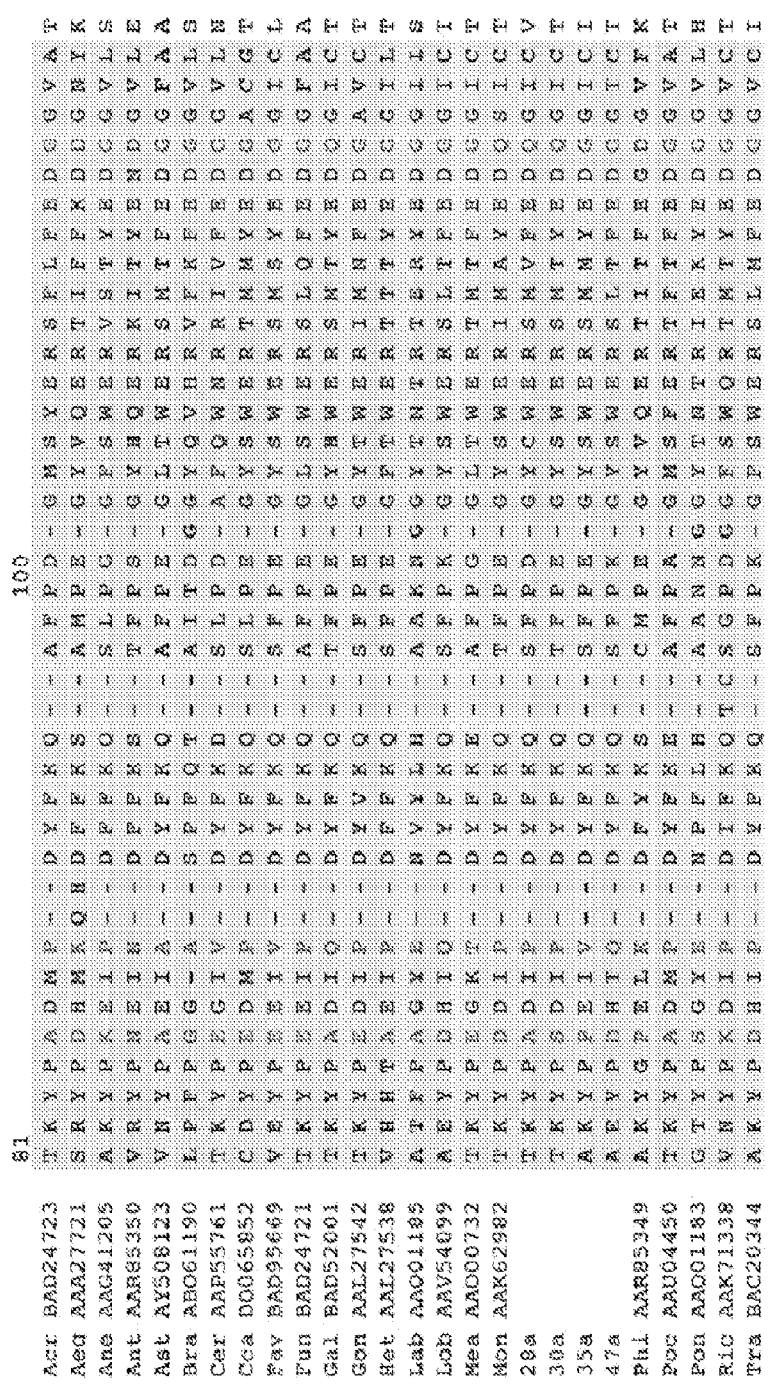
Figure 1D:
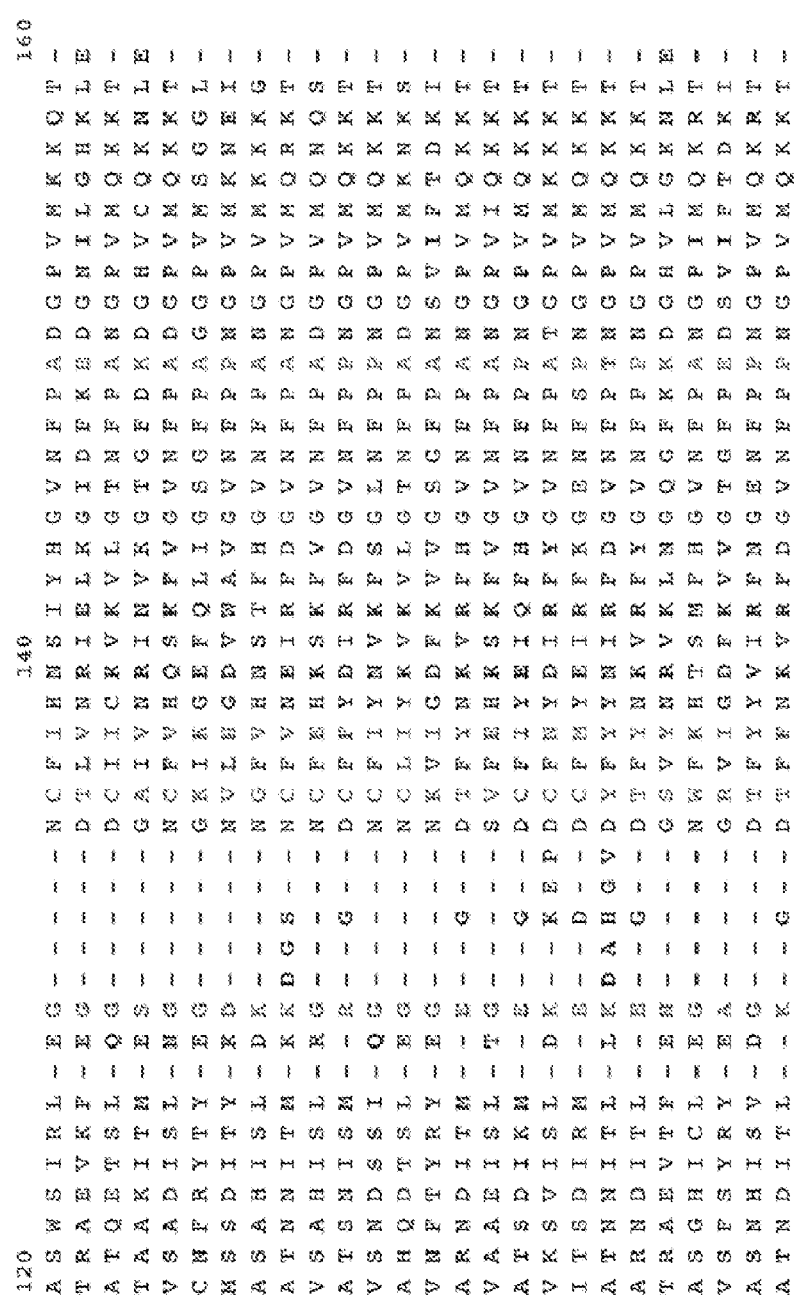
Figure 1E:
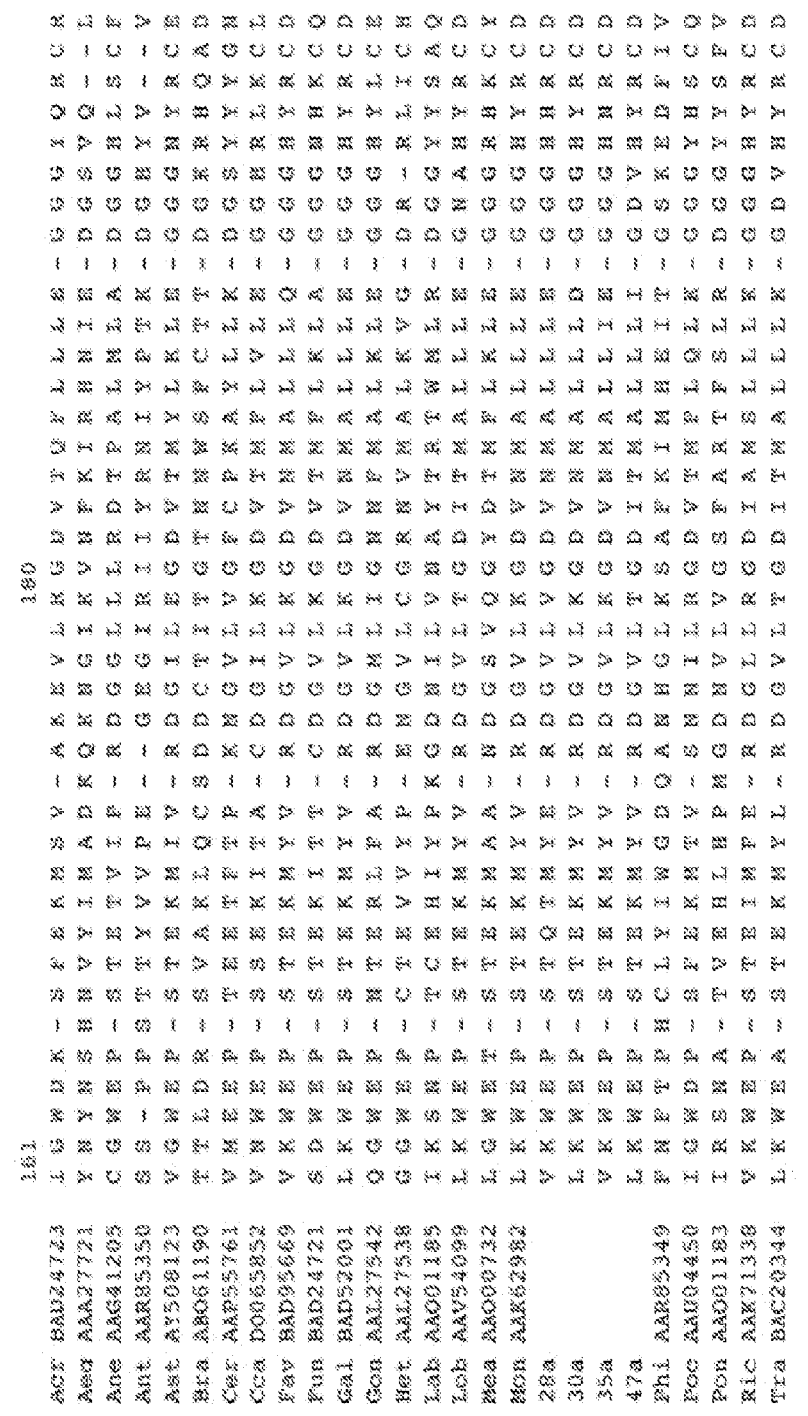
Figure 1F:
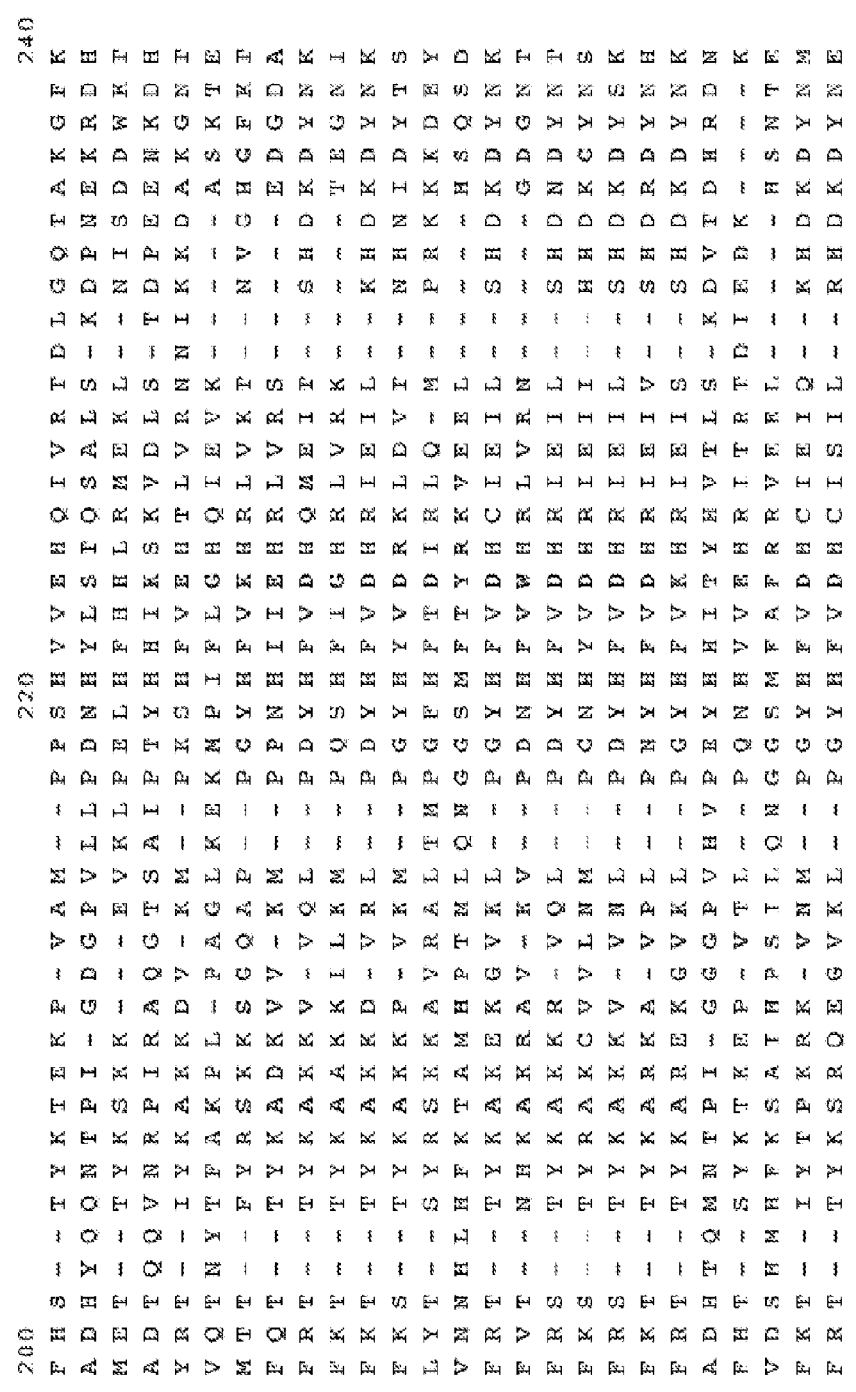
Figure 1G:
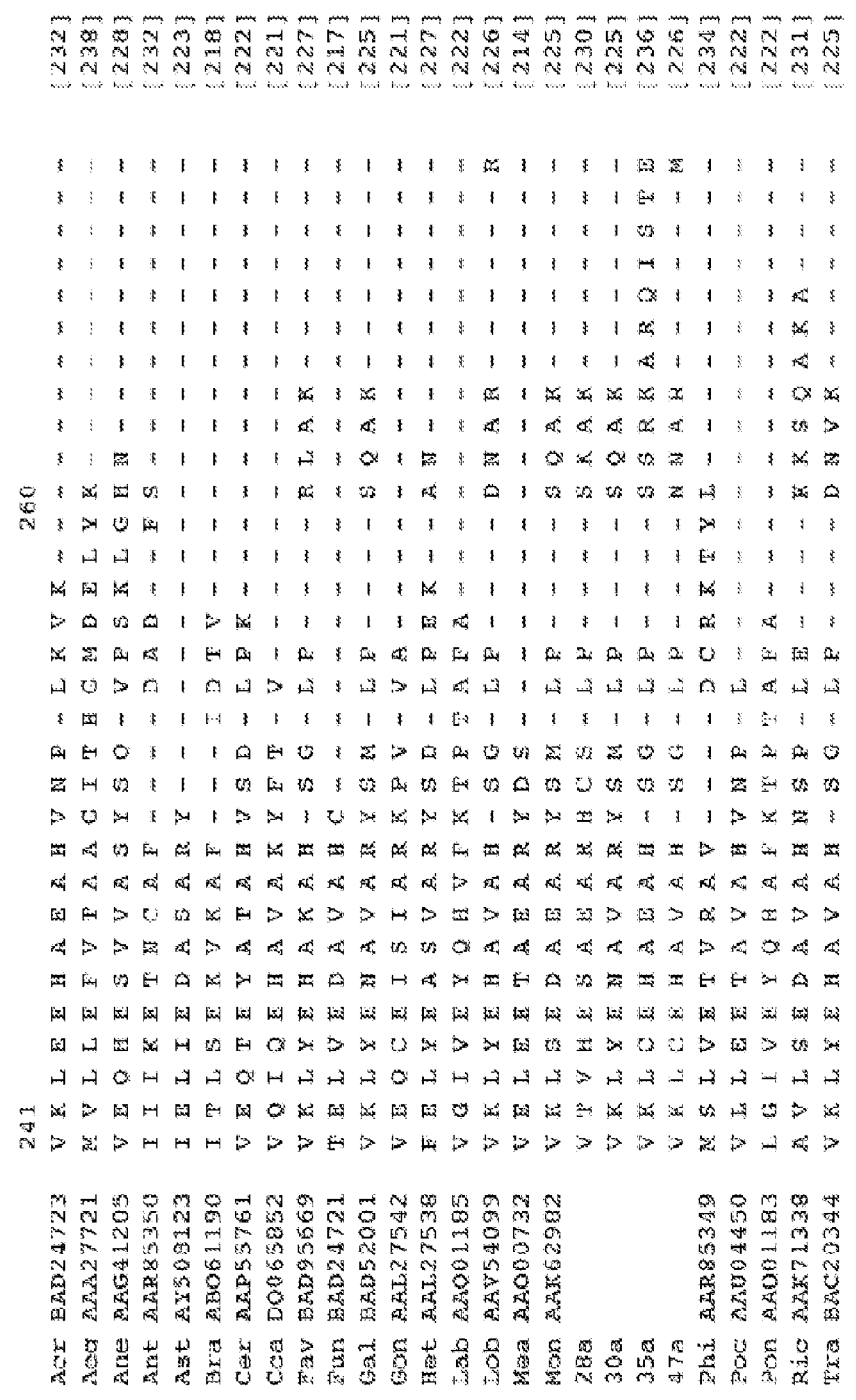

FIG. 1, which is presented in the drawings as FIGS. 1A-G, is an alignment of a subset of fluorescent proteins spanning representative genus (SEQ ID NOS 49-65, 10, 14, 28, 42, and 66-70, respectively, in order of appearance). The highlighted portion of the sequences corresponds to the chromophore region of the fluorescent proteins.

FIG. 5 shows the amino acid sequence of red fluorescent protein (SEQ ID NO: 71), and the respective residues which are highly variable, as compared to other fluorescent proteins (asterisks). Residues 61-105 correspond to the conserved central fluorescent protein region. This region is flanked by the N- and C-terminal variable regions (residues 1 to 60, and 106 to 225) respectively. Residues 13, 30, 32, 34, 36, 41, 43, 45, 201, and 211 are fluorescent protein residues homologous to Perlecan-binding residues in Nidogens. The boxed residues are homologous to both Perlecan-binding residues in Nidogen proteins, and highly variable residues in fluorescent proteins.

FIGS. 9A-9B disclose the modulation of PhosFluor by alkaline pH and phosphorylation. A. Equal quantities of the indicated fluorescent proteins were subjected to different pH by addition of Tris buffer. Normalized fluorescence intensity (excitation at 485 nm and emission at 538 nm, compared to the value at pH 7.0) was measured using a SpectraMax M5 Microplate Reader. B. Equal quantities of the recombinant PhosFluor or eGFP were subjected to phosphorylation by the indicated protein kinases or to dephosphorylation with alkaline phosphatase (Alk Phos). Fluorescence intensity (representing the change in emission of a part of the emission spectrum compared to the value at 0 hours) was measured over time during the reaction. The PhosFluor reaction containing no enzyme showed an increase in fluorescence over time, but virtually no change was observed when the reaction was incubated with alkaline, thereby suggesting the presence of an endogenous bacterial protein kinase that was co-purified with PhosFluor.

DETAILED DESCRIPTION OF THE DISCLOSURE

Definitions

Figure 2A:
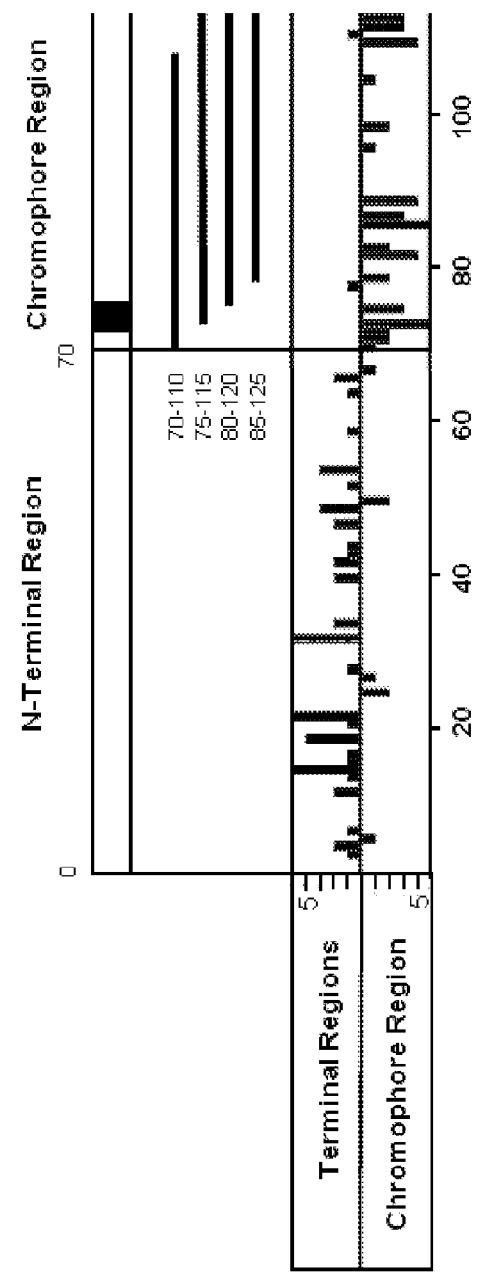
FIG. 2 is a map of a typical fluorescent protein, shown with terminal regions separated from the internal chromophore region. The 3-residue chromophore is shown in the internal region with a shaded box. Below the map are lines representing 40-residue sliding window segments (with region designated) that were examined for congruence with the terminal regions. Dark lines indicate sliding windows that were shown to be incongruent with the terminal regions with statistical significance. The histogram below the map plots the difference in number of steps it takes to construct a phylogenetic tree using the N/C terminal regions versus the middle region, for each residue in the protein. Residue position is indicated on the bottom of the histogram.

Unless specifically indicated otherwise, all technical and scientific terms used herein have the same meaning as commonly understood by those of ordinary skill in the art to which this disclosure pertains, or with which it is most nearly connected. For purposes of the present invention, the following terms are defined.

The term "nucleic acid molecule" or "polynucleotide" refers to a deoxyribonucleotide or ribonucleotide polymer in either single-stranded or double-stranded form, and, unless specifically indicated otherwise, encompasses polynucleotides containing known analogs of naturally-occurring nucleotides which can function in a similar manner as naturally-occurring nucleotides. It will be understood that when a nucleic acid molecule is represented by a DNA sequence, this also includes RNA molecules comprising a nucleotide sequence which corresponds to a DNA sequence in which "U" (uridine) replaces "T" (thymidine).

The term "recombinant nucleic acid molecule" refers to a non-naturally occurring nucleic acid molecule containing two or more linked polynucleotide sequences. A recombinant nucleic acid molecule can be produced by recombination methods, particularly genetic engineering techniques, or can be produced by a chemical synthesis method. A recombinant nucleic acid molecule can encode a fusion protein, for example, a disclosed fluorescent protein variant linked to a polypeptide or peptide of interest. The term "recombinant host cell" refers to a cell that contains a recombinant nucleic acid molecule. As such, a recombinant host cell can express a polypeptide from a "gene" that is not found within the native (non-recombinant) form of the cell.

Reference to a polynucleotide "encoding" a polypeptide means that, upon transcription of the polynucleotide and translation of the mRNA transcript, a polypeptide is produced. The encoding polynucleotide is considered to include both the coding strand, whose nucleotide sequence is identical to the nucleotide sequence of an mRNA, as well as its complementary strand, whose nucleotide sequence is complementary to the nucleotide sequence of an mRNA. It will be recognized that such a polynucleotide encoding a polypeptide is considered to include degenerate nucleotide sequences, which encode the same amino acid residues. Nucleotide sequences encoding a polypeptide can include polynucleotides containing introns as well as the encoding exons.

The term "expression control sequence" refers to a nucleotide sequence that regulates the transcription or translation of a polynucleotide or the localization of a polypeptide to which to which it is operatively linked. Expression control sequences are "operatively linked" when the expression control sequence controls or regulates the transcription and, as appropriate, translation of the nucleotide sequence which encodes a polypeptide (i.e., a transcription or translation regulatory element, respectively), or localization of the encoded polypeptide to a specific compartment of a cell or tissue. Thus, an expression control sequence can be a promoter, enhancer, transcription terminator, a start codon (ATG), a splicing signal for intron excision and maintenance of the correct reading frame, a STOP codon, a nucleotide sequence encoding a ribosome binding site, or a sequence that targets a polypeptide to a particular location, for example, a cell compartmentalization signal which can target a polypeptide to the cytosol, nucleus, plasma membrane, endoplasmic reticulum, mitochondrial membrane or matrix, chloroplast membrane or lumen, medial trans-Golgi cisternae, or a lysosome or endosome. Cell compartmentalization domains are well known in the art and include, for example, a peptide containing amino acid residues 1 to 81 of human type II membrane-anchored protein galactosyltransferase, or amino acid residues 1 to 12 of the presequence of subunit IV of cytochrome c oxidase (see, also, Hancock et al. (1991), *EMBO J.* 10, pp. 4033-4039; Buss et al. (1988), *Mol. Cell. Biol.* 8, pp. 3960-3963; U.S. Pat. No. 5,776,689, each of which is incorporated herein by reference).

The term "operatively linked" or "operably linked" or "operatively joined," when used herein to describe fusion proteins, refers to polypeptide sequences that are placed in a physical and/or functional relationship with each other. The functional activity of the components of a given fusion protein are preferably unchanged compared to the functional activities of the individual components when the components are not operatively joined. For example, a disclosed fluorescent polypeptide or variant thereof, can be fused to a polypeptide of interest. In this case, it is preferable that the fusion molecule retains its fluorescence, and the polypeptide of interest retains its original biological activity. In some embodiments of the present invention, the activities of either the fluorescent protein or the protein of interest can be reduced relative to their activities in isolation. Such fusions can also find use with the present invention. As used herein, the chimeric fusion molecules of the invention can be in a monomeric state, or in a multimeric state (e.g., dimeric, trimeric or tetrameric).

The term "oligomer" refers to a complex formed by the specific interaction of two or more polypeptides. A "specific interaction" or "specific association" is one that is relatively stable under specified conditions, for example, physiologic conditions. Reference to a "propensity" of proteins to oligomerize indicates that the proteins can form dimers, trimers, tetramers, or the like under specified conditions. Generally, fluorescent proteins such as GFPs have a propensity to oligomerize under physiologic conditions although, as disclosed herein, fluorescent proteins also can oligomerize, for example, under pH conditions other than physiologic conditions. The conditions under which fluorescent proteins oligomerize or have a propensity to oligomerize can be determined using well known methods as disclosed herein or otherwise known in the art.

The terms "polypeptide" and "protein" are synonymous, and refer to a polymer of two or more amino acid residues. The terms apply to amino acid polymers in which one or more amino acid residue is an artificial chemical analog of a corresponding naturally-occurring amino acid, as well as to naturally-occurring amino acid polymers.

The term "recombinant protein" refers to a protein that is produced by expression of a recombinant polynucleotide encoding the protein.

The term "isolated" or "purified" refers to a material that is substantially or essentially free from components that normally accompany the material in its native state. Purity or homogeneity generally is determined using analytical techniques such as polyacrylamide gel electrophoresis and high performance liquid chromatography. A polynucleotide or a polypeptide is considered to be isolated when it is the predominant polynucleotide or a polypeptide present in a preparation, respectively. An isolated protein or nucleic acid molecule represents greater than 80% of the macromolecular species present in a preparation, greater than 90% of all macromolecular species present, greater than 95% of all macromolecular species present, greater than 96% of all macromolecular species present, greater than 97% of all macromolecular species present, greater than 98% of all macromolecular species present, greater than 99% of all the macromolecular species, and, in particular, is a polypeptide or polynucleotide that purified essentially to homogeneity such that the polypeptide or polynucleotide is the only macromolecular species detected when examined using conventional methods for determining purity of such a molecule.

The term "naturally-occurring" is used to refer to a protein, nucleic acid molecule, cell, or other material that occurs in nature (i.e., wild type molecule), for example, a polypeptide or polynucleotide sequence that is present in an organism, including in a virus. A naturally-occurring material can be in its form as it exists in nature, and can be modified by the hand of man such that, for example, is in an isolated form.

The term "antibody" refers to a polypeptide encoded by at least one portion of an immunoglobulin gene. The recognized immunoglobulin genes include the kappa, lambda, alpha, gamma, delta, epsilon and mu constant region genes, as well as the myriad of immunoglobulin variable region genes. Antibodies exist as intact immunoglobulins and as well characterized antigen-binding fragments of an antibody which can be produced by digestion with a peptidase or by recombinant DNA methods. Such antigen-binding fragments of an antibody include, for example, Fv, Fab' and F(ab)'$_2$ fragments. "Antibody," as used herein, includes antibody fragments either produced by the modification of whole antibodies or those synthesized de novo using recombinant DNA methodologies.

The term "identical" is used herein in reference to two or more polynucleotide sequences or, alternatively, two or more polypeptide sequences. The term "identical" refers to nucleotides in one nucleotide sequence that are the same as nucleotides in another nucleotide sequence when the nucleotide sequences are aligned for maximum correspondence. Similarly, the term "identical" refers to amino acid residues in one amino acid sequence that are the same as amino acid residues in another amino acid sequence when the amino acid sequences are aligned for maximum correspondence. When percentage of sequence identity is used in reference to a polypeptide, it is recognized that one or more residue positions that are not otherwise identical can differ by a conservative amino acid substitution, in which a first amino acid residue is substituted for another amino acid residue having similar chemical properties such as a similar charge, hydrophobic character, or hydrophilic character and, therefore, does not substantially change the functional properties of the polypeptide. Where polypeptide sequences differ in conservative substitutions, the percent sequence identity can be adjusted upwards to correct for the conservative nature of the substitution. Such an adjustment can be made using well known methods, for example, scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions can be calculated using any well known algorithm (see, e.g., Meyers and Miller (1988), *Comp. Appl. Biol. Sci.* 4, pp. 11-17; Smith and Waterman (1981), *Adv. Appl. Math.* 2, p. 482; Needleman and Wunsch (1970), *J. Mol. Biol.* 48, p. 443; Pearson and Lipman (1988), *Proc. Natl. Acad. Sci., USA* 85, p. 2444; Higgins and Sharp (1988), *Gene* 73, pp. 237-244). Manual alignment also can be performed by simple visual inspection and manual alignment of sequences. Such manual alignments are well known in the art.

Two or more nucleotide sequences are considered to be "substantially identical" if the nucleotide sequences share at least 80% sequence identity with each other, or with a reference sequence over a given comparison window. Similarly, two or more amino acid sequences are considered to be "substantially identical" or "substantially similar" if the amino acid sequences share at least 80% sequence identity with each other, or with a reference sequence over a given comparison window. Thus, substantially similar sequences include those having, for example, at least 85% sequence identity, at least 88% sequence identity, at least 90% sequence identity, at least 92% sequence identity, at least 95% sequence identity, at least 97% sequence identity, or at least 99% sequence identity.

A "variant" polypeptide or "variant" polynucleotide is substantially identical in sequence to the respective native (wild type) polypeptide or polynucleotide.

Fluorescent molecules are useful in fluorescence resonance energy transfer, FRET, which involves a donor molecule and an acceptor molecule. To optimize the efficiency and detectability of FRET between a donor and acceptor molecule, several factors need to be balanced. The emission spectrum of the donor should overlap as much as possible with the excitation spectrum of the acceptor to maximize the overlap integral. Also, the quantum yield of the donor moiety and the extinction coefficient of the acceptor should be as high as possible to maximize $R_O$, which represents the distance at which energy transfer efficiency is 50%. However, the excitation spectra of the donor and acceptor should overlap as little as possible so that a wavelength region can be found at which the donor can be excited efficiently without directly exciting the acceptor because fluorescence arising from direct excitation of the acceptor can be difficult to distinguish from fluorescence arising from FRET. Similarly, the emission spectra of the donor and acceptor should overlap as little as possible so that the two emissions can be clearly distinguished. High fluorescence quantum yield of the acceptor moiety is desirable if the emission from the acceptor is to be measured either as the sole readout or as part of an emission ratio. One factor to be considered in choosing the donor and acceptor pair is the efficiency of fluorescence resonance energy transfer between them. Preferably, the efficiency of FRET between the donor and acceptor is at least 10%, more preferably at least 50% and even more preferably at least 80%.

The term "fluorescent property" or "fluorescent characteristics" refers to the molar extinction coefficient at an appropriate excitation wavelength, the fluorescence quantum efficiency, the shape of the excitation spectrum or emission spectrum, the excitation wavelength maximum and emission wavelength maximum, the ratio of excitation amplitudes at two different wavelengths, the ratio of emission amplitudes at two different wavelengths, the excited state lifetime, fluorescence intensity, fluorescence lifetime, multiphoton cross-section, fluorescence resonance energy transfer efficiency, bioluminescence resonance energy transfer efficiency, or the fluorescence anisotropy. A measurable difference in any one of these properties between the wild type GFP of *A. victoria* and a spectral variant thereof, or the wild type GFP of *A. victoria* and a mutant of a spectral variant thereof, is useful. A measurable difference can be determined by determining the amount of any quantitative fluorescent property, e.g., the amount of fluorescence at a particular wavelength, or the integral of fluorescence over the emission spectrum.

As used herein, the term "fluorescent protein" refers to any protein that can fluoresce when excited with an appropriate electromagnetic radiation, except that chemically tagged proteins, wherein the fluorescence results from the chemical tag, and polypeptides that fluoresce only due to the presence of certain amino acids such as tryptophan or tyrosine, whose emission peaks at ultraviolet wavelengths (i.e., less that about 400 nm) are not considered fluorescent proteins for purposes of the present disclosure. In general, a disclosed fluorescent protein is a protein which derives its fluorescence from autocatalytically forming a chromophore. A fluorescent protein can contain amino acid sequences that are naturally occurring or that have been engineered (i.e., variants or mutants). When used in reference to a fluorescent protein, the term "mutant" or "variant" refers to a protein that is different from a reference fluorescent protein. For example, a spectral variant of *Aequorea* GFP can be derived from the naturally occurring GFP by engineering mutations such as amino acid substitutions into the reference GFP protein (see, e.g., U.S. Pat. No. 5,777,079). A "spectral variant" or "spectral mutant" of a fluorescent protein indicates a mutant fluorescent protein which has a different fluorescence characteristic with respect to the corresponding wild type or reference fluorescent protein.

The term "coral" as used herein encompasses species within the class Anthozoa (e.g., species of the order Scleractinia) and includes corals, stony corals and corallimorphs.

Fluorescent Proteins

The GFP of *A. victoria* and blue, cyan, and yellow variants thereof have found widespread use as both genetically-encoded indicators for tracking gene expression and as donor/acceptor pairs for fluorescence resonance energy transfer (FRET). However, extending the spectrum of available colors to red wavelengths, and the further engineering of these proteins to create biosensors and to detect novel protein-protein interactions, e.g., for high throughput drug screening would provide distinct new labels for multicolor tracking of fusion proteins and the detection of various interactions.

Accordingly, disclosed herein are isolated fluorescent proteins from organisms of the order Scleractinia, which are indigenous to the Australian Great Barrier Reef. Further disclosed are fluorescent proteins with fluorescent properties disclosed above.

Illustrative examples of the disclosed isolated fluorescent proteins include proteins comprising an amino acid sequence selected from the groups consisting of SEQ ID NOs: 10, 12, 14, 16, 18, 20, 22, 24, 26, 28, 30, 32, 34, 36, 38, 40, 42, and 44.

The sequences associated with these SEQ ID NOs are provided in the Sequence Listing.

Also disclosed herein are polynucleotides encoding the isolated fluorescent proteins. In one embodiment, a nucleic acid molecule is provided that comprises a nucleotide sequence selected from the group consisting of SEQ ID NOs: 11, 13, 15, 17, 19, 21, 23, 25, 27, 29, 31, 33, 35, 37, 39, 41, 43, and 45. The sequences associated with these SEQ ID NOs are provided in the Sequence Listing.

The disclosed isolated fluorescent proteins contain three distinct regions: a first region of 45 amino acid residues which includes a chromophore; a second region of 50-amino acid residues N-terminal of the first region; and a third region of 140 amino acid residues C-terminal of the first).

Figure 3:
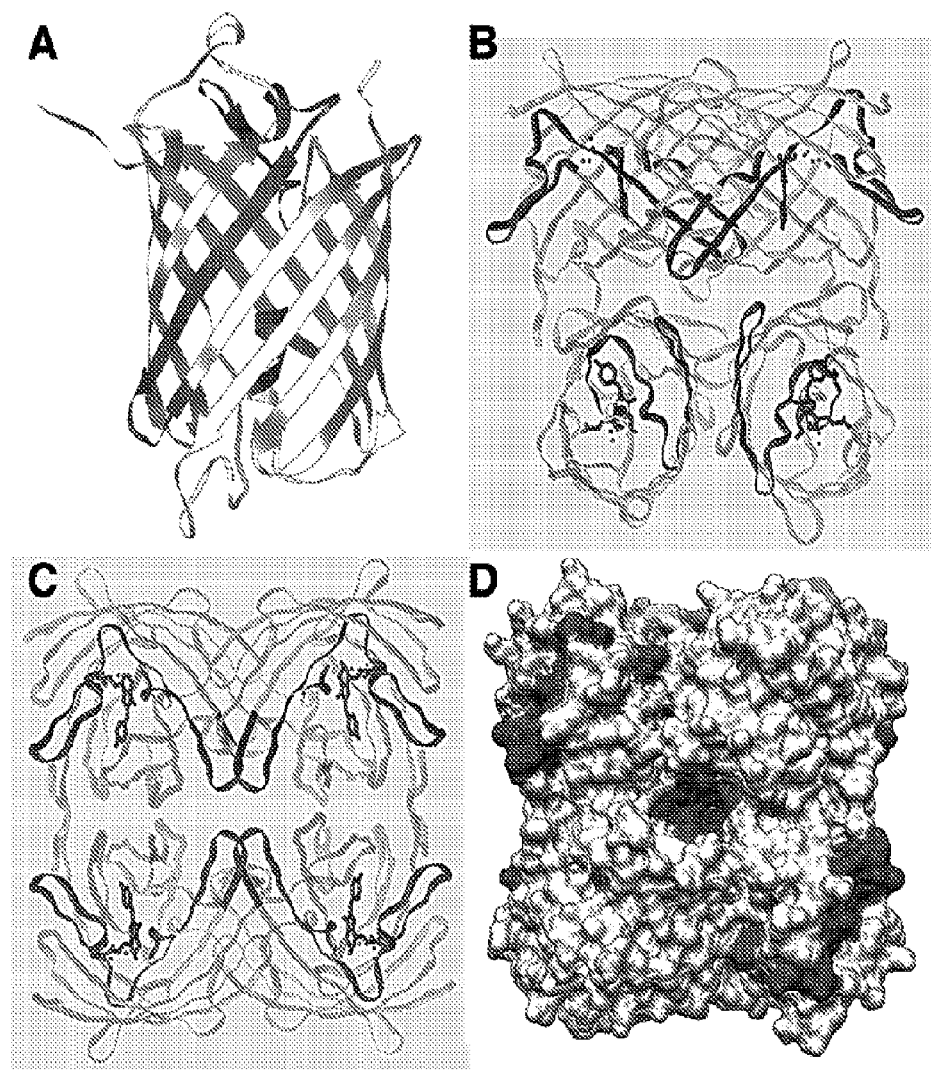
FIGS. 3A-D are diagrams of the crystal structure of a red fluorescent protein from *Discosoma* sp. ("DsRed"). The conserved central domain (dark) and flanking variable domains (white/grey) are imposed on a ribbon diagram of monomer (A) and tetramer (B and C) of the red fluorescent protein crystal structure. (B) Standard view of the tetramer. (C) depicts a slight rotation to highlight the proximity of the β strands of the conserved region. (D) Electron density map created in Chimera (Pettersen et al. (2004). *J. Comp. Chemistry* 25, pp 1605-1612) depicting residues (dark) corresponding to the middle conserved region mapped to the crystal structure of DsRed.

The chromophore region of 45 amino acid residues, specifically residues 70 to 115, displays a sharply divergent evolutionary pattern from the rest of the protein. The chromophore region evolved slowly under stabilizing selection. The structure of the chromophore region contains an α helix and a single β strand. The β strand faces inward in the tetrameric fluorescent protein complex (see FIG. 3).

Figure 4:
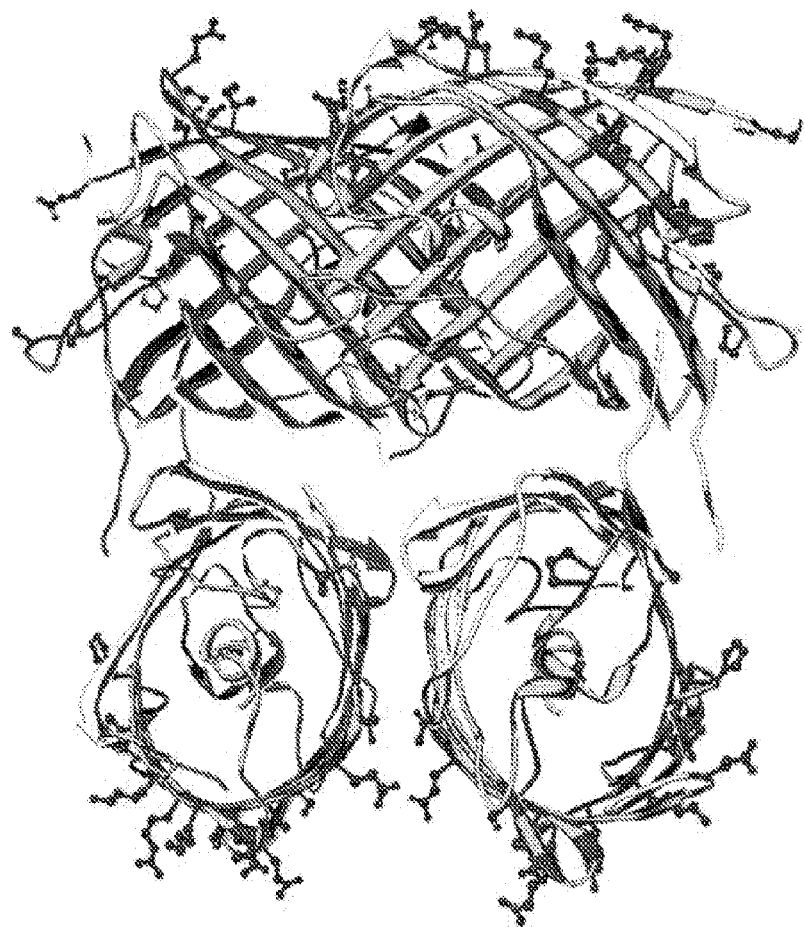
FIG. 4 is a ball-and-stick diagram of the crystal structure of DsRed. Residues undergoing rapid molecular change are shown in a darker shade. These residues were determined by analyses of fluorescent proteins derived from specimens of *Montastrea cavernosa* from different geographic regions.

The N-terminal and C-terminal regions are under intense Darwinian selection and evolve rapidly with mutations appearing at sites of putative protein-protein interactions (see FIG. 4). In addition, fluorescence color is significantly associated with the N-terminal and C-terminal hypervariable regions and not with the middle conserved region.

Fluorescent Protein Variants

The present invention provides variant fluorescent proteins, which differ from the fluorescent proteins having a polypeptide sequence as set forth in any of SEQ ID NOS: 10, 12, 14, 16, 18, 20, 22, 24, 26, 28, 30, 32, 34, 36, 38, 40, 42 or 44.

In one embodiment, the present invention is directed to a novel fluorescent protein having an amino acid sequence comprising a sequence with at least 80% identity to that of any of sequences identified as SEQ ID NOS: 10, 12, 14, 16, 18, 20, 22, 24, 26, 28, 30, 32, 34, 36, 38, 40, 42 and 44. In a further embodiment, the variant has at least 85%, 90%, 92%, 95%, 97%, 98% or 99% identity to the aforementioned sequences.

In one embodiment, the fluorescent protein variant of the present invention has a mutation in at least one of the hypervariable residues. In a further embodiment, the one or more mutations results in a fluorescent protein with less of a propensity to oligomerize, or a protein that specifically binds a protein or small molecule of interest.

As stated above, variant fluorescent proteins of the invention can have a reduced propensity to oligomerize, due to the presence of one or more mutations at the fluorescent protein's surface. In one embodiment, one of the starred residues in FIG. 5 is mutated to arrive at a variant fluorescent protein with a reduced propensity to oligomerize.

Amino acids with charged (ionized D, E, K, and R), dipolar (H, N, Q, S, T, and uncharged D, E and K), and polarizable side groups (e.g., C, F, H, M, W and Y) are useful for altering the ability of fluorescent proteins to oligomerize or interact with other proteins, especially when they substitute an amino acid with an uncharged, nonpolar or non-polarizable side chain.

In one embodiment, the present invention provides a variant fluorescent protein that fluoresces at a different wavelength, as compared to the protein the variant was derived from. In this embodiment, one or more residues in the fluorescent protein's terminal hypervariable region (region does not include the chromophore) is mutated.

In another embodiment, a variant fluorescent protein of the present invention only fluoresces when binding to a protein of interest.

Fusion Proteins Comprising the Disclosed Fluorescent Proteins

Fluorescent proteins fused to target proteins can be prepared, for example using recombinant DNA methods, and used as markers to identify the location and amount of the target protein produced. Accordingly, the present invention provides fusion proteins comprising a fluorescent protein (including those described above and variants thereof) and a polypeptide or peptide of interest. The polypeptide of interest can be of any length, for example, about 15 amino acid residues, about 50 residues, about 150 residues, or up to about 1000 amino acid residues or more, provided that the fluorescent protein component of the fusion protein can fluoresce or can be induced to fluoresce when exposed to electromagnetic radiation of the appropriate wavelength. The polypeptide of interest can be, for example, a peptide tag such as a polyhistidine sequence, a c-myc epitope, a FLAG epitope, and the like; can be an enzyme, which can be used to effect a function in a cell expressing a fusion protein comprising the enzyme or to identify a cell containing the fusion protein; can be a protein to be examined for an ability to interact with one or more other proteins in a cell, or any other protein as disclosed herein or otherwise desired.

A fusion protein of the present invention can include a fluorescent protein disclosed herein operatively linked to one or more polypeptides of interest. The two or more polypeptides of the fusion protein can be linked through peptide bonds, or the fluorescent protein can be linked to the one or more polypeptides of interest through a linker molecule.

In one embodiment, a linker can be present to join the fluorescent protein of the present invention and a polypeptide of interest. If the linker between the two moieties is a non-peptide linker, the two subunits will be encoded by separate polynucleotide molecules, produced separately, and subsequently linked by methods known in the art.

In another embodiment, the fusion protein is expressed from a recombinant nucleic acid molecule containing a polynucleotide encoding a fluorescent protein disclosed herein operatively linked to one or more polynucleotides encoding one or more polypeptides of interest.

A polypeptide of interest can be any polypeptide, including, for example, a peptide tag such as a polyhistidine peptide, or a cellular polypeptide such as an enzyme, a G-protein, a growth factor receptor, or a transcription factor; and can be one of two or more proteins that can associate to form a complex. In one embodiment, the fusion protein is a tandem fluorescent protein variant construct, which includes a donor fluorescent protein disclosed herein, an acceptor fluorescent protein disclosed herein, and a peptide linker moiety coupling said donor and said acceptor, wherein cyclized amino acids of the donor emit light characteristic of said donor, and wherein the donor and the acceptor exhibit fluorescence resonance energy transfer when the donor is excited, and the linker moiety does not substantially emit light to excite the donor. As such, a fusion protein of the invention can include two or more operatively linked fluorescent proteins, which can be linked directly or indirectly, and can further comprise one or more polypeptides of interest.

Preparation of Fluorescent Proteins

The present invention also provides polynucleotides encoding fluorescent proteins, or variants thereof, where the protein can be a fluorescent protein isolated from Scleractinia (Lizard Island, Australia), a variant thereof, or a fusion protein comprising such a fluorescent protein (or variant) operatively linked to one or more polypeptides of interest.

The invention further provides vectors containing such polynucleotides, and host cell containing a polynucleotide or vector. Also provided is a recombinant nucleic acid molecule, which includes at least one polynucleotide encoding a fluorescent protein operatively linked to one or more other polynucleotides. The one or more other polynucleotides can be, for example, a transcription regulatory element such as a promoter or polyadenylation signal sequence, or a translation regulatory element such as a ribosome binding site. Such a recombinant nucleic acid molecule can be contained in a vector, which can be an expression vector, and the nucleic acid molecule or the vector can be contained in a host cell.

The vector generally contains elements required for replication in a prokaryotic or eukaryotic host system or both, as desired. Such vectors, which include plasmid vectors and viral vectors such as bacteriophage, baculovirus, retrovirus, lentivirus, adenovirus, vaccinia virus, semliki forest virus and adeno-associated virus vectors, are well known and can be purchased from a commercial source (Promega, Madison Wis.; Stratagene, La Jolla Calif.; GIBCO/BRL, Gaithersburg Md.) or can be constructed by one skilled in the art (see, e.g., Meth. Enzymol., Vol. 185, Goeddel, ed. (Academic Press, Inc., 1990); Jolly (1994), *Canc. Gene Ther.* 1, pp. 51-64; Flotte (1993), *Bioenerg. Biomemb.* 25, pp. 37-42; Kirshenbaum et al. (1992), *J. Clin. Invest.* 92, pp. 381-387; each of which is incorporated herein by reference in its entirety).

A vector for containing a polynucleotide encoding a fluorescent protein can be a cloning vector or an expression vector, and can be a plasmid vector, viral vector, and the like. Generally, the vector contains a selectable marker independent of that encoded by a polynucleotide of the invention, and further can contain transcription or translation regulatory elements, including a promoter sequence, which can provide tissue specific expression of a polynucleotide operatively linked thereto, which can, but need not, be the polynucleotide encoding the fluorescent protein, for example, a variant fluorescent protein with a decreased propensity to oligomerize, thus providing a means to select a particular cell type from among a mixed population of cells containing the introduced vector and recombinant nucleic acid molecule contained therein.

Where the vector is a viral vector, it can be selected based on its ability to infect one or few specific cell types with relatively high efficiency. For example, the viral vector also can be derived from a virus that infects particular cells of an organism of interest, for example, vertebrate host cells such as mammalian host cells. Viral vectors have been developed for use in particular host systems, particularly mammalian systems and include, for example, retroviral vectors, other lentivirus vectors such as those based on the human immunodeficiency virus (HIV), adenovirus vectors, adeno-associated virus vectors, herpesvirus vectors, vaccinia virus vectors, and the like (see Miller and Rosman (1992), *BioTechniques* 7, pp. 980-990; Anderson et al. (1998), *Nature* 392, pp. 25-30 Suppl.; Verma and Somia (1997), *Nature* 389, pp. 239-242; Wilson (1996), *New Engl. J. Med.* 334, pp. 1185-1187).

Recombinant production of a fluorescent protein, which can be a component of a fusion protein, involves expressing a polypeptide encoded by a polynucleotide. A polynucleotide encoding the fluorescent protein is a useful starting material. In one embodiment, the polynucleotide comprises one or more of the sequences identified as SEQ ID NOS: 11, 13, 15, 17, 19, 21, 23, 25, 27, 29, 31, 33, 35, 37, 39, 31 or 43 or 45 is employed. In another embodiment, a polynucleotide comprises a polynucleotide sequence having at least 80% identity to one of the sequences identified as SEQ ID NOS: 11, 13, 15, 17, 19, 21, 23, 25, 27, 29, 31, 33, 35, 37, 39, 31 or 43 or 45. In a further embodiment, the variant has at least 85%, at least 87%, at least 90%, at least 92%, at least 95% or at least 97% identity to one of the sequences identified as SEQ ID NOS: 11, 13, 15, 17, 19, 21, 23, 25, 27, 29, 31, 33, 35, 37, 39, 31 or 43 or 45.

Polynucleotides encoding a fluorescent protein are disclosed herein or otherwise known in the art, and can be obtained using routine methods, then can be modified such that the encoded fluorescent protein has a biophysical property altered. For example, the resulting fluorescent protein variant may be engineered to bind specifically to a protein target. Alternatively or additionally, the variant may emit fluorescence only when the binding occurs.

For example, a polynucleotide encoding a fluorescent protein of the present invention, can be isolated by PCR of cDNA from Sclereactinia using primers based on the polynucleotide sequences provided as SEQ ID NOS: 11, 13, 15, 17, 19, 21, 23, 25, 27, 29, 31, 33, 35, 37, 39, 41, 43 or 45, or alternatively, sets of degenerate primers (e.g., primers comprising a sequence identified as any of SEQ ID NOS: 1-9). PCR methods are well known and routine in the art (see, e.g., U.S. Pat. No. 4,683,195; Mullis et al. (1987), *Cold Spring Harbor Symp. Quant. Biol.* 51, p. 263; Erlich, ed., "PCR Technology" (Stockton Press, NY, 1989)). A variant form of the fluorescent protein then can be made by site-specific mutagenesis of the polynucleotide encoding the fluorescent protein.

The construction of expression vectors and the expression of a polynucleotide in transfected cells involves the use of molecular cloning techniques also well known in the art (see Sambrook et al., In "Molecular Cloning: A Laboratory Manual" (Cold Spring Harbor Laboratory Press 1989); "Current Protocols in Molecular Biology" (eds., Ausubel et al.; Greene Publishing Associates, Inc., and John Wiley & Sons, Inc. 1990 and supplements)). Expression vectors contain expression control sequences operatively linked to a polynucleotide sequence of interest, for example, that encodes a fluorescent protein variant, as indicated above. The expression vector (for example, pCR4Blunt-TOPO (Invitrogen, Carlsbad, Calif.)) can be adapted for function in prokaryotes or eukaryotes by inclusion of appropriate promoters, replication sequences, markers, and the like. An expression vector can be transfected into a recombinant host cell for expression of a fluorescent protein variant, and host cells can be selected, for example, for high levels of expression in order to obtain a large amount of isolated protein. A host cell can be maintained in cell culture, or can be a cell in vivo in an organism. A fluorescent protein or variant thereof can be produced by expression from a polynucleotide encoding the protein in a host cell such as *E. coli*.

An expressed fluorescent protein of the present invention, or variant thereof, can be operatively linked to a first polypeptide of interest, further can be linked to a second polypeptide of interest, for example, a peptide tag, which can be used to facilitate isolation of the fluorescent protein variant, including any other polypeptides linked thereto. For example, a polyhistidine tag containing, for example, six histidine residues, can be incorporated at the N-terminus or C-terminus of the fluorescent protein (or variant thereof), which then can be isolated in a single step using nickel-chelate chromatography. Additional peptide tags, including a c-myc peptide, a FLAG epitope, or any other ligand, including any peptide epitope (or antibody, or antigen binding fragment thereof, that specifically binds the epitope are well known in the art and similarly can be used (see, e.g., Hopp et al. (1988). *Biotechnology* 6, pp. 1204; U.S. Pat. No. 5,011,912).

Kits

The present invention is also directed to kits, in order to facilitate and/or standardize use of compositions provided by the present invention, as well as to facilitate the methods of the present invention. Materials and reagents to carry out these various methods can be provided in kits to facilitate execution of the methods. As used herein, the term "kit" is used in reference to a combination of articles that facilitate a process, assay, analysis or manipulation.

Kits can contain chemical reagents (e.g., polypeptides or polynucleotides) as well as other components. In addition, kits of the present invention can also include, for example but not limited to, apparatus and reagents for sample collection and/or purification, apparatus and reagents for product collection and/or purification, reagents for bacterial cell transformation, reagents for eukaryotic cell transfection, previously transformed or transfected host cells, sample tubes, holders, trays, racks, dishes, plates, instructions to the kit user, solutions, buffers or other chemical reagents (e.g., oligonucleotide primers), suitable samples to be used for standardization, normalization, and/or control samples. Kits of the present invention can also be packaged for convenient storage and safe shipping, for example, in a box having a lid.

In some embodiments, for example, kits of the present invention can provide a fluorescent protein of the invention, a polynucleotide vector (e.g., a plasmid) encoding a fluorescent protein of the invention (including variant(s) thereof), bacterial cell strains suitable for propagating the vector, and reagents for purification of expressed fusion proteins. Alternatively, a kit of the present invention can provide the reagents necessary to conduct mutagenesis of fluorescent proteins isolated from Scleractinia, in order to generate a fluorescent protein variant of the present invention having a novel biophysical or biochemical property.

A kit can contain one or more compounds of the invention, for example, one or a plurality of fluorescent proteins or variants, which can be a portion of a fusion protein, or one or a plurality of polynucleotides that encode the polypeptides. The fluorescent protein variant can be a mutated fluorescent protein having a fluorescent emission spectrum at a wavelength different than the native protein. In one embodiment, the kit comprises a plurality of fluorescent protein variants, or at least one isolated fluorescent protein of the present invention, and reagents sufficient to carry out site directed mutagenesis.

A kit of the invention also can contain one or a plurality of recombinant nucleic acid molecules, which encode, in part or full, a fluorescent protein of the present invention or variant thereof, and can further include, for example, an operatively linked second polynucleotide containing or encoding a restriction endonuclease recognition site or a recombinase recognition site, or any polypeptide of interest. In addition, the kit can contain instructions for using the components of the kit, particularly the compositions of the invention that are contained in the kit.

Such kits can be particularly useful where they provide a plurality of different fluorescent proteins or variants because the artisan can conveniently select one or more proteins having the fluorescent properties desired for a particular application. Similarly, a kit containing a plurality of polynucleotides encoding different fluorescent protein variants provides numerous advantages. For example, the polynucleotides can be engineered to contain convenient restriction endonuclease or recombinase recognition sites, thus facilitating operative linkage of the polynucleotide to a regulatory element or to a polynucleotide encoding a polypeptide of interest or, if desired, for operatively linking two or more the polynucleotides encoding the fluorescent protein variants to each other.

Uses of Disclosed Fluorescent Proteins

An isolated fluorescent protein of the present invention (i.e., isolated from Scleractinia), or variant of the isolated protein, is useful in any method that employs a fluorescent protein. Thus, the fluorescent proteins and variants, are useful as fluorescent markers in the many ways fluorescent markers already are used, including, for example, coupling fluorescent protein variants to antibodies, polynucleotides or other receptors for use in detection assays such as immunoassays or hybridization assays, to track the movement of proteins in cells, or for the identification of protein-protein interactions, or protein-small molecule interactions.

For intracellular tracking studies, a first polynucleotide encoding the fluorescent protein variant is fused to a second polynucleotide encoding a protein of interest and the construct, if desired, can be inserted into an expression vector. Upon expression inside the cell, the protein of interest can be localized based on fluorescence, without concern that localization of the protein is an artifact caused by oligomerization of the fluorescent protein component of the fusion protein. In one embodiment of this method, two proteins of interest independently are fused with two fluorescent protein variants that have different fluorescent characteristics. This allows for the tracking of two proteins simultaneously.

The isolated fluorescent proteins and variants of this invention are useful in systems to detect induction of transcription. For example, a nucleotide sequence encoding an isolated Scleractinia fluorescent protein or variant can be fused to a promoter or other expression control sequence of interest, which can be contained in an expression vector. The construct can be transfected into a cell, and induction of the promoter (or other regulatory element) can be measured by detecting the presence or amount of fluorescence, thereby allowing a means to observe the responsiveness of a signaling pathway from receptor to promoter.

Fluorescent proteins and variants of the invention also are useful in applications involving fluorescence resonance energy transfer (FRET), which can detect events as a function of the movement of fluorescent donors and acceptors towards or away from each other. One or both of the donor/acceptor pair can be a fluorescent protein of the present invention (or variant(s) thereof). Such a donor/acceptor pair provides a wide separation between the excitation and emission peaks of the donor, and provides good overlap between the donor emission spectrum and the acceptor excitation spectrum.

FRET can be used to detect cleavage of a substrate having the donor and acceptor coupled to the substrate on opposite sides of the cleavage site. Upon cleavage of the substrate, the donor/acceptor pair physically separate, eliminating the energy transfer, and therefore the fluorescence emission of the acceptor molecule. Such an assay can be performed, for example, by contacting the substrate with a sample, and determining a qualitative or quantitative change in FRET (see, e.g., U.S. Pat. No. 5,741,657). A fluorescent protein or variant donor/acceptor pair also can be part of a fusion protein coupled by a peptide having a proteolytic cleavage site (see, e.g., U.S. Pat. No. 5,981,200). FRET also can be used to detect changes in potential across a membrane. For example, a donor and acceptor can be placed on opposite sides of a membrane such that one translates across the membrane in response to a voltage change, thereby producing a measurable FRET (see, e.g., U.S. Pat. No. 5,661,035).

In other embodiments, fluorescent proteins and variants of the invention are useful for making fluorescent biosensors for protein kinase and phosphatase activities or indicators for small ions and molecules such as $Ca^{2+}$, $Zn^{2+}$, cyclic 3',5'-adenosine monophosphate, and cyclic 3',5'-guanosine monophosphate. In these embodiments, the fluorescence emission of a protein of the present invention is correlated with the protein kinase or phosphatase activity, respectively.

Fluorescence in a sample generally is measured using a fluorimeter, wherein excitation radiation from an excitation source having a first wavelength, passes through excitation optics, which cause the excitation radiation to excite the sample. In response, a fluorescent protein variant in the sample emits radiation having a wavelength that is different from the excitation wavelength. Collection optics then collect the emission from the sample. The device can include a temperature controller to maintain the sample at a specific temperature while it is being scanned, and can have a multi-axis translation stage, which moves a microtiter plate holding a plurality of samples in order to position different wells to be exposed. The multi-axis translation stage, temperature controller, auto-focusing feature, and electronics associated with imaging and data collection can be managed by an appropriately programmed digital computer, which also can transform the data collected during the assay into another format for presentation. This process can be miniaturized and automated to enable screening many thousands of compounds in a high throughput format. These and other methods of performing assays on fluorescent materials are well known in the art (see, e.g., Lakowicz, "Principles of Fluorescence Spectroscopy" (Plenum Press 1983); Herman, "Resonance energy transfer microscopy" In "Fluorescence Microscopy of Living Cells in Culture" Part B, Meth. Cell Biol. 30:219-243 (ed. Taylor and Wang; Academic Press 1989); Turro, "Modern Molecular Photochemistry" (Benjamin/Cummings Publ. Co., Inc. 1978), pp. 296-361, each of which is incorporated herein by reference).

A fluorescent protein can be linked to a molecule directly or indirectly, using any linkage that is stable under the conditions to which the protein-molecule complex is to be exposed. Thus, the fluorescent protein and molecule can be linked via a chemical reaction between reactive groups present on the fluorescent protein and molecule, or the linkage can be mediated by linker moiety, which contains reactive groups specific for the fluorescent protein and the molecule. It will be recognized that the appropriate conditions for linking the fluorescent protein of the present invention and the molecule are selected depending, for example, on the chemical nature of the molecule and the type of linkage desired. Where the molecule is a polypeptide, a convenient means for linking a fluorescent protein variant and the molecule is by expressing them as a fusion protein from a recombinant nucleic acid molecule, which comprises a polynucleotide encoding, for example, an isolated coral reef fluorescent protein operatively linked to a polynucleotide encoding the polypeptide molecule.

A method of identifying an agent or condition that regulates the activity of an expression control sequence also is provided. Such a method can be performed, for example, by exposing a recombinant nucleic acid molecule, which includes a polynucleotide encoding a fluorescent protein variant operatively linked to an expression control sequence, to an agent or condition suspected of being able to regulate expression of a polynucleotide from the expression control sequence, and detecting fluorescence of the fluorescent protein variant due to such exposure. Such a method is useful, for example, for identifying chemical or biological agents, including cellular proteins, which can regulate expression from the expression control sequence, including cellular factors involved in the tissue specific expression from the regulatory element. As such, the expression control sequence can be a transcription regulatory element such as a promoter, enhancer, silencer, intron splicing recognition site, polyadenylation site, or the like; or a translation regulatory element such as a ribosome binding site.

The fluorescent proteins and variants of the invention also are useful in a method of identifying a specific interaction of a first molecule and a second molecule. Such a method can be performed, for example, by contacting the first molecule, which is linked to a donor first fluorescent protein, and the second molecule, which is linked to an acceptor second fluorescent protein, under conditions that allow a specific interaction of the first molecule and second molecule; exciting the donor; and detecting fluorescence or luminescence resonance energy transfer from the donor to the acceptor, thereby identifying a specific interaction of the first molecule and the second molecule. The conditions for such an interaction can be any conditions under which is expected or suspected that the molecules can specifically interact. In particular, where the molecules to be examined are cellular molecules, the conditions generally are physiological conditions. As such, the method can be performed in vitro using conditions of buffer, pH, ionic strength, and the like, that mimic physiological conditions, or the method can be performed in a cell or using a cell extract.

The first and second molecules can be cellular proteins that are being investigated to determine whether the proteins specifically interact, or to confirm such an interaction. Such first and second cellular proteins can be the same, where they are being examined, for example, for an ability to oligomerize, or they can be different where the proteins are being examined as specific binding partners involved, for example, in an intracellular pathway. The first and second molecules also can be a polynucleotide and a polypeptide, for example, a polynucleotide known or to be examined for transcription regulatory element activity and a polypeptide known or being tested for transcription factor activity. For example, the first molecule can comprise a plurality of nucleotide sequences, which can be random or can be variants of a known sequence, that are to be tested for transcription regulatory element activity, and the second molecule can be a transcription factor, such a method being useful for identifying novel transcription regulatory elements having desirable activities.

The present invention also provides a method for determining whether a sample contains an enzyme, e.g., a protein kinase or phosphatase. Such a method can be performed, for example, by contacting a sample with a tandem fluorescent protein disclosed herein (including a variant fluorescent protein); exciting the donor, and determining a fluorescence property in the sample, wherein the presence of an enzyme in the sample results in a change in the degree of fluorescence resonance energy transfer. Similarly, the present invention relates to a method for determining the activity of an enzyme in a cell. Such a method can be performed, for example, providing a cell that expresses a tandem fluorescent protein construct, wherein the peptide linker moiety comprises a cleavage recognition amino acid sequence specific for the enzyme coupling the donor and the acceptor; exciting said donor, and determining the degree of fluorescence resonance energy transfer in the cell, wherein the presence of enzyme activity in the cell results in a change in the degree of fluorescence resonance energy transfer.

Also provided is a method for determining the pH of a sample. Such a method can be performed, for example, by contacting the sample with a first fluorescent protein of the invention, wherein the emission intensity of the first fluorescent protein changes as pH varies between pH 5 and pH 10, and in some embodiments, varies between pH6 and pH9, and in some specific embodiments, varies between pH6.3 and pH8.5; exciting the indicator; and determining the intensity of light emitted by the first fluorescent protein at a first wavelength, wherein the emission intensity of the first fluorescent protein indicates the pH of the sample. The first fluorescent protein useful in this method can comprise a polypeptide sequence as set forth in any one of SEQ ID NOS: 10, 12, 14, 16, 18, 20, 22, 24, 26, 28, 30, 32, 34, 36, 38, 40, 42 or 44. Alternatively, the protein can comprise an amino acid sequence with at least 80% identity, or at least 85% identity, or at least 90% identity, or at least 95% identity with one or more of the sequences set forth in SEQ ID NOS: 10, 12, 14, 16, 18, 20, 22, 24, 26, 28, 30, 32, 34, 36, 38, 40, 42 or 44. In a specific embodiment, the method utilizes the fluorescent protein having the amino acid sequence set forth in SEQ ID NO: 10.

The sample used in a method for determining the pH of a sample can be any sample, including, for example, a biological tissue sample, or a cell or a fraction thereof.

Cell-Based Method for Detecting Kinase and Phosphatase Modulators

In a further aspect, the invention provides a cell-based method for detecting kinase and phosphatase activities, and for detecting kinase and phosphatase modulators. The method is based on the surprising discovery that one or more fluorescent characteristics of a fluorescent protein disclosed herein are modulated by phosphorylation. The method utilizes a genetically encoded fluorescent protein which, when expressed within living cells, exhibits a change in a fluorescent characteristic concordant with the temporal and spatial activity of a kinase or phosphatase of interest.

This method of the invention provides a powerful cellular screening platform for new drugs to target kinases and phosphatases. Cell-based phosphorylation detection platforms to screen for kinase and phosphatase modulators offer significant advantages to current strategies that involve purified reagents. For instance, considerable effort has been made to determine protein kinase structures in order to synthesize chemical inhibitors. Cell-based screening for kinase and phosphatase inhibitors has the potential to lead to the discovery of compounds with mechanisms that are either not apparent from the kinase structure, or not dependent on the protein kinase alone. Another advantage to a cell-based detection approach is that the problem of cell membrane permeability and access to the kinase and phosphatase is automatically addressed by the design of the approach. Further, a cell-based detection approach permits identification of any undesirable effects a compound may have, e.g., undesirable effects on other molecules within the cell (such as related kinases and phosphotases) that may cause, e.g., apoptosis, which would not be detected by assays using purified kinases or phosphatases, and reagents. Cell-based phosphorylation detection platforms provided by the invention also offer significant advantages over assays which detect activities of specific kinases and phosphatases within cells using phosphorylation state-specific antibodies, which are typically performed in Western Blot or ELISA format (see, e.g., Nairn et al., *Nature* 299, 734-736, 1982). Such antibody-based phosphorylation assays only provide a "snapshot" of the dynamic process of phosphorylation within cells, which involves both kinase and phosphatase activities, and are also expensive and difficult to scale up for purposes of drug screening.

In accordance with the present invention, a cell-based detection method utilizes host cells that express a protein kinase or phosphatase of interest and a fluorescent protein, wherein one or more fluorescent characteristics of the fluorescent protein change upon phosphorylation by the kinase or phosphatase. Such host cells are contacted with a candidate compound under conditions that permit phosphorylation of the fluorescent protein by the kinase or phosphatase, and the compound is identified as an modulator of the kinase or phosphatase if the compound causes any alteration in the change of a fluorescent characteristic of the fluorescent protein upon phosphorylation in the presence of the compound as compared to in the absence of the compound.

The term "modulator" as used herein refers to a molecule that modulates, directly or indirectly, the activity of a protein kinase or phosphatase. A modulator includes both molecules that enhance and molecules that inhibit, directly or indirectly, the activity of a protein kinase or phosphatase. In some embodiments, the cell-based detection method of the invention is directed to identifying inhibitors of a protein kinase or phosphatase of interest.

The cell-based detection method of the invention can be applied to screen for modulators of a wide array of protein kinases, including serine kinases, threonine kinases, and tyrosine kinases. Examples of protein kinases suitable for use in accordance with the present invention include, but not limited to, Akt1, Akt2, Akt3, VEGF, Src, MET, KIT, ERBB2, FAK, PKA, PKC, PKG, PKD, MAPK (such as MAPK4, MAPK6, MAPK7, MAPK8, MAPK9, MAPK10, MAPK11, MAPK12, MAPK13, MAPK14, and MAPK15), cdc2, CDK, ERK2, CK1, CK2, GSK3, CaMK1, CaMK2, CaMK4, ABL, EGFR, IRK, PIM1-3, CLK1, DMPK-E, Pim1, RSK1, SLK1, ZIPK, NIMA, DCK1-b2, CHK1, MSK1/2, PAK, PDK1, LKB1, mTOR, MEK3, BARK, ATM, DNAPK, SIM, ERK1, GSK3, TGF-betaR1, TrkB, Fyn among others (see, e.g., Ubersax et al., *Nature Reviews Mol. Cell. Biol.* 8: 530-541 (2007), the content of which is incorporated herein by reference)

In a specific embodiment, the cell-based detection method is designed to identify modulators of Akt1. Akt1 is well characterized (for review, see Gonzalez and McGraw, *Cell Cycle* 8, 2502-2508, 2009), allowing testing of candidate compounds and comparison with available inhibitor compounds of Akt1.

The cell-based detection method of the invention utilizes a fluorescent protein, which exhibits a change in one or more fluorescent characteristics upon phosphorylation. As described hereinabove, the term "fluorescent property" or "fluorescent characteristic" refers to the molar extinction coefficient at an appropriate excitation wavelength, the fluorescence quantum efficiency, the shape of the excitation spectrum or emission spectrum, the excitation wavelength maximum and emission wavelength maximum, the ratio of excitation amplitudes at two different wavelengths, the ratio of emission amplitudes at two different wavelengths, the excited state lifetime, the fluorescence anisotropy, intensity of fluorescence at a particular wavelength, or the integral of fluorescence over the emission spectrum.

In some embodiments, the fluorescent characteristic that exhibits a change upon phosphorylation is the fluorescence intensity at a particular wavelength, and/or the integral of fluorescence over part or all of the emission spectrum. In these cases, the change can be measured and is indicative of the activity of a kinase or phosphatase being examined.

As used herein, the change of a fluorescent characteristic (such as change in fluoresce intensity) is considered to be significant if the change is at least 20%, or at least 30%, or at least 40%, or at least 50%, or at least 60%, or at least 70%, or at least 80%, or at least 90%, or at least 100% or greater, when comparing the measurement of the fluorescent characteristic in question in the presence of a kinase or phosphatase relative to in the absence of the kinase or phosphatase.

In specific embodiments, the fluorescence intensity at a particular wavelength and/or the integral of fluorescence over the emission spectrum is increased when the fluorescent protein is phosphorylated. Thus, detection of the increase in fluorescence intensity is indicative of the kinase or phosphatase activity.

For purposes of the cell-based assay disclosed herein, a fluorescent characteristic is being examined and detected, and the detected characteristic is correlated with a kinase or phosphatase activity. The term "correlated with", as used in this context, is meant to include a correlation where the detected characteristic (e.g., fluorescence intensity) is compared to a control value, and the difference relative to the control value is used as an indicator of the kinase or phosphatase activity, as well as a co-relation where the detection device or data processing unit has been calibrated based on a built-in control value, such that the detected characteristic or value is used directly as an indicator of a kinase or phosphatase activity.

In other embodiments, the fluorescent characteristic that exhibits a change is the shape of the excitation spectrum or emission spectrum. Changes in the emission spectrum of a fluorescent protein permit ratiometric measurements to be carried out, which allows for the development of a highly robust method for quantifying spectral change in a fluorescent protein. In some embodiments, a portion of the emission or excitation spectrum is enhanced while another portion of the emission or excitation spectrum is reduced. In such embodiments, both portions are simultaneously measured. In such embodiments, the signals produced are normalized for probe levels. In some embodiments, a single narrow excitation filter centered around 490 nm causes the emission of the probe to decrease with phosphorylation. In other embodiments, the excitation wavelength is switched between 490 nm and 420 nm to produce a ratio in which the 420 nm signal decreases and the 490 nm signal increases following phosphorylation. In some embodiments, a single narrow excitation filter centered around 490 nm causes the emission of the probe to decrease with phosphorylation. In other embodiments, switching between exciting at 490 nm and 420 nm produces a ratio in which the 420 nm signal decreases and the 490 nm increase following phosphorylation.

The cell-based kinase or phosphatase assays of the invention can be implemented using a fluorescent protein or a variant disclosed herein and above. In a specific embodiment, the assay utilizes the fluorescent protein having the amino acid sequence set forth in SEQ ID NO: 10, also referred to herein as "PhosFluor". PhosFluor has been identified in accordance with the invention as a protein that exhibits increased fluorescence intensity and an altered emission spectrum upon phosphorylation. It is believed that specific sites within the PhosFluor protein alter the excitation and emission spectrum of the protein in response to phosphorylation or dephosphorylation.

In other embodiments, the assay utilizes a variant of the PhosFluor protein which exhibits increased fluorescence intensity and an altered emission spectrum upon phosphorylation or dephosphorylation.

In one embodiment, a PhosFluor variant is generated by inserting into the naturally-occurring PhosFluor protein, one or more consensus sites for phosphorylation by a specific kinase or phosphatase, or a group of kinases or phosphatases, without necessarily replacing any of the phosphorylation sites within the naturally-occurring PhosFluor protein. Phosphorylation sites can be inserted at an internal location of the PhosFluor protein, or at the termini of the PhosFluor protein.

In eukaryotic cells, phosphorylation can occur on several amino acids within a protein, with phosphorylation on serine being the most common, followed by threonine, and with tyrosine phosphorylation being relatively rare. The term "phosphorlation consensus site" refers to a relatively short amino acid sequence motif, generally 4-10 residues, which includes a phosphoryation residue (serine, threonine or tyrosine) flanked by amino acid residues having certain characteristics (e.g., hydrophobic, polar, acidic, basic, neutral, or kink), and which sequence motif defines substrate specificity for a specific kinase or phosphatase, or group of kinases or phosphatases. For example, the concensus phosphorylation sites for Akt, PKA and Src are RXRXX(S/T) (SEQ ID NO: 46), RRX(S/T)Ø (SEQ ID NO: 47), and EEIY(E/G)XF (SEQ ID NO: 48), respectively, where X represents any amino acid and Ø represents a hydrophobic residue (Ubersax et al., *Nature Reviews Mol. Cell. Biol.* 8: 530-541 (2007)). Additionally, a number of databases are available which provide experimental verified phosphorylation sites, accessible on line, such as Phosphobase as reported by Blom et al. (*Nucleic Acids Research* 26(1): 382-386, 1998).

In another embodiment, a PhosFluor variant is generated by replacing one or more native phosphorylation sites within the naturally-occurring PhosFluor with one or more consensus phosphorylation sites for a specific kinase or phosphatase, or group of kinases or phosphatases. Such replacement engineering is believed to enhance the specificity of the resulting variant to phosphorylation by the specific kinase or phosphatase, or group of kinases or phosphatatases which recognize and acts on the phosphorylation site(s). In a specific embodiment, all of the native phosphorylation sites in PhosFluor have been replaced with the consensus phosphorylation sites for a specific kinase or phosphatase, e.g., the Akt1 kinase.

Any of the above-described PhosFluor variants can be generated using genetic engineering techniques such as, e.g., site-directed mutagenesis. Additional molecular engineering can be performed to improve solubility, folding, expression, fluorescence intensity, and monomer state in a host cell. For instance, previous studies have identified amino acid modifications that optimize protein folding of coral GFPs (Campbell et al., *Proc Natl Acad Sci USA* 99, 7877-7882, 2002). A similar approach can be taken to improve the folding of PhosFluor in host cells such as mammalian cells. Furthermore, mutations can be introduced into PhosFluor which can reduce the affinity of paired proteins with one another thereby permitting more effective spatial resolution of phosphorylation detection in cells. Another fluorescent protein isolated from warm water coral, *Cyphastrea microphthalma*, vivid Verde fluorescent protein (or "vVFP"), has been successfully monomerized based on introducing mutations into the region(s) involved in oligomerization (Hagan et al., 2010, incorporated herein by reference). The PhosFluor protein, which exhibits 68.9% identity to vVFP, can be mutated in a similar manner.

To practice the cell-based method of the invention, a variety of cells can be used as host cells, including but not limited to bacterial and eukaryotic cell lines, such as fungal, plant, avian, insect and mammalian cell lines suitable for expression of a protein kinase or phosphatase of interest and a fluorescent protein disclosed herein. In specific embodiments, the kinase or phosphatase detection method of the invention utilizes a mammalian cell line.

A host cell may express a protein kinase or phosphatase of interest at a desirable level endogenously, or may be engineered or further modified to achieve an effective expression of the protein kinase or phosphatase of interest. For example, a host cell can be transformed with an expression vector coding for the kinase or phosphatase, and expression of the kinase or phosphatase is driven by a strong promoter, which can be either inducible or constituitive. Suitable promoters include the cytomegalovirus (CMV) and retroviral long terminal-repeat (LTR) promoters. Cell lines that normally express low basal levels of protein kinases, such as NIH 3T3 cells, may be desirable to permit introduction of expression vectors that direct expression of a specific kinase. The expression vectors can, in some embodiments, be integrated into the genome of the host cell to achieve stable, high level expression of the kinase or phosphatase.

The host cell is also engineered to express a fluorescent protein disclosed herein above. This can be accomplished by conventional transformation of the host cell with an expression vector which encodes a desirable fluorescent protein, e.g., PhosFluor or a variant thereof.

Expression of a protein kinase or phosphatase of interest and a fluorescent protein may be enhanced by optimizing the codons encoding these proteins, i.e., selecting codons that are preferably used for expression in the host cells such as mammalian cells, as well as utilizing an optimized Shine-Dalgarno sequence in the expression vector. Similar methods were used to create enhanced GFP (eGFP) (Yang et al., *Nucleic Acids Res* 24, 4592-4593, 1996).

To perform a cell-based assay for detection of kinase or phosphatase activity, an appropriate host cell which expresses a protein kinase or phosphatase of interest and a fluorescent protein is monitored. A change in one or more fluorescent characteristic, e.g., an increase in fluorescence intensity within the cell, can be detected and is indicative of the spatial and temporal activity of the kinase or phosphatase. Animal models can also be developed based on such cell-based approach to detect the spatial and temporal activity of a kinase or phosphatase in vivo within an animal.

To perform a cell-based assay for screening for kinase inhibitors, an appropriate host cell which expresses a protein kinase of interest and a fluorescent protein is contacted with a candidate compound under conditions that permit phosphorylation of the fluorescent protein by the kinase. Host cells without being contacted by the compound are used as control. In cases where the fluorescent protein exhibits increased fluorescence intensity upon phosphorylation, a reduction in the increase of fluorescence intensity in the presence of the compound is indicative of an inhibitory effect of the compound on the kinase activity. As disclosed above, once properly calibrated, the fluorescence intensity detected in the presence of a compound can be correlated directly with the effect of the compound on the kinase or phosphatase activity.

To perform a cell-based assay for screening for phosphatase inhibitors, an appropriate host cell which expresses a protein phosphatase of interest and a phosphorylated fluorescent protein is contacted with a candidate compound under conditions that permit phosphorylation of the fluorescent protein. In some embodiments, the fluorescent protein is phosphorylated by a specific kinase, for example, by PKC or Src, prior to the performance of the assay. In certain embodiments, the host cell expresses a exogenous kinase, for example, PKC or Src. The phosphorylated fluorescent protein is contacted with a candidate compound under conditions that permit dephosphorylation of the phosphorylated fluorescent protein by the phosphatase. Host cells without being contacted by the compound are used as control. In cases where the fluorescent protein exhibits increased fluorescence intensity upon phosphorylation, a decline in the decrease of fluorescence intensity in the presence of the compound is indicative of an inhibitory effect of the compound on the phosphatase activity. As disclosed above, once properly calibrated, the fluorescence intensity detected in the presence of a compound can be correlated directly with the effect of the compound on the phosphatase activity.

In a specific embodiment, the cell-based assay of the invention is performed in an array or multiwall format, which allows high throughput screening of combinatorial libraries for kinase or phosphatase inhibitors. In this embodiment, cells expressing both a protein kinase or phosphatase of interest and a fluorescent protein (e.g., the PhosFluor protein or variant) are plated onto a multi-well grid. Compounds are then added to the wells to test for kinase or phosphatase inhibition, followed with an addition of a stimulus that triggers the phosphorylation or dephosphorylation reaction, or without addition of such stimulus (as control). Suitable stimuli include cyclic AMP (cAMP) and brain-derived neurotrophic factor (BDNF). Fluorescence is used as the readout of kinase or phosphatase activity. Both the $IC_{50}$ and kinetic data (based on fluorescence over time) can be obtained from such an assay.

In one embodiment, the assay is performed in vivo, i.e. within an intact animal. In this embodiment, cells of the animal express both a protein kinase or phosphatase of interest and a fluorescent protein. The cells of the animal are then contacted with one or more compounds to test for kinase or phosphatase inhibition. The cells of the animal are contacted with a stimulus that triggers the phosphorylation or dephosphorylation reaction, or without addition of such stimulus (as control). Suitable stimuli include cyclic AMP (cAMP) and brain-derived neurotrophic factor (BDNF). Fluorescence is used as the readout of kinase or phosphatase activity. Both the $IC_{50}$ and kinetic data (based on fluorescence over time) can be obtained from such an assay.

The present invention is further illustrated by reference to the following Examples. However, it should be noted that these Examples, like the embodiments described above, are illustrative and are not to be construed as restricting the enabled scope of the invention in any way.

EXAMPLE 1 cDNA Synthesis, Cloning, Isolation and Sequencing of Disclosed Fluorescent Proteins Biological samples were isolated from organisms of the order Scleractinia, found in the Australian Great Barrier Reef.

Methods for RNA extraction, cDNA synthesis, and specific cloning of fluorescent proteins from the Australian Great Barrier Reef and *Montastrea cavernosa* have been described previously (Kao et al. (2007). *Mar Biotechnol*. (NY) 9, pp. 733-746).

A set of degenerate primers was used to amplify a conserved region of each fluorescent molecule. The degenerate primers comprising the nucleotide sequences set forth in SEQ ID NOs: 1-5 (1 µM total concentration with each primer present in equimolar concentrations) were used for the 5' end.

The degenerate primers comprising the nucleotide sequences set forth in SEQ ID NOs: 6-9 (at 1 µM total concentration with each primer present in equimolar concentrations) were used for the 3' end.

For each of the primers comprising the nucleotide sequences set forth in SEQ ID NO: 1-9, "B"=G, C or T; "K"=G or T; "M"=A or C; "N"=A, C, G or T; "R"=A or G; "S"=G or C; "W"=A or T; "Y"=C or T.

The degenerate primers were used to amplify cDNA derived from the coral specimens, and the resulting DNAs were cloned into pCR4Blunt-TOPO (Invitrogen, Carlsbad, Calif.) and sequenced. Sequences that were homologous to previously known fluorescent proteins were used to design internal primers for amplifying the entire cDNA.

The internal primers were used in inverse PCR assays to obtain the full length clones (Kuniyoshi, Fukui, and Sakai (2006), *Biosci. Biotechnol. Biochem.* 70, pp. 1983-1986).

Fluorescent proteins were constitutively expressed in pCR4Blunt-TOPO (Invitrogen, Carlsbad, Calif.). Expression was visualized by plating bacteria onto CircleGrow agar plates (MP Biomedicals, Irvine, Calif.) supplemented with kanamycin (20 µg/mL) and charcoal (2% w/v) to suppress endogenous fluorescence from bacterial media. Colonies were visualized using Illumatool (Lightools Research, Encinitas, Calif.).

Sequences and Alignment

The Australian Great Barrier Reef fluorescent proteins in this study were obtained from sequencing and from GenBank. The nucleotide sequences encoding the disclosed fluorescent polypeptides are set forth in SEQ ID NOs: 11, 13, 15, 17, 19, 21, 23, 25, 27, 29, 31, 33, 35, 37, 39, 41, 43, and 45. The amino acid sequences encoding the disclosed fluorescent polypeptides are set forth in SEQ ID NOs: 10, 12, 14, 16, 18, 20, 22, 24, 26, 28, 30, 32, 34, 36, 38, 40, 42, and 44.

For the nucleotide sequences, the upper case letters denote the coding sequence. The novel amino acid and nucleotide sequences of the present invention were collated and aligned with the sequences of known fluorescent proteins using MAFFT default settings (Katoh et al. (2005), *Nucleic Acids Res.* 33, pp. 511-518). While some gaps were observed in the alignment in the N terminal region, most of the protein is trivial with respect to alignment (see FIG. 1).

EXAMPLE 2

Phylogenetic Tree Generation for the Disclosed Fluorescent Proteins

All phylogenetic trees were generated using PAUP* (Swofford (2000), *PAUP*. Phylogenetic Analysis Using Parsimony (* and Other Methods)*. Version 4. Sinauer Associates, Sunderland, Mass.). Standard parsimony settings were used in all analyses, and robustness was assessed with bootstrap and jackknife analyses as well as Bayesian approaches using MrBayes (using the parsmodel option). In general, trees generated were well resolved and supported despite the small number of characters present (45 for the conserved chromophore regions and 225 for the flanking non-chromophore regions) in each of the partitioned matrices.

The phylogenetic matrix was partitioned using the charset option in PAUP*. The interior potential chromophore region was partitioned into 40 residue sliding windows as indicated in the charpar partitions. The congruence of each of these internal sliding windows as well as the congruence of the N terminal end with the C terminal end was determined using the "hompart" option in PAUP* utilizing 100 random partitioning steps.

Figure 2B:
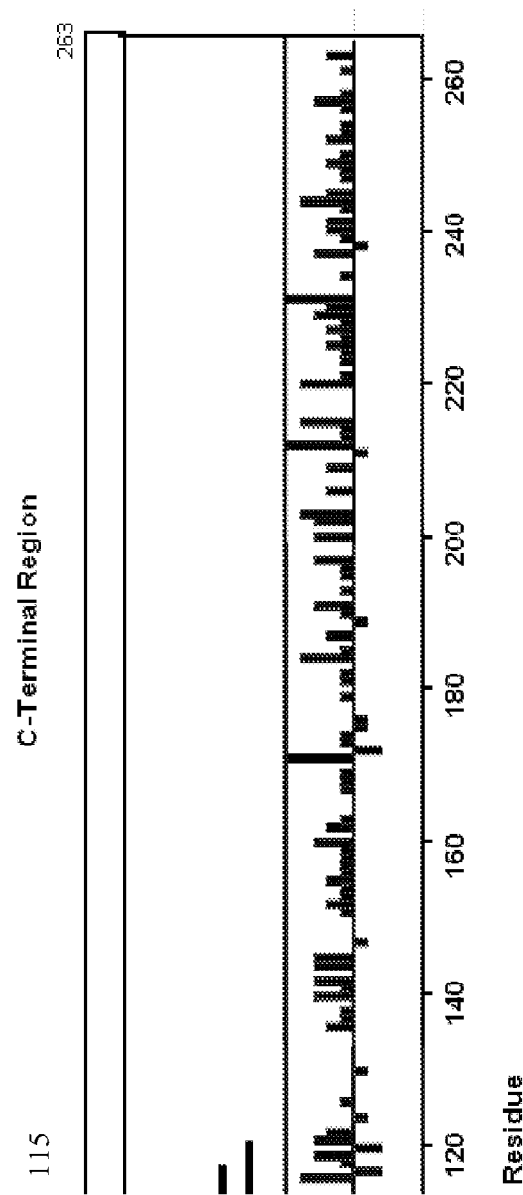

Molecular evolutionary analysis of the novel polypeptides of the present invention, and 74 additional fluorescent protein sequences (encompassing fluorescent protein sequences derived from organisms of the order Scleractinia, of the order Actiniaria, of the order Corallimorpharia, of the order Ceriantharia, of the order Hydroida, of the subclass Copepoda, and of the order Amphioxus) of known geographic origin revealed a conserved region located approximately in the middle of the molecule that includes the light-emitting tripeptide chromophore (e.g., for eGFP, Ser65-Tyr66-Gly67) (see FIGS. 1, 2 and 5).

Molecular phylogenetic analyses were then undertaken by partitioned analysis of the conserved region and the remainder of the protein. The initial analyses using the incongruence length difference (ILD) test revealed distinct evolutionary processes at work on a central conserved region and two flanking regions (null hypothesis of congruence is rejected at $p>0.25$).

The analysis was repeated by sliding a 40 amino acid window (representing the potential boundary size of the region) in the carboxyl direction by 5 amino acid increments (see FIG. 2) to precisely locate the boundary of the interior conserved region. This revealed a distinct central region, demarcated by residues 70 to 115 (see FIGS. 1 and 2; residues correspond to sequence alignment shown in FIG. 1). The central region displays a sharply divergent evolutionary pattern from the rest of the protein (ILD test; $p>0.25$). The central region evolves slowly under stabilizing selection. Consistent with this finding, the rate of molecular change in this middle conserved region is much slower than the terminal regions (relative ratio of rates of terminal regions to the middle conserved region range from 1.68 to 1.77 depending on input criteria). This central region consists of the chromophore containing a helix and a single β strand. The β strand faces inward in the tetrameric fluorescent complex (see FIG. 3).

The terminal regions are under intense Darwinian selection and evolve rapidly with mutations appearing at sites of putative protein-protein interactions (see FIG. 4), with no difference observed between the amino and carboxyl regions (ILD test; $p<0.01$). In addition, phylogenetic trees generated from the middle region and from the combined terminal regions revealed that fluorescence color is significantly associated with the terminal hypervariable regions and not with the middle conserved region (KH test—$p<0.013$-$0.039$; Templeton test—$p<0.022$-$0.039$; marginal significance winning site test $p<0.071$-$0.125$).

The results indicate that the fluorescent proteins analyzed herein possess two regions under distinct molecular evolutionary pressures. When aligned to the crystal structure, residues undergoing rapid evolution map to a single patch on the exterior of the tetramer and point outward (see FIG. 4). By contrast, the middle conserved region contains the chromophore followed by a single beta-strand, part of which forms a pocket or channel (see FIGS. 3 and 4) in the center of the tetrameric structure.

However this central conserved region does not appear to contain those residues necessary for tetramerization of fluorescent proteins. Based on the sequence of the entire protein, fluorescent separate on the basis of color (Ugalde, Chang, and Matz (2004), *Science* 305, p. 1433; Field et al. (2006), *J. Molecular Evolution* 62, pp. 332-U315; Kao et al. (2007). *Mar Biotechnol* (NY) 9, pp. 733-746). However, only the terminal hypervariable regions of fluorescent proteins, which do not include the chromophore, track with color evolution. Conversely, the region containing the chromophore, evolves independently from the rest of the protein and does not track fluorescence color (see FIG. 2).

For a class of compact protein appreciated mainly for its chromatic properties, fluorescent proteins contain distinct regions—one containing the chromophore (45 internal residues) and the other enclosing it (50 residues on the N terminus and 140 residues on the C terminus)—with sharply contrasting evolutionary behavior largely unrelated to chromatic properties. The highly divergent and externally facing terminal regions are likely involved in protein-protein interactions with a highly variable protein of external origin. In addition there are additional hypermutable sites (19 sites; FIGS. 4 and 5) in this region, consistent with the findings of Field et al., who reported 11 hypermutable sites (Field et al. (2006), *J. Molecular Evolution* 62, pp. 332-U315).

EXAMPLE 3

Determination of Surface Residues of the Disclosed Fluorescent Polypeptides The amino acid sequences of the disclosed fluorescent polypeptides, as well as sequences of other fluorescent proteins, were aligned to the structure of nidogens, a family of extracellular matrix proteins that unexpectedly displayed a nearly identical crystal structure to that of fluorescent proteins (Hopf, et. al. (2001). *Nat. Struct. Biol.* 8, pp. 634-640). The N-terminal hypervariable amino acids of fluorescent proteins form a surface patch that closely aligns with the conserved binding region of the nidogens (see FIG. 5).

Alignment of amino acid sequences of the disclosed fluorescent polypeptides with the globular extracellular region of nidogens reveals that the N-terminal hypervariable amino acids of the respective fluorescent polypeptide forms a surface patch that closely aligns with the conserved binding region of the nidogens. This conserved nidogen region is the surface that interacts with perlecans, the major protein binding partner of nidogens (Kvansakul et al. (2001). *EMBO* 20, pp. 5342-5346). Accordingly, a main function of the hypervariable terminal regions of the fluorescent proteins disclosed herein may be to bind to other protein targets.

EXAMPLE 4

Comparison of a Disclosed Fluorescent Polypeptide with eGFP

The fluorescence emission of a disclosed fluorescent polypeptide having the amino acid sequence set forth in SEQ ID NO: 24 was compared to eGFP. eGFP is one of the brightest fluorescent proteins created to date. Both the disclosed fluorescent polypeptide having the amino acid sequence set forth in SEQ ID NO: 24 and eGFP were cloned into a modified pET-HT vector with a TEV-cleavable His-tag, expressed in BL21-DE3 *E. coli*, and purified via Ni-NTA resin. The concentration of each sample was normalized by the intensity of the respective absorption spectrum at 480 nm.

Figure 6:
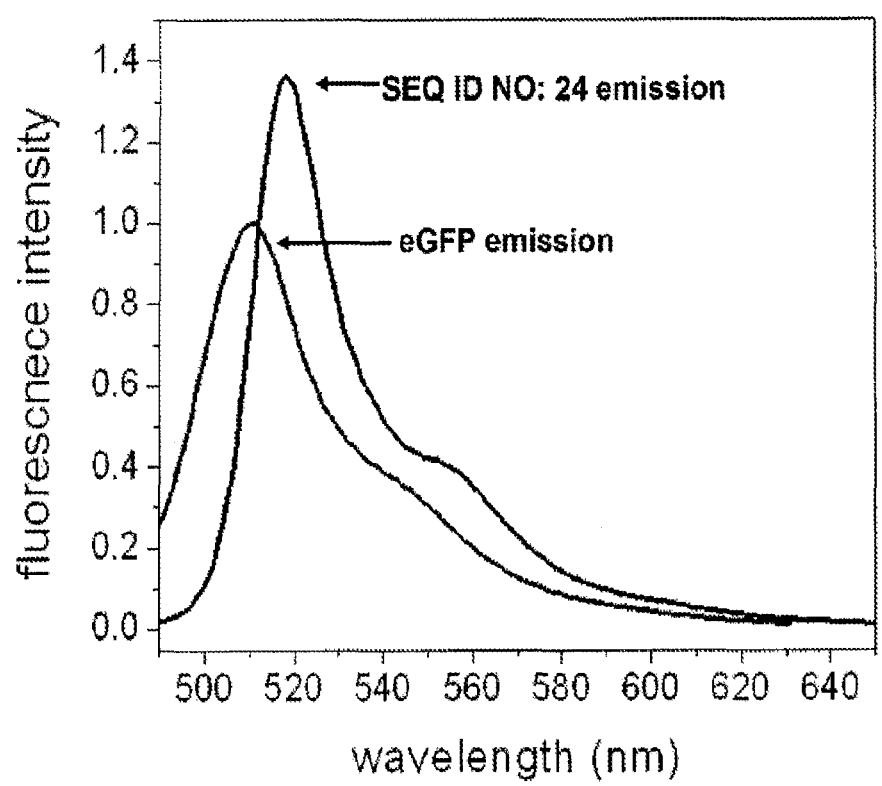
FIG. 6 shows the emission spectra of both eGFP and the fluorescent polypeptide comprising the sequence set forth in SEQ ID NO: 24.

Fluorescence correlation spectroscopy (FCS) measurements (not shown) also indicated the protein having the sequence set forth in SEQ ID NO: 24 is monomeric and about 1.4 times as bright as eGFP. Additionally, as FIG. 6 clearly indicates, the peak emission intensity of the disclosed fluorescent polypeptide having the amino acid sequence set forth in SEQ ID NO: 24 is about 50% greater than that of eGFP.

EXAMPLE 5

Maturation Kinetics of the Disclosed Fluorescent Polypeptides

Figure 7:
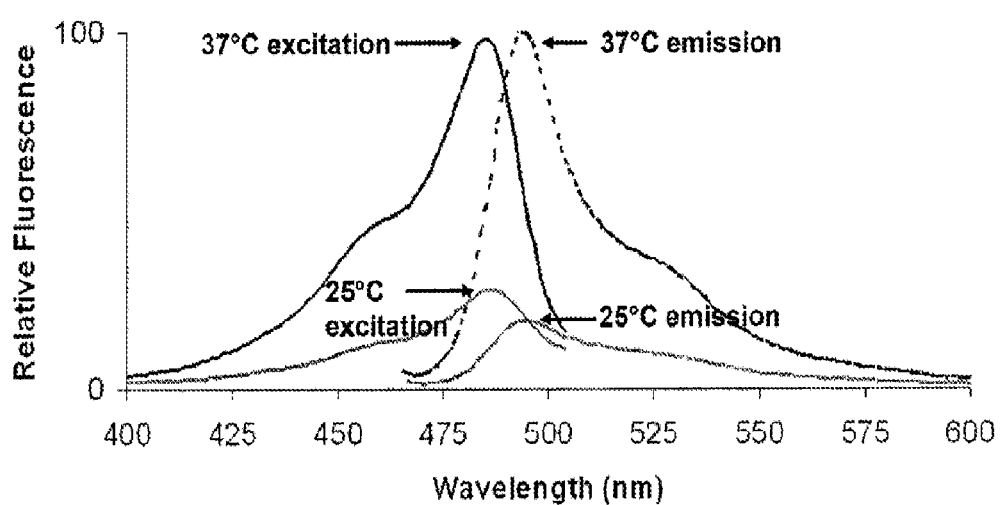
FIG. 7 shows the emission and excitation spectra at 25° C. and 37° C. for the isolated fluorescent polypeptide comprising the sequence set forth in SEQ ID NO: 12.
Figure 8:
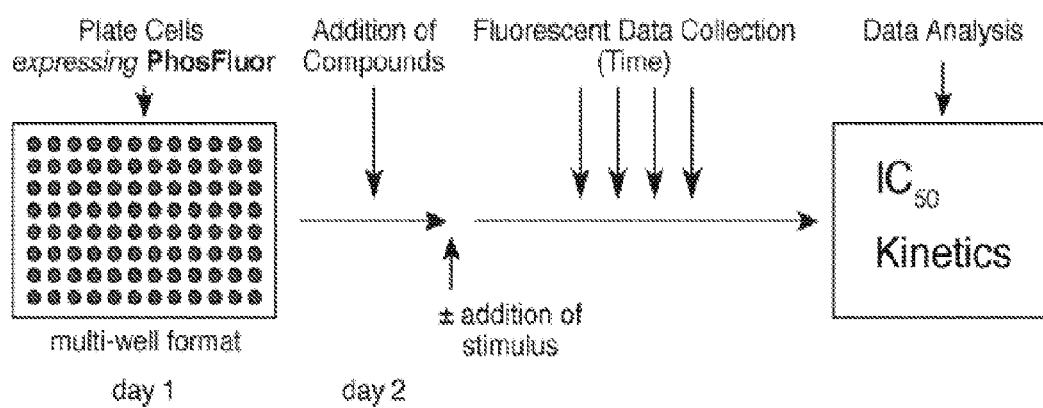
FIG. 8 sets forth a schematic diagram of a disclosed method. Cells expressing both a protein kinase of interest and PhosFluor (the PhosFluor Detection System) are plated onto a multi-well grid for compound screening. Compounds are then added to the wells to test for kinase inhibition, in the presence or absence of a stimulus. Fluorescence is used as the readout of kinase activity. Both the IC50 and kinetic data can be obtained using this system.

The kinetics of maturation of the disclosed fluorescent polypeptide having the amino acid sequence set forth in SEQ ID NO: 12 were monitored in *E. coli* grown at two different temperatures (25° C. and 35° C.). FIG. 7 shows the excitation and emission spectra, measured under identical conditions, and normalized to absorbance at 600 nm (i.e., an equal number of cells) for the proteins grown at both 25° C. and 37° C. Distinct, high peaks were seen for the sample grown at 37° C., in contrast to the 25° C. sample. This indicates that the disclosed fluorescent polypeptide having the amino acid sequence set forth in SEQ ID NO: 12 grown at 37° C. is soluble and correctly folded.

EXAMPLE 6

PhosFluor Exhibited Fluorescence Modulation in Response to Alkaline pH

It was hypothesized that a single fluorescent protein could exhibit altered fluorescence when phosphorylated, and that such proteins could exist in nature. Phosphorylation bestows a phosphate group to a protein, rendering additional negative charge and a more basic isoelectric point. Since this is roughly equivalent to creating a basic environment for the protein, it was reasoned that proteins exhibiting a change of fluorescence with basic pH could be engineered into phosphorylation sensors.

One of the earliest examples of a pH-sensitive fluorescent protein is pHluorin, an engineered fluorescent protein that exhibits very low or no fluorescence below pH 6, but bright fluorescence at pH 7 (Miesenbock et al., 1998). When pHluorins (also known as SynaptopHluorins) are engineered to reside within acidic organelles (e.g. vesicles of lysosomes) no fluorescence is detected until the organelle is brought to a neutral pH. Thus, pHluorins fluoresce when vesicles or lysosomes are discharged, providing a fluorescent readout of a physiological process. It was believed, however, that there are no proteins that exhibit increased fluorescence with basic pH.

A panel of fluorescent proteins was subjected to different pH conditions. As shown in FIG. 9A, PhosFluor (the fluorescent protein having the amino acid sequence set forth in SEQ ID NO: 10) exhibited >100% increase in brightness from pH 6.3 to pH 8.5. By contrast, none of the other proteins, including Green Fluorescent Protein (GFP) or its derivatives, enhanced GFP (eGFP), CFP or YFP, or another coral protein (vVFP) exhibited any change in fluorescence intensity at basic pH (FIG. 9A).

EXAMPLE 7

PhosFluor Underwent Dramatic Spectral Changes when Phosphorylated

Analyses of the PhosFluor protein suggest that several sites within the molecule are strong substrates for many different protein kinases (Blom et al., *J Mol Biol* 294, 1351-1362, 1999), particularly protein kinase C (PKC). Indeed, Western blot analyses revealed that serine and threonine sites on PhosFluor are phosphorylated by PKA, PKC, mitogen-activated protein kinase (MAPK), cell division control protein 2 (cdc2), and Akt1.

To determine if the fluorescence of PhosFluor could be modulated by phosphorylation, recombinant PhosFluor was incubated with different protein kinases and fluorescence was monitored (FIG. 9B). PhosFluor demonstrated a dramatic increase in fluorescence intensity when treated with various protein kinases, consistent with the increased brightness of this molecule when exposed to alkaline pH (FIG. 9A). eGFP, one of the most widely used fluorescent proteins, showed no change in fluorescence intensity when incubated with kinases (FIG. 9B). However, fluorescence intensity also increased to a lesser degree in the absence of added protein kinase. It was thought that endogenous bacterial protein kinases were expressed in *E. coli* (Enami and Ishihama, *J Biol Chem* 259, 526-533, 1984); therefore PhosFluor was incubated in the presence of alkaline phosphatase to remove phosphate groups. This treatment virtually abolished the increase in fluorescence intensity of PhosFluor over time (FIG. 9B). The fluorescence intensity of PhosFluor also increased above background levels when the protein was incubated with cdc2 and MAPK (data not shown). Collectively, these experiments demonstrate that PhosFluor increases its fluorescence intensity upon phosphorylation.

Phosphorylation is known to increase the negative charge on proteins, which commonly results in an upward shift in the apparent molecular weight of the protein when resolved by SDS-PAGE (sodium dodecyl sulfate-polyacrylamide gel electrophoresis). Indeed, when phosphorylated by PKC, multiple higher molecular weight species of PhosFluor were resolved by SDS-PAGE (FIG. 9C), indicating that several sites on this molecule were phosphorylated by this protein kinase. To a lesser extent, higher molecular weight species were also observed upon phosphorylation by PKA (FIG. 9C).

Figure 10:
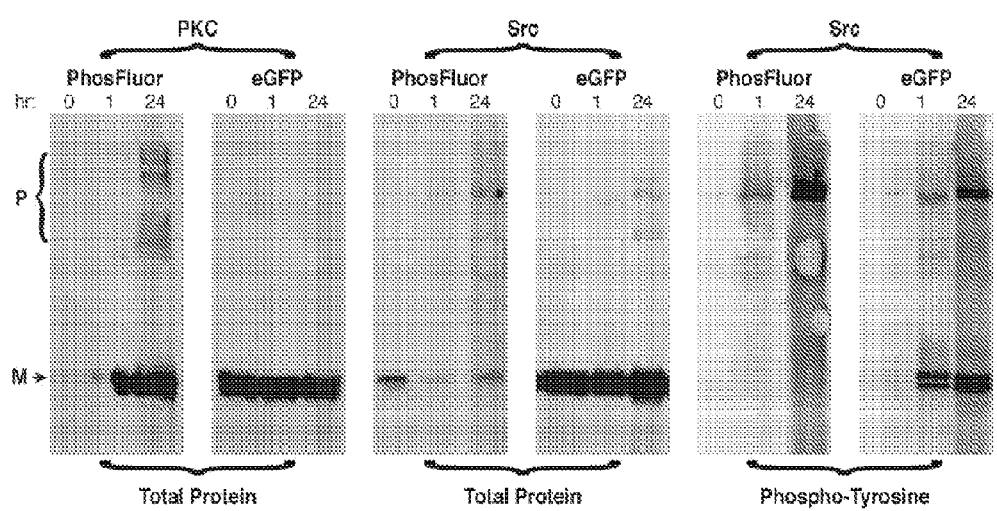
FIG. 10 discloses that PhosFluor is an avid substrate for PKC and Src. Equal quantities of PhosFluor or eGFP incubated with either PKC or Src for the indicated times (in hours) were resolved on 10% SDS-PAGE gels and immunoblotted to antibodies that reveal total protein (a polyhistidine monoclonal antibody) or phospho-tyrosine. M designates the position of the monomeric form of fluorescent protein while P designates the position of phosphorylated forms of the protein that have undergone a motility shift due to increased negative charge.

The excitation and emission spectra of PhosFluor were also obtained under control conditions and when phosphorylated (FIG. 10A). Remarkably, the excitation spectrum of PhosFluor was dramatically altered upon phosphorylation by different protein kinases, including Akt1 (FIG. 10A). A marked shift in the emission spectrum of PhosFluor was observed when this molecule was incubated with PKA, PKC or Akt1 (FIG. 10B). Similar changes in the emission spectrum were also observed when this protein was phosphoryated by CamKII and MAPK (data not shown). By contrast, no changes were observed in either the excitation or emission spectra of eGFP under the same conditions (FIGS. 10A-10B). These observations are highly significant because changes in the emission spectrum permits ratiometric measurements to be carried out, a highly robust method for quantitating spectral change in a fluorophore. Moreover, the effects reported here were carried out on the unmodified native PhosFluor protein. Enhanced effects would be expected if this protein is optimized for phosphorylation and/or expression as disclosed herein.

EXAMPLE 8

PhosFluor was Expressed Stably in a Mammalian Cell Line

Figure 11:
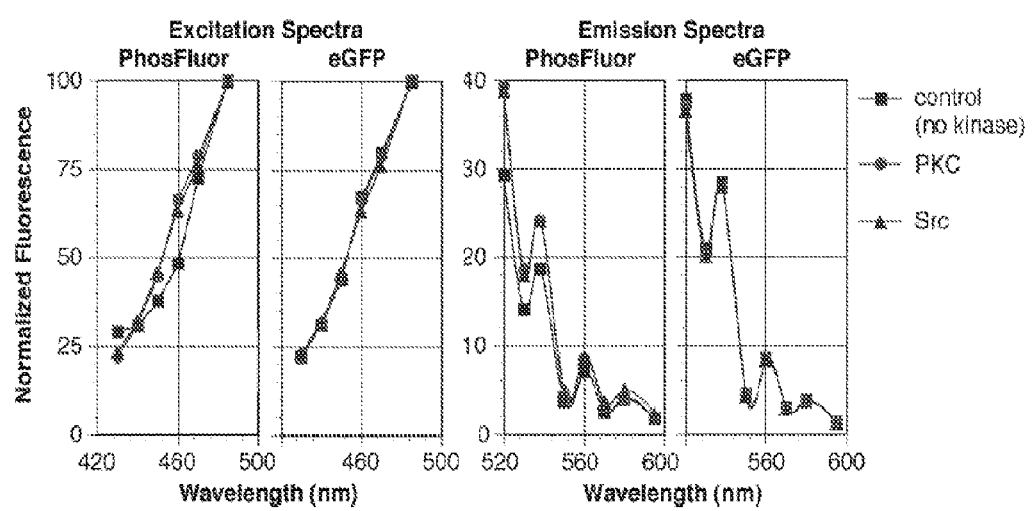
FIG. 11 discloses that phosphorylation of PhosFluor alters its spectral properties. The excitation and emission spectra of PhosFluor and eGFP are depicted under control conditions (no kinase) and after phosphorylation by the indicated kinases. The excitation and emission spectra for eGFP are all superimposed under a single curve, while phosphorylation of PhosFluor alters both spectra compared to control conditions.
Figure 12:
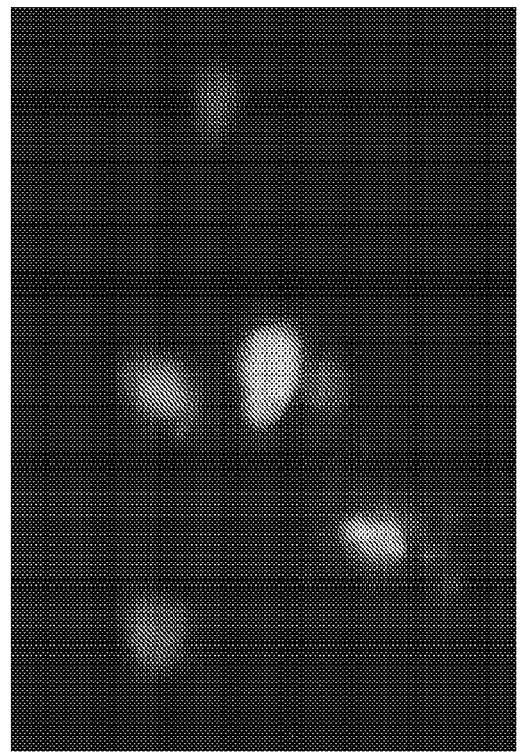
FIG. 12 discloses the expression of PhosFluor in mammalian cells. HEK-293 cells were transfected with PhosFluor driven by the CMV promoter, and visualized with a fluorescent microscope 1 week later.

PhosFluor was readily expressed in *E. coli*, but requires a few hours at room temperature or 4° C. to attain maximal fluorescence. To determine if this protein can be expressed in mammalian cells, PhosFluor was expressed in HEK-293 cells, a transformed cell line that expresses a multitude of different protein kinases. Fluorescence was observed in these cells five days post-transfection (FIG. 11), and was still stably expressed in cells selected for stable transfection 3 weeks later. This stable transfection indicated that the disclosed fluorescent polypeptide could be used in a cell-based phosphorylation detection system.

EXAMPLE 9

Converting Phosfluor into an Avid Substrate for Akt1 Kinase

Preliminary data indicate the presence of several phosphorylation consensus sites in PhosFluor. These sites are confirmed in the recombinant PhosFluor protein by phosphorylation in vitro using purified kinases, followed by digestion with trypsin and analysis by mass spectroscopy (Porton et al., *Biol Psychiatry* 55, 118-125, 2004). Peptides of interest are identified by an 80 Dalton mass shift (the molecular weight of a phosphate group) upon phosphorylation, and the identity of the phosphorylation site are inferred from the peptide's molecular weight and predicted sequence.

Conversion of functional phosphorylation sites into optimal substrates for Akt1 in PhosFluor is achieved by site-directed mutagenesis, a routine procedure (Kao et al., *Nat Neurosci* 5, 431-437, 2002). The effect of adding multiple Akt1 phosphorylation sites to the PhosFluor molecule is determined. These additional sites are believed to enhance the shift in the isoelectric point of the protein, resulting in a greater alteration of its spectral properties.

Recombinant PhosFluor protein or a variant thereof is produced in *E. coli* and purified using established techniques (Malhotra, *Methods Enzymol* 463, 239-258, 2009). Purified proteins are subjected to phosphorylation in vitro using recombinant Akt1 kinase. Reactions are monitored in a spectrofluorimeter after the addition of Akt1 kinase to record changes in intensity, excitation spectra or emission spectra.

Patents, patent applications, publications, product descriptions, and protocols which are cited throughout this application are incorporated herein by reference in their entireties. The embodiments illustrated and discussed in this specification are intended only to teach those skilled in the art the best way known to the inventors to make and use the invention. Nothing in this specification should be considered as limiting the scope of the present invention. Modifications and variation of the above-described embodiments of the invention are possible without departing from the invention, as appreciated by those skilled in the art in light of the above teachings. It is therefore understood that, within the scope of the claims and their equivalents, the invention may be practiced otherwise than as specifically described.

What is claimed is:

1. An isolated fluorescent polypeptide comprising an amino acid sequence selected from the group consisting of SEQ ID NOS: 10, 12, 14, 16, 18, 20, 22, 24, 26, 28, 30, 32, 34, 36, 38, 40, 42 and 44.

2. An isolated fluorescent polypeptide variant, wherein the fluorescent polypeptide variant comprises at least 90% sequence identity to SEQ ID NO: 10, 12, 14, 16, 18, 20, 22, 24, 26, 28, 30, 32, 34, 36, 38, or 40.

3. A fusion protein comprising an amino acid sequence of a protein of interest operatively joined to an amino acid sequence selected from the group consisting of SEQ ID NOS: 10, 12, 14, 16, 18, 20, 22, 24, 26, 28, 30, 32, 34, 36, 38, 40, 42 and 44.

4. A fusion protein comprising an amino acid sequence of a protein of interest operatively joined to an amino acid sequence having at least 90% sequence identity to SEQ ID NO: 10, 12, 14, 16, 18, 20, 22, 24, 26, 28, 30, 32, 34, 36, 38, or 40.

5. A kit for the detection of protein-protein interactions, comprising the isolated fluorescent polypeptide or variant thereof of claim 1 or 2.

6. A FRET pair comprising at least one isolated fluorescent protein of claim 1 or 2.

7. An isolated protein comprising the amino acid sequence of SEQ ID NO: 10 and further comprising at least one heterologous consensus sequence for phosphorylation by a protein kinase inserted into the amino acid sequence of SEQ ID NO: 10.

8. The isolated fluorescent polypeptide variant of claim 2, wherein the fluorescent polypeptide variant comprises SEQ ID NO: 28.

9. The isolated fluorescent polypeptide variant of claim 2, wherein the fluorescent polypeptide variant comprises SEQ ID NO: 14.

* * * * *